US007897575B2

(12) United States Patent
Hallenbeck et al.

(10) Patent No.: US 7,897,575 B2
(45) Date of Patent: *Mar. 1, 2011

(54) TREATMENT AND PREVENTION OF VASCULAR DEMENTIA

(75) Inventors: John M. Hallenbeck, Kensington, MD (US); Hideaki Wakita, Okazaki (JP)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 157 days.

This patent is subject to a terminal disclaimer.

(21) Appl. No.: 12/072,914

(22) Filed: Feb. 28, 2008

(65) Prior Publication Data

US 2008/0234196 A1 Sep. 25, 2008

Related U.S. Application Data

(63) Continuation-in-part of application No. PCT/US2006/034432, filed on Aug. 30, 2006, application No. 12/072,914, and a continuation-in-part of application No. PCT/US2007/021682, filed on Oct. 9, 2007, application No. 12/072,914, and a continuation-in-part of application No. 11/820,326, filed on Jun. 19, 2007, which is a continuation of application No. 10/296,423, filed as application No. PCT/US01/16583 on May 23, 2001, now Pat. No. 7,261,896.

(60) Provisional application No. 60/712,359, filed on Aug. 30, 2005, provisional application No. 60/828,732, filed on Oct. 9, 2006, provisional application No. 60/905,741, filed on Mar. 8, 2008, provisional application No. 60/206,693, filed on May 24, 2000.

(51) Int. Cl.
*A61K 38/17* (2006.01)
(52) U.S. Cl. ........ 514/17.5; 514/19.1; 514/957; 514/958
(58) Field of Classification Search ........................ None
See application file for complete search history.

(56) References Cited

U.S. PATENT DOCUMENTS

| 5,081,034 | A | 1/1992 | Bevilacqua et al. |
| 5,948,407 | A | 9/1999 | McGuinness et al. |
| 6,482,390 | B1 | 11/2002 | Hiscocks et al. |
| 6,974,573 | B2 | 12/2005 | Lee |
| 7,261,896 | B2 | 8/2007 | Hallenbeck et al. |
| 2004/0009125 | A1 | 1/2004 | Hallenbeck et al. |
| 2008/0234196 | A1 | 9/2008 | Hallenbeck et al. |

FOREIGN PATENT DOCUMENTS

| AU | 2001264813 B2 | 12/2005 |
| AU | 2005235514 A1 | 12/2005 |
| EP | 1842551 A | 10/2007 |
| WO | WO 91/08760 A1 | 6/1991 |
| WO | WO 93/16724 A1 | 9/1993 |
| WO | WO 00/04928 A | 2/2000 |
| WO | WO 01/89557 A | 11/2001 |
| WO | WO 2004/043361 A | 5/2004 |
| WO | WO 2004/056386 A | 7/2004 |
| WO | WO 2005/016962 A | 2/2005 |
| WO | WO 2006/099006 A | 9/2006 |
| WO | WO 2007/028133 A | 3/2007 |
| WO | WO 2008/045488 A2 | 4/2008 |

OTHER PUBLICATIONS

Becker-Andre et al. Eur. J. Biochem./FEBS, vol. 206, 1992, pp. 401-411.*
Abel, "Common condition emerges as possible stroke cause," *HealthLink Medical College of Wisonsin* 1-3, 2005.
Barsoum et al., "Effect of microencapsulated ampicillin on cell-mediated immune responses in mice," *J. Antimicrob Chemother.* 40(5):721-4, 1997.
Burrows et al., "Biological and biophysical characterization of recombinant soluble human E-selectin purified at large scale by reversed-phase high-performance liquid chromatography," *J. Chromatogr B Biomed Appl* 668(2):219-231, 1995.
Chen et al., "Mucosal tolerance to E-selectin provides cell-mediated protection against ischemic brain injury," *PNAS* 100(25):15107-15112, 2003.
del Zoppo et al., "Inflammation and Stroke: Putative Role for Cytokines, Adhesion Molecules and iNOS in Brain Response to Ischemia," *Brain Pathology* 10:95-112, 2000.
Endler et al., "The E-selectin S128R polymorphism is not a risk factor for coronary artery disease in patients with diabetes mellitus type 2," *Thromb Res.* 112(1-2):47-50, 2003.
Erkinjuntti, "Vascular Cognitive Impairment and Dementia," *Stroke: Pahtophysiology, Diagnosis, and Management* Chapter 29, 648-660.
Feuerstein et al., "Immune tolerance and Stroke: A turning point," *Stroke* 33(9):2163-4, 2002.
Hanninen and Harrison, "Mucosal tolerance to prevent type 1 diabetes: can the outcome be improved in humans?" *Rev Diabet Stud.* 1(3):113-121, 2004.
Huang et al., "Postischemic cerebrovascular E-selectin expression mediates tissue injury in murine stroke," *Stroke* 31(12):3047-3053, 2000. Illoh et al., "Mucosal tolerance to E-selectin and response to systemic inflammation," *J Cereb Bllod Flow Metab.* 26(12):1538-1550, 2006.
Li et al., "Consensus repeat domains of E-selectin enhance ligand binding," *J Bio Chem.* 269(6):4431-4437, 1994.
Matsumiya et al., "Dextran sulfate inhibits E-selectin-mediated neutrophil adhesion to endotoxin-activated vascular endothelial cells," *Life Sciences* 64(2):PL9-PL17, 1998.
Nakayama et al., "Intranasal administration of E-selectin to induce immunological tolerization can suppress subarachnoid hemorrhage-induced vasospasm implicating immune and inflammatory mechanisms in its genesis," Brain Res. 1132(1):177-184, 2007.

(Continued)

*Primary Examiner* — Jeffrey Stucker
*Assistant Examiner* — Stephen Gucker
(74) *Attorney, Agent, or Firm* — Klarquist Sparkman, LLP

(57) ABSTRACT

The invention relates to compositions and methods for treating or preventing vascular dementia in a mammal comprising mucosal administration of an amount of E-selectin polypeptide sufficient to induce bystander immune tolerance in the mammal. Another aspect of the invention relates to compositions useful for treating or preventing vascular dementia.

18 Claims, 22 Drawing Sheets
(6 of 22 Drawing Sheet(s) Filed in Color)

OTHER PUBLICATIONS

Sacco et al., "Classification of Ischemic Stroke," *Stroke: Pathophysiology, Diagnosis, and Management* Chapter 4, 61-74.

Simundic et al., "Soluble adhesion molecules in acute ischemic stroke," *Clin Invest Med.* 27(2):86-92, 2004.

Sughrue et al., "Anti-adhesion molecule strategies as potential neuroprotective agents in cerebral ischemia: a critical review of the literature," *Inflammation Research* 53(10):497-508, 2004.

Szalai et al., "The Arthus Reaction in Rodents: Species-Specific Requirement of Complement," *Journal of Immunology*, 164:463-468, 2000.

Takeda et al., "Induction of mucosal tolerance to E-selection prevents ischemic and hemorrhagic stroke in spontaneously hypertensive genetically stroke-prone rats," *Stroke* 33:2156-2164, 2002.

Takeda et al., "In spontaneously hypertensive, genetically stroke-prone rate (SHR-SP), induction of mucosal tolerance to E-selectin prevents ischemic and hemorrhagic stroke," *Stroke Symposium* 114, 2002.

Ulich et al., "Intratracheal administration of endotoxin and cytokines: VIII LPS induces E-selectin expression; anti-E-selectin and soluble E-selectin inhibit acute inflammation," *Inflammation* 18(4):389-398, 1994.

Wang et al., "Demonstration of increased endothelial-leukocyte adhesion molecule-1 mRNA expression in rat ischemic cortex," *Stroke* 26(9):1665-1669, 1995.

Welply et al., "Selectins as potential targets of therapeutic intervention in inflammatory diseases," *Biochim Biophys Acta.* 1197(2):215-226, 1994.

Federal Occupational Health, New vaccine may provide hope to people at risk for stroke, 2005.

* cited by examiner

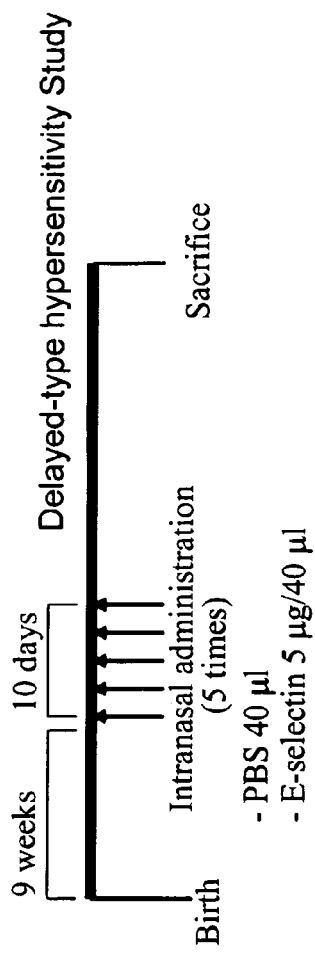
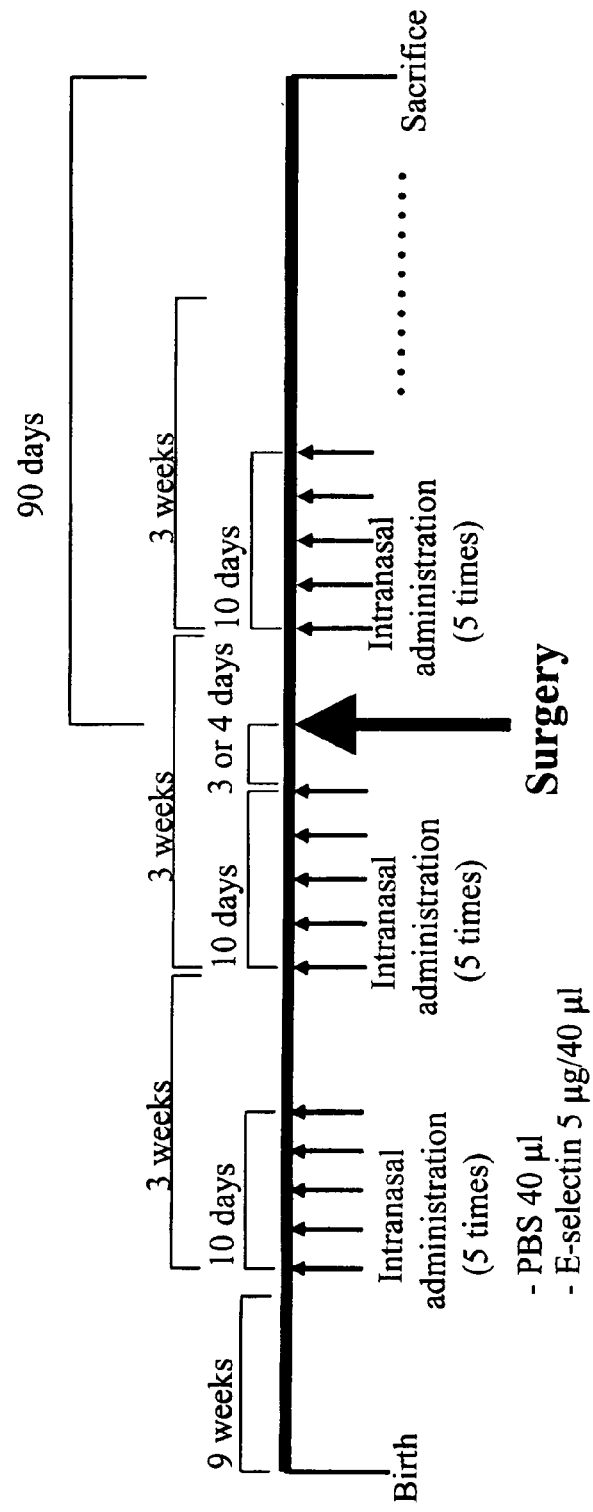

```
              1                                                      50
wt M30640     MIASQFLSAL TLVLLIKE.S .GAWSYNTST EAMTYDEASA YCQQRYTHLV
wt NM000450   MIASQFLSAL TLVLLIKE.S .GAWSYNTST EAMTYDEASA YCQQRYTHLV
"new" no-tag  MPLYKLLNVL WLVAVSNAIP .GSWSYNTST EAMTYDEASA YCQQRYTHLV
"old" tagged  ~~~MGWSWI FLFLLSGTAS VHSWSYNTST EAMTYDEASA YCQQRYTHLV
              ////////// ////////// ////////// ////////// //////////

51                                                    100
              AIQNKEEIEY LNSILSYSPS YYWIGIRKVN NVWVWVGTQK PLTEEAKNWA
              AIQNKEEIEY LNSILSYSPS YYWIGIRKVN NVWVWVGTQK PLTEEAKNWA
              AIQNKEEIEY LNSILSYSPS YYWIGIRKVN NVWVWVGTQK PLTEEAKNWA
              AIQNKEEIEY LNSILSYSPS YYWIGIRKVN NVWVWVGTQK PLTEEAKNWA
              ////////// ////////// ////////// ////////// //////////

101                                                   150
              PGEPNNRQKD EDCVEIYIKR EKDVGMWNDE RCSKKKLALC YTAACTNTSC
              PGEPNNRQKD EDCVEIYIKR EKDVGMWNDE RCSKKKLALC YTAACTNTSC
              PGEPNNRQKD EDCVEIYIKR EKDVGMWNDE RCSKKKLALC YTAACTNTSC
              PGEPNNRQKD EDCVEIYIKR EKDVGMWNDE RCSKKKLALC YTAACTNTSC
              ////////// ////////// ////////// //         @@@@@

151                                                   200
              SGHGECVETI NNYTCKCDPG FSGLKCEQIV NCTALESPEH GSLVCSHPLG
              SGHGECVETI NNYTCKCDPG FSGLKCEQIV NCTALESPEH GSLVCSHPLG
              SGHGECVETI NNYTCKCDPG FSGLKCEQIV NCTALESPEH GSLVCSHPLG
              SGHGECVETI NNYTCKCDPG FSGLKCEQIV NCTALESPEH GSLVCSHPLG
              @@@@@@@@@@ @@@@@@@@@@ @@@@@@@
```

FIG. 17A

```
201                                                                250
NFSYNSSCSI  SCDRGYLPSS  METMQCMSSG  EWSAPIPACN  VVECDAVTNP
NFSYNSSCSI  SCDRGYLPSS  METMQCMSSG  EWSAPIPACN  VVECDAVTNP
NFSYNSSCSI  SCDRGYLPSS  METMQCMSSG  EWSAPIPACN  VVECDAVTNP
NFSYNSSCSI  SCDRGYLPSS  METMQCMSSG  EWSAPIPACN  VVECDAVTNP 251                                                                300
ANGFVECFQN  PGSFPWNTTC  TFDCEEGFEL  MGAQSLQCTS  SGNWDNEKPT
ANGFVECFQN  PGSFPWNTTC  TFDCEEGFEL  MGAQSLQCTS  SGNWDNEKPT
ANGFVECFQN  PGSFPWNTTC  TFDCEEGFEL  MGAQSLQCTS  SGNWDNEKPT
ANGFVECFQN  PGSFPWNTTC  TFDCEEGFEL  MGAQSLQCTS  SGNWDNEKPT 301                                                                350
CKAVT....C  RAVRQPQNGS  VRCSHSPAGE  FTFKSSCNFT  CEEGFMLQGP
CKAVT....C  RAVRQPQNGS  VRCSHSPAGE  FTFKSSCNFT  CEEGFMLQGP
CKAVT.....  RS*~~~~~~~  ~~~~~~~~~~  ~~~~~~~~~~  ~~~~~~~ ~~~
CKAVTGGAST  RAAEQKLISE  EDLNGTRSGH  HHHHH**~~~  ~~~~~~~~~~~
            #######     ###         #   #####

351                                                                400
AQVECTTQGQ  WTQQIPVCEA  FQCTALSNPE  RGYMNCLPSA  SGSFRYGSSC
AQVECTTQGQ  WTQQIPVCEA  FQCTALSNPE  RGYMNCLPSA  SGSFRYGSSC
~~~~~~~~~~  ~~~~~~~~~~  ~~~~~~~~~~  ~~~~~~~~~~  ~~~~~~~ ~~~
~~~~~~~~~~  ~~~~~~~~~~  ~~~~~~~~~~  ~~~~~~~~~~  ~~~~~~~ ~~~
```

*FIG. 17B*

```
401                                                              450
EFSCEQGFVL KGSKRLQCGP TGEWDNEKPT CEAVRCDAVH QPPKGLVRCA
EFSCEQGFVL KGSKRLQCGP TGEWDNEKPT CEAVRCDAVH QPPKGLVRCA
~~~~~~~~~~ ~~~~~~~~~~ ~~~~~~~~~~ ~~~~~~~~~~ ~~~~~~~~~~
~~~~~~~~~~ ~~~~~~~~~~ ~~~~~~~~~~ ~~~~~~~~~~ ~~~~~~~~~~

451                                                              500
HSPIGEFTYK SSCAFSCEEG FELHGSTQLE CTSQGQWTEE VPSCQVVKCS
HSPIGEFTYK SSCAFSCEEG FELYGSTQLE CTSQGQWTEE VPSCQVVKCS
~~~~~~~~~~ ~~~~~~~~~~ ~~~~~~~~~~ ~~~~~~~~~~ ~~~~~~~~~~
~~~~~~~~~~ ~~~~~~~~~~ ~~~~~~~~~~ ~~~~~~~~~~ ~~~~~~~~~~

501                                                              550
SLAVPGKINM SCSGEPVFGT VCKFACPEGW TLNGSAARTC GATGHWSGLL
SLAVPGKINM SCSGEPVFGT VCKFACPEGW TLNGSAARTC GATGHWSGLL
~~~~~~~~~~ ~~~~~~~~~~ ~~~~~~~~~~ ~~~~~~~~~~ ~~~~~~~~~~
~~~~~~~~~~ ~~~~~~~~~~ ~~~~~~~~~~ ~~~~~~~~~~ ~~~~~~~~~~

551                                                              600
PTCEAPTESN IPLVAGLSAA GLSLLTLAPF LLWLRKCLRK AKKFVPASSC
PTCEAPTESN IPLVAGLSAA GLSLLTLAPF LLWLRKCLRK AKKFVPASSC
~~~~~~~~~~ ~~~~~~~~~~ ~~~~~~~~~~ ~~~~~~~~~~ ~~~~~~~~~~
~~~~~~~~~~ ~~~~~~~~~~ ~~~~~~~~~~ ~~~~~~~~~~ ~~~~~~~~~~
           ******** ****** **

601             616
QSLESDGSYQ KPSYIL
QSLESDGSYQ KPSYIL
~~~~~~~~~~ ~~~~~~
```

FIG. 17C

```
HUMAN   1 MgwswiflfllsgtasvhsWSYNTSTEAMTYDEASAYCQQRYTHLVAIQN  50
          |||||||||||||||||||||| || |.| |||||||||||. ||||||||
MOUSE   1 MGWSWIFLFLLSGTASVHSWYYNASSELMTYDEASAYCQRDYTHLVAIQN  50

51 KEEIEYLNSILSYSPSYYWIGIRKVNNVWVWVGTQKPLTEEAKNWAPGEP 100
          |||| |||| | :||||||||||||||||:|||| |||||||.|||||||
       51 KEEINYLNSNLKHSPSYYWIGIRKVNNVWIWVGTGKPLTEEAQNWAPGEP 100

101 NNRQKDEDCVEIYIKREKDVGMWNDERCSKKKLALCYTAACTNTSCSGHG 150
          ||:|:.|||||||||.| || |||||||.|||||||||||.||| ||||||
      101 NNKQRNEDCVEIYIQRTKDSGMWNDERCNKKKLALCYTASCTNASCSGHG 150

151 ECVETINNYTCKCDPGFSGLKCEQIVNCTALESPEHGSLVCSHPLGNFSY 200
          ||:||||.||||| ||| | ||| | |   | |::||| |||| | |||
      151 ECIETINSYTCKCHPGFLGPNCEQAVTCKPQEHPDYGSLNCSHPFGPFSY 200

201 NSSCSISCDRGYLPSSME.TMQCMSSGEWSAPIPACNVVECDAVTNPANG 249
          |||||   | |||||||||| |..| ||||||||| |||.||||:|.|.||.|
      201 NSSCSFGCKRGYLPSSMETTVRCTSSGEWSAPAPACHVVECEALTHPAHG 250

250 FVECFQNPGSFPWNTTCTFDCEEGFELMGAQSLQCTSSGNWDNEKPTCKA 299
          .| ||||:||||||||||| ||: .|||.||||||||| |||| |.|||
      251 IRKCSSNPGSYPWNTTCTFDCVEGYRRVGAQNLQCTSSGIWDNETPSCKA 300

300 VT 301      (SEQ ID NO:25)
          ||
      301 VT 302      (SEQ ID NO:26)
```

FIG. 18

SEQUENCE LISTING

```
<160> NUMBER OF SEQ ID NOS: 33

<210> SEQ ID NO 1
<211> LENGTH: 610
<212> TYPE: PRT
<213> ORGANISM: Homo sapiens

<400> SEQUENCE: 1

Met Ile Ala Ser Gln Phe Leu Ser Ala Leu Thr Leu Val Leu Leu Ile
 1               5                  10                  15

Lys Glu Ser Gly Ala Trp Ser Tyr Asn Thr Ser Thr Glu Ala Met Thr
            20                  25                  30

Tyr Asp Glu Ala Ser Ala Tyr Cys Gln Gln Arg Tyr Thr His Leu Val
        35                  40                  45

Ala Ile Gln Asn Lys Glu Glu Ile Glu Tyr Leu Asn Ser Ile Leu Ser
    50                  55                  60

Tyr Ser Pro Ser Tyr Tyr Trp Ile Gly Ile Arg Lys Val Asn Asn Val
65                  70                  75                  80

Trp Val Trp Val Gly Thr Gln Lys Pro Leu Thr Glu Glu Ala Lys Asn
                85                  90                  95

Trp Ala Pro Gly Glu Pro Asn Asn Arg Gln Lys Asp Glu Asp Cys Val
            100                 105                 110

Glu Ile Tyr Ile Lys Arg Glu Lys Asp Val Gly Met Trp Asn Asp Glu
        115                 120                 125

Arg Cys Ser Lys Lys Lys Leu Ala Leu Cys Tyr Thr Ala Ala Cys Thr
    130                 135                 140

Asn Thr Ser Cys Ser Gly His Gly Glu Cys Val Glu Thr Ile Asn Asn
145                 150                 155                 160

Tyr Thr Cys Lys Cys Asp Pro Gly Phe Ser Gly Leu Lys Cys Glu Gln
                165                 170                 175

Ile Val Asn Cys Thr Ala Leu Glu Ser Pro Glu His Gly Ser Leu Val
            180                 185                 190

Cys Ser His Pro Leu Gly Asn Phe Ser Tyr Asn Ser Ser Cys Ser Ile
        195                 200                 205

Ser Cys Asp Arg Gly Tyr Leu Pro Ser Ser Met Glu Thr Met Gln Cys
    210                 215                 220

Met Ser Ser Gly Glu Trp Ser Ala Pro Ile Pro Ala Cys Asn Val Val
225                 230                 235                 240

Glu Cys Asp Ala Val Thr Asn Pro Ala Asn Gly Phe Val Glu Cys Phe
```

```
                    245                 250                 255
Gln Asn Pro Gly Ser Phe Pro Trp Asn Thr Thr Cys Thr Phe Asp Cys
                260                 265                 270

Glu Glu Gly Phe Glu Leu Met Gly Ala Gln Ser Leu Gln Cys Thr Ser
            275                 280                 285

Ser Gly Asn Trp Asp Asn Glu Lys Pro Thr Cys Lys Ala Val Thr Cys
        290                 295                 300

Arg Ala Val Arg Gln Pro Gln Asn Gly Ser Val Arg Cys Ser His Ser
305                 310                 315                 320

Pro Ala Gly Glu Phe Thr Phe Lys Ser Ser Cys Asn Phe Thr Cys Glu
                325                 330                 335

Glu Gly Phe Met Leu Gln Gly Pro Ala Gln Val Glu Cys Thr Thr Gln
            340                 345                 350

Gly Gln Trp Thr Gln Gln Ile Pro Val Cys Glu Ala Phe Gln Cys Thr
        355                 360                 365

Ala Leu Ser Asn Pro Glu Arg Gly Tyr Met Asn Cys Leu Pro Ser Ala
    370                 375                 380

Ser Gly Ser Phe Arg Tyr Gly Ser Ser Cys Glu Phe Ser Cys Glu Gln
385                 390                 395                 400

Gly Phe Val Leu Lys Gly Ser Lys Arg Leu Gln Cys Gly Pro Thr Gly
                405                 410                 415

Glu Trp Asp Asn Glu Lys Pro Thr Cys Glu Ala Val Arg Cys Asp Ala
            420                 425                 430

Val His Gln Pro Pro Lys Gly Leu Val Arg Cys Ala His Ser Pro Ile
        435                 440                 445

Gly Glu Phe Thr Tyr Lys Ser Ser Cys Ala Phe Ser Cys Glu Glu Gly
    450                 455                 460

Phe Glu Leu His Gly Ser Thr Gln Leu Glu Cys Thr Ser Gln Gly Gln
465                 470                 475                 480

Trp Thr Glu Glu Val Pro Ser Cys Gln Val Val Lys Cys Ser Ser Leu
                485                 490                 495

Ala Val Pro Gly Lys Ile Asn Met Ser Cys Ser Gly Glu Pro Val Phe
            500                 505                 510

Gly Thr Val Cys Lys Phe Ala Cys Pro Glu Gly Trp Thr Leu Asn Gly
        515                 520                 525

Ser Ala Ala Arg Thr Cys Gly Ala Thr Gly His Trp Ser Gly Leu Leu
    530                 535                 540

Pro Thr Cys Glu Ala Pro Thr Glu Ser Asn Ile Pro Leu Val Ala Gly
545                 550                 555                 560

Leu Ser Ala Ala Gly Leu Ser Leu Leu Thr Leu Ala Pro Phe Leu Leu
                565                 570                 575

Trp Leu Arg Lys Cys Leu Arg Lys Ala Lys Lys Phe Val Pro Ala Ser
            580                 585                 590

Ser Cys Gln Ser Leu Glu Ser Asp Gly Ser Tyr Gln Lys Pro Ser Tyr
        595                 600                 605

Ile Leu
    610

<210> SEQ ID NO 2
<211> LENGTH: 589
<212> TYPE: PRT
<213> ORGANISM: Homo sapiens

<400> SEQUENCE: 2

Trp Ser Tyr Asn Thr Ser Thr Glu Ala Met Thr Tyr Asp Glu Ala Ser
```

-continued

```
            1               5                  10                 15
Ala Tyr Cys Gln Gln Arg Tyr Thr His Leu Val Ala Ile Gln Asn Lys
                    20                  25                  30

Glu Glu Ile Glu Tyr Leu Asn Ser Ile Leu Ser Tyr Ser Pro Ser Tyr
                    35                  40                  45

Tyr Trp Ile Gly Ile Arg Lys Val Asn Asn Val Trp Val Trp Val Gly
                    50                  55                  60

Thr Gln Lys Pro Leu Thr Glu Glu Ala Lys Asn Trp Ala Pro Gly Glu
 65                     70                  75                  80

Pro Asn Asn Arg Gln Lys Asp Glu Asp Cys Val Glu Ile Tyr Ile Lys
                    85                  90                  95

Arg Glu Lys Asp Val Gly Met Trp Asn Asp Glu Arg Cys Ser Lys Lys
                   100                 105                 110

Lys Leu Ala Leu Cys Tyr Thr Ala Ala Cys Thr Asn Thr Ser Cys Ser
                   115                 120                 125

Gly His Gly Glu Cys Val Glu Thr Ile Asn Asn Tyr Thr Cys Lys Cys
                   130                 135                 140

Asp Pro Gly Phe Ser Gly Leu Lys Cys Glu Gln Ile Val Asn Cys Thr
145                     150                 155                 160

Ala Leu Glu Ser Pro Glu His Gly Ser Leu Val Cys Ser His Pro Leu
                   165                 170                 175

Gly Asn Phe Ser Tyr Asn Ser Ser Cys Ser Ile Ser Cys Asp Arg Gly
                   180                 185                 190

Tyr Leu Pro Ser Ser Met Glu Thr Met Gln Cys Met Ser Ser Gly Glu
                   195                 200                 205

Trp Ser Ala Pro Ile Pro Ala Cys Asn Val Val Glu Cys Asp Ala Val
                   210                 215                 220

Thr Asn Pro Ala Asn Gly Phe Val Glu Cys Phe Gln Asn Pro Gly Ser
225                     230                 235                 240

Phe Pro Trp Asn Thr Thr Cys Thr Phe Asp Cys Glu Glu Gly Phe Glu
                   245                 250                 255

Leu Met Gly Ala Gln Ser Leu Gln Cys Thr Ser Ser Gly Asn Trp Asp
                   260                 265                 270

Asn Glu Lys Pro Thr Cys Lys Ala Val Thr Cys Arg Ala Val Arg Gln
                   275                 280                 285

Pro Gln Asn Gly Ser Val Arg Cys Ser His Ser Pro Ala Gly Glu Phe
                   290                 295                 300

Thr Phe Lys Ser Ser Cys Asn Phe Thr Cys Glu Glu Gly Phe Met Leu
305                     310                 315                 320

Gln Gly Pro Ala Gln Val Glu Cys Thr Thr Gln Gly Gln Trp Thr Gln
                   325                 330                 335

Gln Ile Pro Val Cys Glu Ala Phe Gln Cys Thr Ala Leu Ser Asn Pro
                   340                 345                 350

Glu Arg Gly Tyr Met Asn Cys Leu Pro Ser Ala Ser Gly Ser Phe Arg
                   355                 360                 365

Tyr Gly Ser Ser Cys Glu Phe Ser Cys Glu Gln Gly Phe Val Leu Lys
                   370                 375                 380

Gly Ser Lys Arg Leu Gln Cys Gly Pro Thr Gly Glu Trp Asp Asn Glu
385                     390                 395                 400

Lys Pro Thr Cys Glu Ala Val Arg Cys Asp Ala Val His Gln Pro Pro
                   405                 410                 415

Lys Gly Leu Val Arg Cys Ala His Ser Pro Ile Gly Glu Phe Thr Tyr
                   420                 425                 430
```

```
Lys Ser Ser Cys Ala Phe Ser Cys Glu Glu Gly Phe Glu Leu His Gly
        435                 440                 445

Ser Thr Gln Leu Glu Cys Thr Ser Gln Gly Gln Trp Thr Glu Glu Val
    450                 455                 460

Pro Ser Cys Gln Val Val Lys Cys Ser Ser Leu Ala Val Pro Gly Lys
465                 470                 475                 480

Ile Asn Met Ser Cys Ser Gly Glu Pro Val Phe Gly Thr Val Cys Lys
                485                 490                 495

Phe Ala Cys Pro Glu Gly Trp Thr Leu Asn Gly Ser Ala Ala Arg Thr
                500                 505                 510

Cys Gly Ala Thr Gly His Trp Ser Gly Leu Leu Pro Thr Cys Glu Ala
            515                 520                 525

Pro Thr Glu Ser Asn Ile Pro Leu Val Ala Gly Leu Ser Ala Ala Gly
        530                 535                 540

Leu Ser Leu Leu Thr Leu Ala Pro Phe Leu Leu Trp Leu Arg Lys Cys
545                 550                 555                 560

Leu Arg Lys Ala Lys Lys Phe Val Pro Ala Ser Ser Cys Gln Ser Leu
                565                 570                 575

Glu Ser Asp Gly Ser Tyr Gln Lys Pro Ser Tyr Ile Leu
                580                 585

<210> SEQ ID NO 3
<211> LENGTH: 535
<212> TYPE: PRT
<213> ORGANISM: Homo sapiens

<400> SEQUENCE: 3

Trp Ser Tyr Asn Thr Ser Thr Glu Ala Met Thr Tyr Asp Glu Ala Ser
1               5                   10                  15

Ala Tyr Cys Gln Gln Arg Tyr Thr His Leu Val Ala Ile Gln Asn Lys
                20                  25                  30

Glu Glu Ile Glu Tyr Leu Asn Ser Ile Leu Ser Tyr Ser Pro Ser Tyr
            35                  40                  45

Tyr Trp Ile Gly Ile Arg Lys Val Asn Asn Val Trp Val Trp Val Gly
    50                  55                  60

Thr Gln Lys Pro Leu Thr Glu Glu Ala Lys Asn Trp Ala Pro Gly Glu
65                  70                  75                  80

Pro Asn Asn Arg Gln Lys Asp Glu Asp Cys Val Glu Ile Tyr Ile Lys
                85                  90                  95

Arg Glu Lys Asp Val Gly Met Trp Asn Asp Glu Arg Cys Ser Lys Lys
            100                 105                 110

Lys Leu Ala Leu Cys Tyr Thr Ala Ala Cys Thr Asn Thr Ser Cys Ser
        115                 120                 125

Gly His Gly Glu Cys Val Glu Thr Ile Asn Asn Tyr Thr Cys Lys Cys
    130                 135                 140

Asp Pro Gly Phe Ser Gly Leu Lys Cys Glu Gln Ile Val Asn Cys Thr
145                 150                 155                 160

Ala Leu Glu Ser Pro Glu His Gly Ser Leu Val Cys Ser His Pro Leu
                165                 170                 175

Gly Asn Phe Ser Tyr Asn Ser Ser Cys Ser Ile Ser Cys Asp Arg Gly
            180                 185                 190

Tyr Leu Pro Ser Ser Met Glu Thr Met Gln Cys Met Ser Ser Gly Glu
        195                 200                 205

Trp Ser Ala Pro Ile Pro Ala Cys Asn Val Val Glu Cys Asp Ala Val
    210                 215                 220
```

```
Thr Asn Pro Ala Asn Gly Phe Val Glu Cys Phe Gln Asn Pro Gly Ser
225                 230                 235                 240

Phe Pro Trp Asn Thr Thr Cys Thr Phe Asp Cys Glu Glu Gly Phe Glu
            245                 250                 255

Leu Met Gly Ala Gln Ser Leu Gln Cys Thr Ser Ser Gly Asn Trp Asp
            260                 265                 270

Asn Glu Lys Pro Thr Cys Lys Ala Val Thr Cys Arg Ala Val Arg Gln
        275                 280                 285

Pro Gln Asn Gly Ser Val Arg Cys Ser His Ser Pro Ala Gly Glu Phe
    290                 295                 300

Thr Phe Lys Ser Ser Cys Asn Phe Thr Cys Glu Glu Gly Phe Met Leu
305                 310                 315                 320

Gln Gly Pro Ala Gln Val Glu Cys Thr Thr Gln Gly Gln Trp Thr Gln
            325                 330                 335

Gln Ile Pro Val Cys Glu Ala Phe Gln Cys Thr Ala Leu Ser Asn Pro
            340                 345                 350

Glu Arg Gly Tyr Met Asn Cys Leu Pro Ser Ala Ser Gly Ser Phe Arg
        355                 360                 365

Tyr Gly Ser Ser Cys Glu Phe Ser Cys Glu Gln Gly Phe Val Leu Lys
370                 375                 380

Gly Ser Lys Arg Leu Gln Cys Gly Pro Thr Gly Glu Trp Asp Asn Glu
385                 390                 395                 400

Lys Pro Thr Cys Glu Ala Val Arg Cys Asp Ala Val His Gln Pro Pro
            405                 410                 415

Lys Gly Leu Val Arg Cys Ala His Ser Pro Ile Gly Glu Phe Thr Tyr
            420                 425                 430

Lys Ser Ser Cys Ala Phe Ser Cys Glu Glu Gly Phe Glu Leu His Gly
        435                 440                 445

Ser Thr Gln Leu Glu Cys Thr Ser Gln Gly Gln Trp Thr Glu Glu Val
    450                 455                 460

Pro Ser Cys Gln Val Val Lys Cys Ser Ser Leu Ala Val Pro Gly Lys
465                 470                 475                 480

Ile Asn Met Ser Cys Ser Gly Glu Pro Val Phe Gly Thr Val Cys Lys
            485                 490                 495

Phe Ala Cys Pro Glu Gly Trp Thr Leu Asn Gly Ser Ala Ala Arg Thr
            500                 505                 510

Cys Gly Ala Thr Gly His Trp Ser Gly Leu Leu Pro Thr Cys Glu Ala
        515                 520                 525

Pro Thr Glu Ser Asn Ile Pro
    530                 535

<210> SEQ ID NO 4
<211> LENGTH: 138
<212> TYPE: PRT
<213> ORGANISM: Homo sapiens

<400> SEQUENCE: 4

Pro Lys Gly Leu Val Arg Cys Ala His Ser Pro Ile Gly Glu Phe Thr
1               5                   10                  15

Tyr Lys Ser Ser Cys Ala Phe Ser Cys Glu Glu Gly Phe Glu Leu Tyr
            20                  25                  30

Gly Ser Thr Gln Leu Glu Cys Thr Ser Gln Gly Gln Trp Thr Glu Glu
        35                  40                  45

Val Pro Ser Cys Gln Val Val Lys Cys Ser Ser Leu Ala Val Pro Gly
    50                  55                  60
```

```
Lys Ile Asn Met Ser Cys Ser Gly Glu Pro Val Phe Gly Thr Val Cys
 65                  70                  75                  80

Lys Phe Ala Cys Pro Glu Gly Trp Thr Leu Asn Gly Ser Ala Ala Arg
                 85                  90                  95

Thr Cys Gly Ala Thr Gly His Trp Ser Gly Leu Leu Pro Thr Cys Glu
            100                 105                 110

Ala Pro Thr Glu Ser Asn Ile Pro Leu Val Ala Gly Leu Ser Ala Ala
            115                 120                 125

Gly Leu Ser Leu Leu Thr Leu Ala Pro Phe
130                 135

<210> SEQ ID NO 5
<211> LENGTH: 306
<212> TYPE: PRT
<213> ORGANISM: Homo sapiens

<400> SEQUENCE: 5

Met Pro Leu Tyr Lys Leu Leu Asn Val Leu Trp Leu Val Ala Val Ser
  1               5                  10                  15

Asn Ala Ile Pro Gly Ser Trp Ser Tyr Asn Thr Ser Thr Glu Ala Met
             20                  25                  30

Thr Tyr Asp Glu Ala Ser Ala Tyr Cys Gln Gln Arg Tyr Thr His Leu
         35                  40                  45

Val Ala Ile Gln Asn Lys Glu Glu Ile Glu Tyr Leu Asn Ser Ile Leu
 50                  55                  60

Ser Tyr Ser Pro Ser Tyr Tyr Trp Ile Gly Ile Arg Lys Val Asn Asn
 65                  70                  75                  80

Val Trp Val Trp Val Gly Thr Gln Lys Pro Leu Thr Glu Glu Ala Lys
                 85                  90                  95

Asn Trp Ala Pro Gly Glu Pro Asn Asn Arg Gln Lys Asp Glu Asp Cys
            100                 105                 110

Val Glu Ile Tyr Ile Lys Arg Glu Lys Asp Val Gly Met Trp Asn Asp
            115                 120                 125

Glu Arg Cys Ser Lys Lys Lys Leu Ala Leu Cys Tyr Thr Ala Ala Cys
            130                 135                 140

Thr Asn Thr Ser Cys Ser Gly His Gly Glu Cys Val Glu Thr Ile Asn
145                 150                 155                 160

Asn Tyr Thr Cys Lys Cys Asp Pro Gly Phe Ser Gly Leu Lys Cys Glu
                165                 170                 175

Gln Ile Val Asn Cys Thr Ala Leu Glu Ser Pro Glu His Gly Ser Leu
            180                 185                 190

Val Cys Ser His Pro Leu Gly Asn Phe Ser Tyr Asn Ser Ser Cys Ser
            195                 200                 205

Ile Ser Cys Asp Arg Gly Tyr Leu Pro Ser Ser Met Glu Thr Met Gln
210                 215                 220

Cys Met Ser Ser Gly Glu Trp Ser Ala Pro Ile Pro Ala Cys Asn Val
225                 230                 235                 240

Val Glu Cys Asp Ala Val Thr Asn Pro Ala Asn Gly Phe Val Glu Cys
            245                 250                 255

Phe Gln Asn Pro Gly Ser Phe Pro Trp Asn Thr Thr Cys Thr Phe Asp
            260                 265                 270

Cys Glu Glu Gly Phe Glu Leu Met Gly Ala Gln Ser Leu Gln Cys Thr
            275                 280                 285

Ser Ser Gly Asn Trp Asp Asn Glu Lys Pro Thr Cys Lys Ala Val Thr
290                 295                 300
```

Arg Ser
305

<210> SEQ ID NO 6
<211> LENGTH: 304
<212> TYPE: PRT
<213> ORGANISM: Homo sapiens

<400> SEQUENCE: 6

Met Pro Leu Tyr Lys Leu Leu Asn Val Leu Trp Leu Val Ala Val Ser
 1               5                  10                  15

Asn Ala Ile Pro Gly Ser Trp Ser Tyr Asn Thr Ser Thr Glu Ala Met
             20                  25                  30

Thr Tyr Asp Glu Ala Ser Ala Tyr Cys Gln Gln Arg Tyr Thr His Leu
         35                  40                  45

Val Ala Ile Gln Asn Lys Glu Glu Ile Glu Tyr Leu Asn Ser Ile Leu
     50                  55                  60

Ser Tyr Ser Pro Ser Tyr Tyr Trp Ile Gly Ile Arg Lys Val Asn Asn
 65                  70                  75                  80

Val Trp Val Trp Val Gly Thr Gln Lys Pro Leu Thr Glu Glu Ala Lys
                 85                  90                  95

Asn Trp Ala Pro Gly Glu Pro Asn Asn Arg Gln Lys Asp Glu Asp Cys
            100                 105                 110

Val Glu Ile Tyr Ile Lys Arg Glu Lys Asp Val Gly Met Trp Asn Asp
        115                 120                 125

Glu Arg Cys Ser Lys Lys Lys Leu Ala Leu Cys Tyr Thr Ala Ala Cys
    130                 135                 140

Thr Asn Thr Ser Cys Ser Gly His Gly Glu Cys Val Glu Thr Ile Asn
145                 150                 155                 160

Asn Tyr Thr Cys Lys Cys Asp Pro Gly Phe Ser Gly Leu Lys Cys Glu
                165                 170                 175

Gln Ile Val Asn Cys Thr Ala Leu Glu Ser Pro Glu His Gly Ser Leu
            180                 185                 190

Val Cys Ser His Pro Leu Gly Asn Phe Ser Tyr Asn Ser Ser Cys Ser
        195                 200                 205

Ile Ser Cys Asp Arg Gly Tyr Leu Pro Ser Ser Met Glu Thr Met Gln
    210                 215                 220

Cys Met Ser Ser Gly Glu Trp Ser Ala Pro Ile Pro Ala Cys Asn Val
225                 230                 235                 240

Val Glu Cys Asp Ala Val Thr Asn Pro Ala Asn Gly Phe Val Glu Cys
                245                 250                 255

Phe Gln Asn Pro Gly Ser Phe Pro Trp Asn Thr Thr Cys Thr Phe Asp
            260                 265                 270

Cys Glu Glu Gly Phe Glu Leu Met Gly Ala Gln Ser Leu Gln Cys Thr
        275                 280                 285

Ser Ser Gly Asn Trp Asp Asn Glu Lys Pro Thr Cys Lys Ala Val Thr
    290                 295                 300

<210> SEQ ID NO 7
<211> LENGTH: 284
<212> TYPE: PRT
<213> ORGANISM: Homo sapiens

<400> SEQUENCE: 7

Trp Ser Tyr Asn Thr Ser Thr Glu Ala Met Thr Tyr Asp Glu Ala Ser
 1               5                  10                  15

Ala Tyr Cys Gln Gln Arg Tyr Thr His Leu Val Ala Ile Gln Asn Lys

```
            20                  25                  30
Glu Glu Ile Glu Tyr Leu Asn Ser Ile Leu Ser Tyr Ser Pro Ser Tyr
        35                  40                  45
Tyr Trp Ile Gly Ile Arg Lys Val Asn Asn Val Trp Val Trp Val Gly
        50                  55                  60
Thr Gln Lys Pro Leu Thr Glu Glu Ala Lys Asn Trp Ala Pro Gly Glu
65                  70                  75                  80
Pro Asn Asn Arg Gln Lys Asp Glu Asp Cys Val Glu Ile Tyr Ile Lys
                85                  90                  95
Arg Glu Lys Asp Val Gly Met Trp Asn Asp Glu Arg Cys Ser Lys Lys
            100                 105                 110
Lys Leu Ala Leu Cys Tyr Thr Ala Ala Cys Thr Asn Thr Ser Cys Ser
            115                 120                 125
Gly His Gly Glu Cys Val Glu Thr Ile Asn Asn Tyr Thr Cys Lys Cys
        130                 135                 140
Asp Pro Gly Phe Ser Gly Leu Lys Cys Glu Gln Ile Val Asn Cys Thr
145                 150                 155                 160
Ala Leu Glu Ser Pro Glu His Gly Ser Leu Val Cys Ser His Pro Leu
                165                 170                 175
Gly Asn Phe Ser Tyr Asn Ser Ser Cys Ser Ile Ser Cys Asp Arg Gly
            180                 185                 190
Tyr Leu Pro Ser Ser Met Glu Thr Met Gln Cys Met Ser Ser Gly Glu
            195                 200                 205
Trp Ser Ala Pro Ile Pro Ala Cys Asn Val Val Glu Cys Asp Ala Val
        210                 215                 220
Thr Asn Pro Ala Asn Gly Phe Val Glu Cys Phe Gln Asn Pro Gly Ser
225                 230                 235                 240
Phe Pro Trp Asn Thr Thr Cys Thr Phe Asp Cys Glu Gly Gly Phe Glu
                245                 250                 255
Leu Met Gly Ala Gln Ser Leu Gln Cys Thr Ser Ser Gly Asn Trp Asp
            260                 265                 270
Asn Glu Lys Pro Thr Cys Lys Ala Val Thr Arg Ser
            275                 280

<210> SEQ ID NO 8
<211> LENGTH: 282
<212> TYPE: PRT
<213> ORGANISM: Homo sapiens

<400> SEQUENCE: 8

Trp Ser Tyr Asn Thr Ser Thr Glu Ala Met Thr Tyr Asp Glu Ala Ser
1               5                   10                  15
Ala Tyr Cys Gln Gln Arg Tyr Thr His Leu Val Ala Ile Gln Asn Lys
            20                  25                  30
Glu Glu Ile Glu Tyr Leu Asn Ser Ile Leu Ser Tyr Ser Pro Ser Tyr
        35                  40                  45
Tyr Trp Ile Gly Ile Arg Lys Val Asn Asn Val Trp Val Trp Val Gly
        50                  55                  60
Thr Gln Lys Pro Leu Thr Glu Glu Ala Lys Asn Trp Ala Pro Gly Glu
65                  70                  75                  80
Pro Asn Asn Arg Gln Lys Asp Glu Asp Cys Val Glu Ile Tyr Ile Lys
                85                  90                  95
Arg Glu Lys Asp Val Gly Met Trp Asn Asp Glu Arg Cys Ser Lys Lys
            100                 105                 110
Lys Leu Ala Leu Cys Tyr Thr Ala Ala Cys Thr Asn Thr Ser Cys Ser
```

```
                115                 120                 125
Gly His Gly Glu Cys Val Glu Thr Ile Asn Asn Tyr Thr Cys Lys Cys
            130                 135                 140

Asp Pro Gly Phe Ser Gly Leu Lys Cys Glu Gln Ile Val Asn Cys Thr
145                 150                 155                 160

Ala Leu Glu Ser Pro Glu His Gly Ser Leu Val Cys Ser His Pro Leu
                165                 170                 175

Gly Asn Phe Ser Tyr Asn Ser Ser Cys Ser Ile Ser Cys Asp Arg Gly
            180                 185                 190

Tyr Leu Pro Ser Ser Met Glu Thr Met Gln Cys Met Ser Ser Gly Glu
                195                 200                 205

Trp Ser Ala Pro Ile Pro Ala Cys Asn Val Val Glu Cys Asp Ala Val
            210                 215                 220

Thr Asn Pro Ala Asn Gly Phe Val Glu Cys Phe Gln Asn Pro Gly Ser
225                 230                 235                 240

Phe Pro Trp Asn Thr Thr Cys Thr Phe Asp Cys Glu Glu Gly Phe Glu
                245                 250                 255

Leu Met Gly Ala Gln Ser Leu Gln Cys Thr Ser Ser Gly Asn Trp Asp
            260                 265                 270

Asn Glu Lys Pro Thr Cys Lys Ala Val Thr
                275                 280

<210> SEQ ID NO 9
<211> LENGTH: 485
<212> TYPE: PRT
<213> ORGANISM: Bovine

<400> SEQUENCE: 9

Met Ile Val Ser Gln Tyr Leu Ser Ala Leu Thr Phe Val Leu Leu Leu
 1               5                  10                  15

Phe Lys Glu Ser Arg Thr Trp Ser Tyr His Ala Ser Thr Glu Met Met
            20                  25                  30

Thr Phe Glu Glu Ala Arg Asp Tyr Cys Gln Lys Thr Tyr Thr Ala Leu
        35                  40                  45

Val Ala Ile Gln Asn Gln Glu Glu Ile Glu Tyr Leu Asn Ser Thr Phe
50                  55                  60

Ser Tyr Ser Pro Ser Tyr Tyr Trp Ile Gly Ile Arg Lys Ile Asn Gly
65                  70                  75                  80

Thr Trp Thr Trp Ile Gly Thr Asn Lys Ser Leu Thr Lys Glu Ala Thr
                85                  90                  95

Asn Trp Ala Pro Gly Glu Pro Asn Asn Lys Gln Ser Asp Glu Asp Cys
            100                 105                 110

Val Glu Ile Tyr Ile Lys Arg Glu Lys Asp Ser Gly Lys Trp Asn Asp
        115                 120                 125

Glu Lys Cys Thr Lys Gln Lys Leu Ala Leu Cys Tyr Lys Ala Ala Cys
130                 135                 140

Asn Pro Thr Pro Cys Gly Ser His Gly Glu Cys Val Glu Thr Ile Asn
145                 150                 155                 160

Asn Tyr Thr Cys Gln Cys His Pro Gly Phe Lys Gly Leu Lys Cys Glu
                165                 170                 175

Gln Val Thr Cys Pro Ala Gln Lys His Pro Glu His Gly His Leu
            180                 185                 190

Val Cys Asn Pro Leu Gly Lys Phe Thr Tyr Asn Ser Ser Cys Ser Ile
        195                 200                 205

Ser Cys Ala Glu Gly Tyr Leu Pro Ser Ser Thr Glu Ala Thr Arg Cys
```

```
                    210             215             220
Met Ser Ser Gly Glu Trp Ser Thr Pro Leu Pro Lys Cys Asn Val Val
225                 230             235             240

Lys Cys Asp Ala Leu Ser Asn Leu Asp Asn Gly Val Val Asn Cys Ser
            245             250             255

Pro Asn His Gly Ser Leu Pro Trp Asn Thr Thr Cys Thr Phe Glu Cys
        260             265             270

Gln Glu Gly Tyr Lys Leu Thr Gly Pro Gln His Leu Gln Cys Thr Ser
    275             280             285

Ser Gly Ile Trp Asp Asn Lys Gln Pro Thr Cys Lys Ala Val Ser Cys
290             295             300

Ala Ala Ile Ser His Pro Gln Asn Gly Thr Val Asn Cys Ser His Ser
305             310             315             320

Val Val Gly Asp Phe Ala Phe Lys Ser Ser Cys His Phe Thr Cys Ala
                325             330             335

Glu Gly Phe Thr Leu Gln Gly Pro Thr Gln Val Glu Cys Thr Ala Gln
            340             345             350

Gly Gln Trp Thr Gln Arg Val Pro Val Cys Glu Val Val Arg Cys Ser
        355             360             365

Arg Leu Asp Val Ser Gly Lys Leu Asn Met Asn Cys Ser Gly Glu Pro
    370             375             380

Val Leu Gly Thr Glu Cys Thr Phe Ala Cys Pro Glu Arg Trp Thr Leu
385             390             395             400

Asn Gly Ser Val Val Leu Thr Cys Gly Ala Thr Gly His Trp Ser Gly
                405             410             415

Met Leu Pro Thr Cys Glu Ala Pro Thr Val Ser Gln Thr Pro Leu Ala
            420             425             430

Val Gly Leu Ser Thr Ala Gly Val Ser Leu Val Thr Ile Pro Ser Phe
        435             440             445

Leu Phe Trp Leu Leu Lys Arg Leu Gln Lys Lys Ala Lys Lys Phe Ser
    450             455             460

Pro Ala Ser Ser Cys Ser Ser Leu Lys Ser Asn Gly Cys Tyr Ser Thr
465             470             475             480

Pro Ser Lys Leu Ile
            485

<210> SEQ ID NO 10
<211> LENGTH: 463
<212> TYPE: PRT
<213> ORGANISM: Bovine

<400> SEQUENCE: 10

Trp Ser Tyr His Ala Ser Thr Glu Met Met Thr Phe Glu Glu Ala Arg
1               5                   10                  15

Asp Tyr Cys Gln Lys Thr Tyr Thr Ala Leu Val Ala Ile Gln Asn Gln
            20                  25                  30

Glu Glu Ile Glu Tyr Leu Asn Ser Thr Phe Ser Tyr Ser Pro Ser Tyr
        35                  40                  45

Tyr Trp Ile Gly Ile Arg Lys Ile Asn Gly Thr Trp Thr Trp Ile Gly
    50                  55                  60

Thr Asn Lys Ser Leu Thr Lys Glu Ala Thr Asn Trp Ala Pro Gly Glu
65                  70                  75                  80

Pro Asn Asn Lys Gln Ser Asp Glu Asp Cys Val Glu Ile Tyr Ile Lys
                85                  90                  95

Arg Glu Lys Asp Ser Gly Lys Trp Asn Asp Glu Lys Cys Thr Lys Gln
```

```
                100                 105                 110
Lys Leu Ala Leu Cys Tyr Lys Ala Ala Cys Asn Pro Thr Pro Cys Gly
            115                 120                 125

Ser His Gly Glu Cys Val Glu Thr Ile Asn Asn Tyr Thr Cys Gln Cys
    130                 135                 140

His Pro Gly Phe Lys Gly Leu Lys Cys Glu Gln Val Val Thr Cys Pro
145                 150                 155                 160

Ala Gln Lys His Pro Glu His Gly His Leu Val Cys Asn Pro Leu Gly
                165                 170                 175

Lys Phe Thr Tyr Asn Ser Ser Cys Ser Ile Ser Cys Ala Glu Gly Tyr
            180                 185                 190

Leu Pro Ser Ser Thr Glu Ala Thr Arg Cys Met Ser Ser Gly Glu Trp
        195                 200                 205

Ser Thr Pro Leu Pro Lys Cys Asn Val Val Lys Cys Asp Ala Leu Ser
    210                 215                 220

Asn Leu Asp Asn Gly Val Val Asn Cys Ser Pro Asn His Gly Ser Leu
225                 230                 235                 240

Pro Trp Asn Thr Thr Cys Thr Phe Glu Cys Gln Glu Gly Tyr Lys Leu
                245                 250                 255

Thr Gly Pro Gln His Leu Gln Cys Thr Ser Ser Gly Ile Trp Asp Asn
            260                 265                 270

Lys Gln Pro Thr Cys Lys Ala Val Ser Cys Ala Ala Ile Ser His Pro
        275                 280                 285

Gln Asn Gly Thr Val Asn Cys Ser His Ser Val Val Gly Asp Phe Ala
    290                 295                 300

Phe Lys Ser Ser Cys His Phe Thr Cys Ala Glu Gly Phe Thr Leu Gln
305                 310                 315                 320

Gly Pro Thr Gln Val Glu Cys Thr Ala Gln Gly Gln Trp Thr Gln Arg
                325                 330                 335

Val Pro Val Cys Glu Val Val Arg Cys Ser Arg Leu Asp Val Ser Gly
            340                 345                 350

Lys Leu Asn Met Asn Cys Ser Gly Glu Pro Val Leu Gly Thr Glu Cys
        355                 360                 365

Thr Phe Ala Cys Pro Glu Arg Trp Thr Leu Asn Gly Ser Val Val Leu
    370                 375                 380

Thr Cys Gly Ala Thr Gly His Trp Ser Gly Met Leu Pro Thr Cys Glu
385                 390                 395                 400

Ala Pro Thr Val Ser Gln Thr Pro Leu Ala Val Gly Leu Ser Thr Ala
                405                 410                 415

Gly Val Ser Leu Val Thr Ile Pro Ser Phe Leu Phe Trp Leu Leu Lys
            420                 425                 430

Arg Leu Gln Lys Lys Ala Lys Lys Phe Ser Pro Ala Ser Ser Cys Ser
        435                 440                 445

Ser Leu Lys Ser Asn Gly Cys Tyr Ser Thr Pro Ser Lys Leu Ile
    450                 455                 460

<210> SEQ ID NO 11
<211> LENGTH: 408
<212> TYPE: PRT
<213> ORGANISM: Bovine

<400> SEQUENCE: 11

Trp Ser Tyr His Ala Ser Thr Glu Met Met Thr Phe Glu Glu Ala Arg
1               5                   10                  15

Asp Tyr Cys Gln Lys Thr Tyr Thr Ala Leu Val Ala Ile Gln Asn Gln
```

```
                    20                  25                  30
Glu Glu Ile Glu Tyr Leu Asn Ser Thr Phe Ser Tyr Ser Pro Ser Tyr
                35                  40                  45
Tyr Trp Ile Gly Ile Arg Lys Ile Asn Gly Thr Trp Thr Trp Ile Gly
            50                  55                  60
Thr Asn Lys Ser Leu Thr Lys Glu Ala Thr Asn Trp Ala Pro Gly Glu
65                  70                  75                  80
Pro Asn Asn Lys Gln Ser Asp Glu Asp Cys Val Glu Ile Tyr Ile Lys
                85                  90                  95
Arg Glu Lys Asp Ser Gly Lys Trp Asn Asp Glu Lys Cys Thr Lys Gln
                100                 105                 110
Lys Leu Ala Leu Cys Tyr Lys Ala Ala Cys Asn Pro Thr Pro Cys Gly
                115                 120                 125
Ser His Gly Glu Cys Val Glu Thr Ile Asn Asn Tyr Thr Cys Gln Cys
                130                 135                 140
His Pro Gly Phe Lys Gly Leu Lys Cys Glu Gln Val Val Thr Cys Pro
145                 150                 155                 160
Ala Gln Lys His Pro Glu His Gly His Leu Val Cys Asn Pro Leu Gly
                165                 170                 175
Lys Phe Thr Tyr Asn Ser Ser Cys Ser Ile Ser Cys Ala Glu Gly Tyr
                180                 185                 190
Leu Pro Ser Ser Thr Glu Ala Thr Arg Cys Met Ser Ser Gly Glu Trp
                195                 200                 205
Ser Thr Pro Leu Pro Lys Cys Asn Val Val Lys Cys Asp Ala Leu Ser
                210                 215                 220
Asn Leu Asp Asn Gly Val Val Asn Cys Ser Pro Asn His Gly Ser Leu
225                 230                 235                 240
Pro Trp Asn Thr Thr Cys Thr Phe Glu Cys Gln Glu Gly Tyr Lys Leu
                245                 250                 255
Thr Gly Pro Gln His Leu Gln Cys Thr Ser Ser Gly Ile Trp Asp Asn
                260                 265                 270
Lys Gln Pro Thr Cys Lys Ala Val Ser Cys Ala Ala Ile Ser His Pro
                275                 280                 285
Gln Asn Gly Thr Val Asn Cys Ser His Ser Val Val Gly Asp Phe Ala
                290                 295                 300
Phe Lys Ser Ser Cys His Phe Thr Cys Ala Glu Gly Phe Thr Leu Gln
305                 310                 315                 320
Gly Pro Thr Gln Val Glu Cys Thr Ala Gln Gly Gln Trp Thr Gln Arg
                325                 330                 335
Val Pro Val Cys Glu Val Val Arg Cys Ser Arg Leu Asp Val Ser Gly
                340                 345                 350
Lys Leu Asn Met Asn Cys Ser Gly Glu Pro Val Leu Gly Thr Glu Cys
                355                 360                 365
Thr Phe Ala Cys Pro Glu Arg Trp Thr Leu Asn Gly Ser Val Val Leu
                370                 375                 380
Thr Cys Gly Ala Thr Gly His Trp Ser Gly Met Leu Pro Thr Cys Glu
385                 390                 395                 400
Ala Pro Thr Val Ser Gln Thr Pro
                405

<210> SEQ ID NO 12
<211> LENGTH: 549
<212> TYPE: PRT
<213> ORGANISM: Rattus norvegicus
```

-continued

<400> SEQUENCE: 12

```
Met Asn Ala Ser Cys Phe Leu Ser Ala Leu Thr Phe Val Leu Leu Ile
 1               5                  10                  15

Gly Lys Ser Ile Ala Trp Tyr Tyr Asn Ala Ser Ser Glu Leu Met Thr
             20                  25                  30

Tyr Asp Glu Ala Ser Ala Tyr Cys Gln Arg Asp Tyr Thr His Leu Val
         35                  40                  45

Ala Ile Gln Asn Lys Glu Glu Ile Asn Tyr Leu Asn Ser Thr Leu Arg
     50                  55                  60

Tyr Ser Pro Ser Tyr Tyr Trp Ile Gly Ile Arg Lys Val Asn Asn Val
 65                  70                  75                  80

Trp Ile Trp Val Gly Thr Gln Lys Pro Leu Thr Glu Glu Ala Lys Asn
                 85                  90                  95

Trp Ala Pro Gly Glu Pro Asn Asn Lys Gln Arg Asn Glu Asp Cys Val
            100                 105                 110

Glu Ile Tyr Ile Gln Arg Pro Lys Asp Ser Gly Met Trp Asn Asp Glu
        115                 120                 125

Arg Cys Asp Lys Lys Lys Leu Ala Leu Cys Tyr Thr Ala Ser Cys Thr
130                 135                 140

Asn Thr Ser Cys Ser Gly His Gly Glu Cys Val Glu Thr Ile Asn Ser
145                 150                 155                 160

Tyr Thr Cys Lys Cys His Pro Gly Phe Leu Gly Pro Lys Cys Asp Gln
                165                 170                 175

Val Val Thr Cys Gln Glu Gln Glu Tyr Pro Asp His Gly Ser Leu Asn
            180                 185                 190

Cys Thr His Pro Phe Gly Leu Phe Ser Tyr Asn Ser Ser Cys Ser Phe
        195                 200                 205

Ser Cys Glu Arg Gly Tyr Val Pro Ser Ser Met Glu Thr Thr Val Arg
210                 215                 220

Cys Thr Ser Ser Gly Glu Trp Ser Ala Pro Ala Pro Ala Cys His Val
225                 230                 235                 240

Val Glu Cys Lys Ala Leu Thr Gln Pro Ala His Gly Val Arg Lys Cys
                245                 250                 255

Ser Ser Asn Pro Gly Ser Tyr Pro Trp Asn Thr Thr Cys Thr Phe Asp
            260                 265                 270

Cys Glu Glu Gly Tyr Arg Arg Val Gly Ala Gln Asn Leu Gln Cys Thr
        275                 280                 285

Ser Ser Gly Val Trp Asp Asn Glu Lys Pro Ser Cys Lys Ala Val Thr
290                 295                 300

Cys Asp Ala Ile Pro Arg Pro Gln Asn Gly Ser Val Ser Cys Ser Asn
305                 310                 315                 320

Ser Thr Ala Gly Ala Leu Ala Phe Lys Ser Ser Cys Asn Phe Thr Cys
                325                 330                 335

Glu His Ser Phe Thr Leu Gln Gly Pro Ala Gln Val Glu Cys Ser Ala
            340                 345                 350

Gln Gly Gln Trp Thr Pro Gln Ile Pro Val Cys Lys Ala Ser Gln Cys
        355                 360                 365

Glu Ala Leu Ser Ala Pro Gln Arg Gly His Met Lys Cys Leu Pro Ser
370                 375                 380

Ala Ser Ala Pro Phe Gln Ser Gly Ser Ser Cys Lys Phe Ser Cys Asp
385                 390                 395                 400

Glu Gly Phe Glu Leu Lys Gly Ser Arg Arg Leu Gln Cys Gly Pro Arg
                405                 410                 415
```

```
Gly Glu Trp Asp Ser Glu Lys Pro Thr Cys Ala Gly Val Gln Cys Ser
            420                 425                 430

Ser Leu Asp Leu Pro Gly Lys Met Asn Met Ser Cys Ser Gly Pro Ala
        435                 440                 445

Val Phe Gly Thr Val Cys Glu Phe Thr Cys Pro Glu Gly Trp Thr Leu
    450                 455                 460

Asn Gly Ser Ser Ile Leu Thr Cys Gly Ala Thr Gly Arg Trp Ser Ala
465                 470                 475                 480

Met Leu Pro Thr Cys Glu Ala Pro Ala Asn Pro Arg Pro Leu Val
                485                 490                 495

Val Ala Leu Ser Val Ala Ala Thr Ser Leu Leu Thr Leu Ser Ser Leu
            500                 505                 510

Ile Tyr Val Leu Lys Arg Phe Phe Trp Lys Lys Ala Lys Lys Phe Val
        515                 520                 525

Pro Ala Ser Ser Cys Gln Ser Leu Gln Ser Phe Glu Asn Tyr Gln Gly
    530                 535                 540

Pro Ser Tyr Ile Ile
545

<210> SEQ ID NO 13
<211> LENGTH: 528
<212> TYPE: PRT
<213> ORGANISM: Rattus norvegicus

<400> SEQUENCE: 13

Trp Tyr Tyr Asn Ala Ser Ser Glu Leu Met Thr Tyr Asp Glu Ala Ser
  1               5                  10                  15

Ala Tyr Cys Gln Arg Asp Tyr Thr His Leu Val Ala Ile Gln Asn Lys
             20                  25                  30

Glu Glu Ile Asn Tyr Leu Asn Ser Thr Leu Arg Tyr Ser Pro Ser Tyr
         35                  40                  45

Tyr Trp Ile Gly Ile Arg Lys Val Asn Asn Val Trp Ile Trp Val Gly
     50                  55                  60

Thr Gln Lys Pro Leu Thr Glu Glu Ala Lys Asn Trp Ala Pro Gly Glu
 65                  70                  75                  80

Pro Asn Asn Lys Gln Arg Asn Glu Asp Cys Val Glu Ile Tyr Ile Gln
                 85                  90                  95

Arg Pro Lys Asp Ser Gly Met Trp Asn Asp Glu Arg Cys Asp Lys Lys
            100                 105                 110

Lys Leu Ala Leu Cys Tyr Thr Ala Ser Cys Thr Asn Thr Ser Cys Ser
        115                 120                 125

Gly His Gly Glu Cys Val Glu Thr Ile Asn Ser Tyr Thr Cys Lys Cys
    130                 135                 140

His Pro Gly Phe Leu Gly Pro Lys Cys Asp Gln Val Val Thr Cys Gln
145                 150                 155                 160

Glu Gln Glu Tyr Pro Asp His Gly Ser Leu Asn Cys Thr His Pro Phe
                165                 170                 175

Gly Leu Phe Ser Tyr Asn Ser Ser Cys Ser Phe Ser Cys Glu Arg Gly
            180                 185                 190

Tyr Val Pro Ser Ser Met Glu Thr Thr Val Arg Cys Thr Ser Ser Gly
        195                 200                 205

Glu Trp Ser Ala Pro Ala Pro Ala Cys His Val Val Glu Cys Lys Ala
    210                 215                 220

Leu Thr Gln Pro Ala His Gly Val Arg Lys Cys Ser Ser Asn Pro Gly
225                 230                 235                 240
```

-continued

Ser Tyr Pro Trp Asn Thr Thr Cys Thr Phe Asp Cys Glu Glu Gly Tyr
            245                 250                 255

Arg Arg Val Gly Ala Gln Asn Leu Gln Cys Thr Ser Ser Gly Val Trp
        260                 265                 270

Asp Asn Glu Lys Pro Ser Cys Lys Ala Val Thr Cys Asp Ala Ile Pro
    275                 280                 285

Arg Pro Gln Asn Gly Ser Val Ser Cys Ser Asn Ser Thr Ala Gly Ala
290                 295                 300

Leu Ala Phe Lys Ser Ser Cys Asn Phe Thr Cys Glu His Ser Phe Thr
305                 310                 315                 320

Leu Gln Gly Pro Ala Gln Val Glu Cys Ser Ala Gln Gly Gln Trp Thr
            325                 330                 335

Pro Gln Ile Pro Val Cys Lys Ala Ser Gln Cys Glu Ala Leu Ser Ala
        340                 345                 350

Pro Gln Arg Gly His Met Lys Cys Leu Pro Ser Ala Ser Ala Pro Phe
    355                 360                 365

Gln Ser Gly Ser Ser Cys Lys Phe Ser Cys Asp Glu Gly Phe Glu Leu
370                 375                 380

Lys Gly Ser Arg Arg Leu Gln Cys Gly Pro Arg Gly Glu Trp Asp Ser
385                 390                 395                 400

Glu Lys Pro Thr Cys Ala Gly Val Gln Cys Ser Ser Leu Asp Leu Pro
            405                 410                 415

Gly Lys Met Asn Met Ser Cys Ser Gly Pro Ala Val Phe Gly Thr Val
        420                 425                 430

Cys Glu Phe Thr Cys Pro Glu Gly Trp Thr Leu Asn Gly Ser Ser Ile
    435                 440                 445

Leu Thr Cys Gly Ala Thr Gly Arg Trp Ser Ala Met Leu Pro Thr Cys
450                 455                 460

Glu Ala Pro Ala Asn Pro Pro Arg Pro Leu Val Val Ala Leu Ser Val
465                 470                 475                 480

Ala Ala Thr Ser Leu Leu Thr Leu Ser Ser Leu Ile Tyr Val Leu Lys
            485                 490                 495

Arg Phe Phe Trp Lys Lys Ala Lys Lys Phe Val Pro Ala Ser Ser Cys
        500                 505                 510

Gln Ser Leu Gln Ser Phe Glu Asn Tyr Gln Gly Pro Ser Tyr Ile Ile
    515                 520                 525

<210> SEQ ID NO 14
<211> LENGTH: 474
<212> TYPE: PRT
<213> ORGANISM: Rattus norvegicus

<400> SEQUENCE: 14

Ala Trp Tyr Tyr Asn Ala Ser Ser Glu Leu Met Thr Tyr Asp Glu Ala
1               5                   10                  15

Ser Ala Tyr Cys Gln Arg Asp Tyr Thr His Leu Val Ala Ile Gln Asn
            20                  25                  30

Lys Glu Glu Ile Asn Tyr Leu Asn Ser Thr Leu Arg Tyr Ser Pro Ser
        35                  40                  45

Tyr Tyr Trp Ile Gly Ile Arg Lys Val Asn Asn Val Trp Ile Trp Val
    50                  55                  60

Gly Thr Gln Lys Pro Leu Thr Glu Glu Ala Lys Asn Trp Ala Pro Gly
65                  70                  75                  80

Glu Pro Asn Asn Lys Gln Arg Asn Glu Asp Cys Val Glu Ile Tyr Ile
            85                  90                  95

```
Gln Arg Pro Lys Asp Ser Gly Met Trp Asn Asp Glu Arg Cys Asp Lys
                100                 105                 110

Lys Lys Leu Ala Leu Cys Tyr Thr Ala Ser Cys Thr Asn Thr Ser Cys
            115                 120                 125

Ser Gly His Gly Glu Cys Val Glu Thr Ile Asn Ser Tyr Thr Cys Lys
        130                 135                 140

Cys His Pro Gly Phe Leu Gly Pro Lys Cys Asp Gln Val Val Thr Cys
145                 150                 155                 160

Gln Glu Gln Glu Tyr Pro Asp His Gly Ser Leu Asn Cys Thr His Pro
                165                 170                 175

Phe Gly Leu Phe Ser Tyr Asn Ser Ser Cys Ser Phe Ser Cys Glu Arg
            180                 185                 190

Gly Tyr Val Pro Ser Ser Met Glu Thr Thr Val Arg Cys Thr Ser Ser
        195                 200                 205

Gly Glu Trp Ser Ala Pro Ala Pro Ala Cys His Val Val Glu Cys Lys
    210                 215                 220

Ala Leu Thr Gln Pro Ala His Gly Val Arg Lys Cys Ser Ser Asn Pro
225                 230                 235                 240

Gly Ser Tyr Pro Trp Asn Thr Thr Cys Thr Phe Asp Cys Glu Glu Gly
                245                 250                 255

Tyr Arg Arg Val Gly Ala Gln Asn Leu Gln Cys Thr Ser Ser Gly Val
            260                 265                 270

Trp Asp Asn Glu Lys Pro Ser Cys Lys Ala Val Thr Cys Asp Ala Ile
        275                 280                 285

Pro Arg Pro Gln Asn Gly Ser Val Ser Cys Ser Asn Ser Thr Ala Gly
290                 295                 300

Ala Leu Ala Phe Lys Ser Ser Cys Asn Phe Thr Cys Glu His Ser Phe
305                 310                 315                 320

Thr Leu Gln Gly Pro Ala Gln Val Glu Cys Ser Ala Gln Gly Gln Trp
                325                 330                 335

Thr Pro Gln Ile Pro Val Cys Lys Ala Ser Gln Cys Glu Ala Leu Ser
            340                 345                 350

Ala Pro Gln Arg Gly His Met Lys Cys Leu Pro Ser Ala Ser Ala Pro
        355                 360                 365

Phe Gln Ser Gly Ser Ser Cys Lys Phe Ser Cys Asp Glu Gly Phe Glu
370                 375                 380

Leu Lys Gly Ser Arg Arg Leu Gln Cys Gly Pro Arg Gly Glu Trp Asp
385                 390                 395                 400

Ser Glu Lys Pro Thr Cys Ala Gly Val Gln Cys Ser Ser Leu Asp Leu
                405                 410                 415

Pro Gly Lys Met Asn Met Ser Cys Ser Gly Pro Ala Val Phe Gly Thr
            420                 425                 430

Val Cys Glu Phe Thr Cys Pro Glu Gly Trp Thr Leu Asn Gly Ser Ser
        435                 440                 445

Ile Leu Thr Cys Gly Ala Thr Gly Arg Trp Ser Ala Met Leu Pro Thr
    450                 455                 460

Cys Glu Ala Pro Ala Asn Pro Pro Arg Pro
465                 470

<210> SEQ ID NO 15
<211> LENGTH: 612
<212> TYPE: PRT
<213> ORGANISM: Mus musculus

<400> SEQUENCE: 15
```

```
Met Asn Ala Ser Arg Phe Leu Ser Ala Leu Val Phe Val Leu Leu Ala
 1               5                  10                  15
Gly Glu Ser Thr Ala Trp Tyr Tyr Asn Ala Ser Ser Glu Leu Met Thr
             20                  25                  30
Tyr Asp Glu Ala Ser Ala Tyr Cys Gln Arg Asp Tyr Thr His Leu Val
         35                  40                  45
Ala Ile Gln Asn Lys Glu Glu Ile Asn Tyr Leu Asn Ser Asn Leu Lys
     50                  55                  60
His Ser Pro Ser Tyr Tyr Trp Ile Gly Ile Arg Lys Val Asn Asn Val
 65                  70                  75                  80
Trp Ile Trp Val Gly Thr Gly Lys Pro Leu Thr Glu Glu Ala Gln Asn
                 85                  90                  95
Trp Ala Pro Gly Glu Pro Asn Asn Lys Gln Arg Asn Glu Asp Cys Val
            100                 105                 110
Glu Ile Tyr Ile Gln Arg Thr Lys Asp Ser Gly Met Trp Asn Asp Glu
        115                 120                 125
Arg Cys Asn Lys Lys Lys Leu Ala Leu Cys Tyr Thr Ala Ser Cys Thr
    130                 135                 140
Asn Ala Ser Cys Ser Gly His Gly Glu Cys Ile Glu Thr Ile Asn Ser
145                 150                 155                 160
Tyr Thr Cys Lys Cys His Pro Gly Phe Leu Gly Pro Asn Cys Glu Gln
                165                 170                 175
Ala Val Thr Cys Lys Pro Gln Glu His Pro Asp Tyr Gly Ser Leu Asn
            180                 185                 190
Cys Ser His Pro Phe Gly Pro Phe Ser Tyr Asn Ser Ser Cys Ser Phe
        195                 200                 205
Gly Cys Lys Arg Gly Tyr Leu Pro Ser Ser Met Glu Thr Thr Val Arg
    210                 215                 220
Cys Thr Ser Ser Gly Glu Trp Ser Ala Pro Ala Pro Ala Cys His Val
225                 230                 235                 240
Val Glu Cys Glu Ala Leu Thr His Pro Ala His Gly Ile Arg Lys Cys
                245                 250                 255
Ser Ser Asn Pro Gly Ser Tyr Pro Trp Asn Thr Thr Cys Thr Phe Asp
            260                 265                 270
Cys Val Glu Gly Tyr Arg Arg Val Gly Ala Gln Asn Leu Gln Cys Thr
        275                 280                 285
Ser Ser Gly Ile Trp Asp Asn Glu Thr Pro Ser Cys Lys Ala Val Thr
    290                 295                 300
Cys Asp Ala Ile Pro Gln Pro Gln Asn Gly Phe Val Ser Cys Ser His
305                 310                 315                 320
Ser Thr Ala Gly Glu Leu Ala Phe Lys Ser Ser Cys Asn Phe Thr Cys
                325                 330                 335
Glu Gln Ser Phe Thr Leu Gln Gly Pro Ala Gln Val Glu Cys Ser Ala
            340                 345                 350
Gln Gly Gln Trp Thr Pro Gln Ile Pro Val Cys Lys Ala Val Gln Cys
        355                 360                 365
Glu Ala Leu Ser Ala Pro Gln Gln Gly Asn Met Lys Cys Leu Pro Ser
    370                 375                 380
Ala Ser Gly Pro Phe Gln Asn Gly Ser Ser Cys Glu Phe Ser Cys Glu
385                 390                 395                 400
Glu Gly Phe Glu Leu Lys Gly Ser Arg Arg Leu Gln Cys Gly Pro Arg
                405                 410                 415
Gly Glu Trp Asp Ser Lys Lys Pro Thr Cys Ser Ala Val Lys Cys Asp
            420                 425                 430
```

Asp Val Pro Arg Pro Gln Asn Gly Val Met Glu Cys Ala His Ala Thr
    435                 440                 445

Thr Gly Glu Phe Thr Tyr Lys Ser Ser Cys Ala Phe Gln Cys Asn Glu
    450                 455                 460

Gly Phe Ser Leu His Gly Ser Ala Gln Leu Glu Cys Thr Ser Gln Gly
465                 470                 475                 480

Lys Trp Thr Gln Glu Val Pro Ser Cys Gln Val Val Gln Cys Pro Ser
                485                 490                 495

Leu Asp Val Pro Gly Lys Met Asn Met Ser Cys Ser Gly Thr Ala Val
            500                 505                 510

Phe Gly Thr Val Cys Glu Phe Thr Cys Pro Asp Asp Trp Thr Leu Asn
        515                 520                 525

Gly Ser Ala Val Leu Thr Cys Gly Ala Thr Gly Arg Trp Ser Gly Met
    530                 535                 540

Pro Pro Thr Cys Glu Ala Pro Val Ser Pro Thr Arg Pro Leu Val Val
545                 550                 555                 560

Ala Leu Ser Ala Ala Gly Thr Ser Leu Leu Thr Ser Ser Leu Leu
                565                 570                 575

Tyr Leu Leu Met Arg Tyr Phe Arg Lys Lys Ala Lys Lys Phe Val Pro
            580                 585                 590

Ala Ser Ser Cys Gln Ser Leu Gln Ser Phe Glu Asn Tyr His Val Pro
        595                 600                 605

Ser Tyr Asn Val
    610

<210> SEQ ID NO 16
<211> LENGTH: 591
<212> TYPE: PRT
<213> ORGANISM: Mus musculus

<400> SEQUENCE: 16

Trp Tyr Tyr Asn Ala Ser Ser Glu Leu Met Thr Tyr Asp Glu Ala Ser
1               5                   10                  15

Ala Tyr Cys Gln Arg Asp Tyr Thr His Leu Val Ala Ile Gln Asn Lys
            20                  25                  30

Glu Glu Ile Asn Tyr Leu Asn Ser Asn Leu Lys His Ser Pro Ser Tyr
        35                  40                  45

Tyr Trp Ile Gly Ile Arg Lys Val Asn Asn Val Trp Ile Trp Val Gly
    50                  55                  60

Thr Gly Lys Pro Leu Thr Glu Glu Ala Gln Asn Trp Ala Pro Gly Glu
65                  70                  75                  80

Pro Asn Asn Lys Gln Arg Asn Glu Asp Cys Val Glu Ile Tyr Ile Gln
                85                  90                  95

Arg Thr Lys Asp Ser Gly Met Trp Asn Asp Glu Arg Cys Asn Lys Lys
            100                 105                 110

Lys Leu Ala Leu Cys Tyr Thr Ala Ser Cys Thr Asn Ala Ser Cys Ser
        115                 120                 125

Gly His Gly Glu Cys Ile Glu Thr Ile Asn Ser Tyr Thr Cys Lys Cys
    130                 135                 140

His Pro Gly Phe Leu Gly Pro Asn Cys Glu Gln Ala Val Thr Cys Lys
145                 150                 155                 160

Pro Gln Glu His Pro Asp Tyr Gly Ser Leu Asn Cys Ser His Pro Phe
                165                 170                 175

Gly Pro Phe Ser Tyr Asn Ser Ser Cys Ser Phe Gly Cys Lys Arg Gly
            180                 185                 190

Tyr Leu Pro Ser Ser Met Glu Thr Thr Val Arg Cys Thr Ser Ser Gly
            195                 200                 205

Glu Trp Ser Ala Pro Ala Pro Ala Cys His Val Val Glu Cys Glu Ala
            210                 215                 220

Leu Thr His Pro Ala His Gly Ile Arg Lys Cys Ser Ser Asn Pro Gly
225                 230                 235                 240

Ser Tyr Pro Trp Asn Thr Thr Cys Thr Phe Asp Cys Val Glu Gly Tyr
            245                 250                 255

Arg Arg Val Gly Ala Gln Asn Leu Gln Cys Thr Ser Ser Gly Ile Trp
            260                 265                 270

Asp Asn Glu Thr Pro Ser Cys Lys Ala Val Thr Cys Asp Ala Ile Pro
            275                 280                 285

Gln Pro Gln Asn Gly Phe Val Ser Cys Ser His Ser Thr Ala Gly Glu
            290                 295                 300

Leu Ala Phe Lys Ser Ser Cys Asn Phe Thr Cys Glu Gln Ser Phe Thr
305                 310                 315                 320

Leu Gln Gly Pro Ala Gln Val Glu Cys Ser Ala Gln Gly Gln Trp Thr
            325                 330                 335

Pro Gln Ile Pro Val Cys Lys Ala Val Gln Cys Glu Ala Leu Ser Ala
            340                 345                 350

Pro Gln Gln Gly Asn Met Lys Cys Leu Pro Ser Ala Ser Gly Pro Phe
            355                 360                 365

Gln Asn Gly Ser Ser Cys Glu Phe Ser Cys Glu Glu Gly Phe Glu Leu
            370                 375                 380

Lys Gly Ser Arg Arg Leu Gln Cys Gly Pro Arg Gly Glu Trp Asp Ser
385                 390                 395                 400

Lys Lys Pro Thr Cys Ser Ala Val Lys Cys Asp Asp Val Pro Arg Pro
            405                 410                 415

Gln Asn Gly Val Met Glu Cys Ala His Ala Thr Thr Gly Glu Phe Thr
            420                 425                 430

Tyr Lys Ser Ser Cys Ala Phe Gln Cys Asn Glu Gly Phe Ser Leu His
            435                 440                 445

Gly Ser Ala Gln Leu Glu Cys Thr Ser Gln Gly Lys Trp Thr Gln Glu
            450                 455                 460

Val Pro Ser Cys Gln Val Val Gln Cys Pro Ser Leu Asp Val Pro Gly
465                 470                 475                 480

Lys Met Asn Met Ser Cys Ser Gly Thr Ala Val Phe Gly Thr Val Cys
            485                 490                 495

Glu Phe Thr Cys Pro Asp Asp Trp Thr Leu Asn Gly Ser Ala Val Leu
            500                 505                 510

Thr Cys Gly Ala Thr Gly Arg Trp Ser Gly Met Pro Pro Thr Cys Glu
            515                 520                 525

Ala Pro Val Ser Pro Thr Arg Pro Leu Val Val Ala Leu Ser Ala Ala
530                 535                 540

Gly Thr Ser Leu Leu Thr Ser Ser Leu Leu Tyr Leu Leu Met Arg
545                 550                 555                 560

Tyr Phe Arg Lys Lys Ala Lys Lys Phe Val Pro Ala Ser Ser Cys Gln
            565                 570                 575

Ser Leu Gln Ser Phe Glu Asn Tyr His Val Pro Ser Tyr Asn Val
            580                 585                 590

<210> SEQ ID NO 17
<211> LENGTH: 536
<212> TYPE: PRT

<213> ORGANISM: Mus musculus

<400> SEQUENCE: 17

```
Trp Tyr Tyr Asn Ala Ser Ser Glu Leu Met Thr Tyr Asp Glu Ala Ser
  1               5                  10                  15

Ala Tyr Cys Gln Arg Asp Tyr Thr His Leu Val Ala Ile Gln Asn Lys
             20                  25                  30

Glu Glu Ile Asn Tyr Leu Asn Ser Asn Leu Lys His Ser Pro Ser Tyr
         35                  40                  45

Tyr Trp Ile Gly Ile Arg Lys Val Asn Asn Val Trp Ile Trp Val Gly
     50                  55                  60

Thr Gly Lys Pro Leu Thr Glu Glu Ala Gln Asn Trp Ala Pro Gly Glu
 65                  70                  75                  80

Pro Asn Asn Lys Gln Arg Asn Glu Asp Cys Val Glu Ile Tyr Ile Gln
                 85                  90                  95

Arg Thr Lys Asp Ser Gly Met Trp Asn Asp Glu Arg Cys Asn Lys Lys
            100                 105                 110

Lys Leu Ala Leu Cys Tyr Thr Ala Ser Cys Thr Asn Ala Ser Cys Ser
        115                 120                 125

Gly His Gly Glu Cys Ile Glu Thr Ile Asn Ser Tyr Thr Cys Lys Cys
    130                 135                 140

His Pro Gly Phe Leu Gly Pro Asn Cys Glu Gln Ala Val Thr Cys Lys
145                 150                 155                 160

Pro Gln Glu His Pro Asp Tyr Gly Ser Leu Asn Cys Ser His Pro Phe
                165                 170                 175

Gly Pro Phe Ser Tyr Asn Ser Ser Cys Ser Phe Gly Cys Lys Arg Gly
            180                 185                 190

Tyr Leu Pro Ser Ser Met Glu Thr Thr Val Arg Cys Thr Ser Ser Gly
        195                 200                 205

Glu Trp Ser Ala Pro Ala Pro Ala Cys His Val Val Glu Cys Glu Ala
    210                 215                 220

Leu Thr His Pro Ala His Gly Ile Arg Lys Cys Ser Ser Asn Pro Gly
225                 230                 235                 240

Ser Tyr Pro Trp Asn Thr Thr Cys Thr Phe Asp Cys Val Glu Gly Tyr
                245                 250                 255

Arg Arg Val Gly Ala Gln Asn Leu Gln Cys Thr Ser Ser Gly Ile Trp
            260                 265                 270

Asp Asn Glu Thr Pro Ser Cys Lys Ala Val Thr Cys Asp Ala Ile Pro
        275                 280                 285

Gln Pro Gln Asn Gly Phe Val Ser Cys Ser His Ser Thr Ala Gly Glu
    290                 295                 300

Leu Ala Phe Lys Ser Ser Cys Asn Phe Thr Cys Glu Gln Ser Phe Thr
305                 310                 315                 320

Leu Gln Gly Pro Ala Gln Val Glu Cys Ser Ala Gln Gly Gln Trp Thr
                325                 330                 335

Pro Gln Ile Pro Val Cys Lys Ala Val Gln Cys Glu Ala Leu Ser Ala
            340                 345                 350

Pro Gln Gln Gly Asn Met Lys Cys Leu Pro Ser Ala Ser Gly Pro Phe
        355                 360                 365

Gln Asn Gly Ser Ser Cys Glu Phe Ser Cys Glu Glu Gly Phe Glu Leu
    370                 375                 380

Lys Gly Ser Arg Arg Leu Gln Cys Gly Pro Arg Gly Glu Trp Asp Ser
385                 390                 395                 400

Lys Lys Pro Thr Cys Ser Ala Val Lys Cys Asp Asp Val Pro Arg Pro
```

```
                    405                 410                 415
Gln Asn Gly Val Met Glu Cys Ala His Ala Thr Thr Gly Glu Phe Thr
                420                 425                 430

Tyr Lys Ser Ser Cys Ala Phe Gln Cys Asn Glu Gly Phe Ser Leu His
            435                 440                 445

Gly Ser Ala Gln Leu Glu Cys Thr Ser Gln Gly Lys Trp Thr Gln Glu
        450                 455                 460

Val Pro Ser Cys Gln Val Val Gln Cys Pro Ser Leu Asp Val Pro Gly
465                 470                 475                 480

Lys Met Asn Met Ser Cys Ser Gly Thr Ala Val Phe Gly Thr Val Cys
                485                 490                 495

Glu Phe Thr Cys Pro Asp Asp Trp Thr Leu Asn Gly Ser Ala Val Leu
            500                 505                 510

Thr Cys Gly Ala Thr Gly Arg Trp Ser Gly Met Pro Pro Thr Cys Glu
        515                 520                 525

Ala Pro Val Ser Pro Thr Arg Pro
    530                 535

<210> SEQ ID NO 18
<211> LENGTH: 302
<212> TYPE: PRT
<213> ORGANISM: Mus musculus

<400> SEQUENCE: 18

Met Gly Trp Ser Trp Ile Phe Leu Phe Leu Leu Ser Gly Thr Ala Ser
1               5                   10                  15

Val His Ser Trp Tyr Tyr Asn Ala Ser Ser Glu Leu Met Thr Tyr Asp
            20                  25                  30

Glu Ala Ser Ala Tyr Cys Gln Arg Asp Tyr Thr His Leu Val Ala Ile
        35                  40                  45

Gln Asn Lys Glu Glu Ile Asn Tyr Leu Asn Ser Asn Leu Lys His Ser
    50                  55                  60

Pro Ser Tyr Tyr Trp Ile Gly Ile Arg Lys Val Asn Asn Val Trp Ile
65                  70                  75                  80

Trp Val Gly Thr Gly Lys Pro Leu Thr Glu Glu Ala Gln Asn Trp Ala
                85                  90                  95

Pro Gly Glu Pro Asn Asn Lys Gln Arg Asn Glu Asp Cys Val Glu Ile
            100                 105                 110

Tyr Ile Gln Arg Thr Lys Asp Ser Gly Met Trp Asn Asp Glu Arg Cys
        115                 120                 125

Asn Lys Lys Lys Leu Ala Leu Cys Tyr Thr Ala Ser Cys Thr Asn Ala
130                 135                 140

Ser Cys Ser Gly His Gly Glu Cys Ile Glu Thr Ile Asn Ser Tyr Thr
145                 150                 155                 160

Cys Lys Cys His Pro Gly Phe Leu Gly Pro Asn Cys Glu Gln Ala Val
                165                 170                 175

Thr Cys Lys Pro Gln Glu His Pro Asp Tyr Gly Ser Leu Asn Cys Ser
            180                 185                 190

His Pro Phe Gly Pro Phe Ser Tyr Asn Ser Ser Cys Ser Phe Gly Cys
        195                 200                 205

Lys Arg Gly Tyr Leu Pro Ser Ser Met Glu Thr Thr Val Arg Cys Thr
    210                 215                 220

Ser Ser Gly Glu Trp Ser Ala Pro Ala Pro Ala Cys His Val Val Glu
225                 230                 235                 240

Cys Glu Ala Leu Thr His Pro Ala His Gly Ile Arg Lys Cys Ser Ser
```

```
                245                 250                 255
Asn Pro Gly Ser Tyr Pro Trp Asn Thr Thr Cys Thr Phe Asp Cys Val
            260                 265                 270

Glu Gly Tyr Arg Arg Val Gly Ala Gln Asn Leu Gln Cys Thr Ser Ser
            275                 280                 285

Gly Ile Trp Asp Asn Glu Thr Pro Ser Cys Lys Ala Val Thr
            290                 295                 300

<210> SEQ ID NO 19
<211> LENGTH: 283
<212> TYPE: PRT
<213> ORGANISM: Mus musculus

<400> SEQUENCE: 19

Trp Tyr Tyr Asn Ala Ser Ser Glu Leu Met Thr Tyr Asp Glu Ala Ser
  1               5                  10                  15

Ala Tyr Cys Gln Arg Asp Tyr Thr His Leu Val Ala Ile Gln Asn Lys
             20                  25                  30

Glu Glu Ile Asn Tyr Leu Asn Ser Asn Leu Lys His Ser Pro Ser Tyr
         35                  40                  45

Tyr Trp Ile Gly Ile Arg Lys Val Asn Asn Val Trp Ile Trp Val Gly
     50                  55                  60

Thr Gly Lys Pro Leu Thr Glu Glu Ala Gln Asn Trp Ala Pro Gly Glu
 65                  70                  75                  80

Pro Asn Asn Lys Gln Arg Asn Glu Asp Cys Val Glu Ile Tyr Ile Gln
                 85                  90                  95

Arg Thr Lys Asp Ser Gly Met Trp Asn Asp Glu Arg Cys Asn Lys Lys
            100                 105                 110

Lys Leu Ala Leu Cys Tyr Thr Ala Ser Cys Thr Asn Ala Ser Cys Ser
        115                 120                 125

Gly His Gly Glu Cys Ile Glu Thr Ile Asn Ser Tyr Thr Cys Lys Cys
    130                 135                 140

His Pro Gly Phe Leu Gly Pro Asn Cys Glu Gln Ala Val Thr Cys Lys
145                 150                 155                 160

Pro Gln Glu His Pro Asp Tyr Gly Ser Leu Asn Cys Ser His Pro Phe
                165                 170                 175

Gly Pro Phe Ser Tyr Asn Ser Ser Cys Ser Phe Gly Cys Lys Arg Gly
            180                 185                 190

Tyr Leu Pro Ser Ser Met Glu Thr Thr Val Arg Cys Thr Ser Ser Gly
        195                 200                 205

Glu Trp Ser Ala Pro Ala Pro Ala Cys His Val Val Glu Cys Glu Ala
    210                 215                 220

Leu Thr His Pro Ala His Gly Ile Arg Lys Cys Ser Ser Asn Pro Gly
225                 230                 235                 240

Ser Tyr Pro Trp Asn Thr Thr Cys Thr Phe Asp Cys Val Glu Gly Tyr
                245                 250                 255

Arg Arg Val Gly Ala Gln Asn Leu Gln Cys Thr Ser Ser Gly Ile Trp
            260                 265                 270

Asp Asn Glu Thr Pro Ser Cys Lys Ala Val Thr
        275                 280

<210> SEQ ID NO 20
<211> LENGTH: 909
<212> TYPE: DNA
<213> ORGANISM: Artificial Sequence
<220> FEATURE:
<223> OTHER INFORMATION: A synthetic codon-optimized nucleic acid
``` encoding the mouse E-selectin polypeptide with SEQ ID NO:18

<400> SEQUENCE: 20

```
atgggttggt cctggatctt cctgtttctc ttgtctggca ccgctagcgt gcactcatgg      60
tactataacg cctcgagtga gcttatgact tacgacgaag cgtccgcata ctgccagcgt     120
gattatacac atctggtcgc tattcaaaat aaggaggaaa tcaactacct caattctaac     180
ttgaaacaca gcccctcata ctattggatt ggaatccgca aggttaacaa tgtatggatc     240
tgggtgggta cgggcaaacc tcttaccgag gaagcccaga actgggcgcc aggagagccg     300
aacaataagc aaaggaacga agattgtgtc gagatttaca tccagagaac taaggattcg     360
ggtatgtgga cgacgaacg atgcaataaa agaagctgg cactctgtta cacagctagt      420
tgcacgaacg cctcctgttc tggccatgga gagtgcattg agaccatcaa cagctatact     480
tgcaaatgtc accccggttt cttgggccct aattgcgaac aagctgttac atgtaagcca     540
caggagcacc cggattacgg atcactgaac tgctcccatc ccttcggtcc ttttcgtac      600
aatagttctt gcagcttcgg ctgtaaacgt ggatatcttc catcatccat ggaaaccacg     660
gtacgctgca cttcgagtgg tgagtggtct cgccggccc ccgcatgtca cgtggtcgaa      720
tgcgaggctc tcacccatcc tgcccacggc atcaggaagt gcagctccaa cccaggatca     780
taccctgga cacaacttg taccttcgac tgcgttgaag gttacagacg tgtgggcgcg      840
caaaatttgc agtgtacgtc gtctggaatt tgggacaacg agacacctag ttgcaaggct     900
gtcacttaa                                                            909
```

<210> SEQ ID NO 21
<211> LENGTH: 610
<212> TYPE: PRT
<213> ORGANISM: Homo sapiens

<400> SEQUENCE: 21

```
Met Ile Ala Ser Gln Phe Leu Ser Ala Leu Thr Leu Val Leu Leu Ile
 1               5                  10                  15

Lys Glu Ser Gly Ala Trp Ser Tyr Asn Thr Ser Thr Glu Ala Met Thr
            20                  25                  30

Tyr Asp Glu Ala Ser Ala Tyr Cys Gln Gln Arg Tyr Thr His Leu Val
        35                  40                  45

Ala Ile Gln Asn Lys Glu Glu Ile Glu Tyr Leu Asn Ser Ile Leu Ser
    50                  55                  60

Tyr Ser Pro Ser Tyr Tyr Trp Ile Gly Ile Arg Lys Val Asn Asn Val
65                  70                  75                  80

Trp Val Trp Val Gly Thr Gln Lys Pro Leu Thr Glu Glu Ala Lys Asn
                85                  90                  95

Trp Ala Pro Gly Glu Pro Asn Asn Arg Gln Lys Asp Glu Asp Cys Val
            100                 105                 110

Glu Ile Tyr Ile Lys Arg Glu Lys Asp Val Gly Met Trp Asn Asp Glu
        115                 120                 125

Arg Cys Ser Lys Lys Lys Leu Ala Leu Cys Tyr Thr Ala Ala Cys Thr
    130                 135                 140

Asn Thr Ser Cys Ser Gly His Gly Glu Cys Val Glu Thr Ile Asn Asn
145                 150                 155                 160

Tyr Thr Cys Lys Cys Asp Pro Gly Phe Ser Gly Leu Lys Cys Glu Gln
                165                 170                 175

Ile Val Asn Cys Thr Ala Leu Glu Ser Pro Glu His Gly Ser Leu Val
            180                 185                 190
```

-continued

```
Cys Ser His Pro Leu Gly Asn Phe Ser Tyr Asn Ser Ser Cys Ser Ile
        195                 200                 205

Ser Cys Asp Arg Gly Tyr Leu Pro Ser Ser Met Glu Thr Met Gln Cys
        210                 215                 220

Met Ser Ser Gly Glu Trp Ser Ala Pro Ile Pro Ala Cys Asn Val Val
225                 230                 235                 240

Glu Cys Asp Ala Val Thr Asn Pro Ala Asn Gly Phe Val Glu Cys Phe
                245                 250                 255

Gln Asn Pro Gly Ser Phe Pro Trp Asn Thr Thr Cys Thr Phe Asp Cys
            260                 265                 270

Glu Glu Gly Phe Glu Leu Met Gly Ala Gln Ser Leu Gln Cys Thr Ser
        275                 280                 285

Ser Gly Asn Trp Asp Asn Glu Lys Pro Thr Cys Lys Ala Val Thr Cys
        290                 295                 300

Arg Ala Val Arg Gln Pro Gln Asn Gly Ser Val Arg Cys Ser His Ser
305                 310                 315                 320

Pro Ala Gly Glu Phe Thr Phe Lys Ser Ser Cys Asn Phe Thr Cys Glu
                325                 330                 335

Glu Gly Phe Met Leu Gln Gly Pro Ala Gln Val Glu Cys Thr Thr Gln
            340                 345                 350

Gly Gln Trp Thr Gln Gln Ile Pro Val Cys Glu Ala Phe Gln Cys Thr
        355                 360                 365

Ala Leu Ser Asn Pro Glu Arg Gly Tyr Met Asn Cys Leu Pro Ser Ala
        370                 375                 380

Ser Gly Ser Phe Arg Tyr Gly Ser Ser Cys Glu Phe Ser Cys Glu Gln
385                 390                 395                 400

Gly Phe Val Leu Lys Gly Ser Lys Arg Leu Gln Cys Gly Pro Thr Gly
                405                 410                 415

Glu Trp Asp Asn Glu Lys Pro Thr Cys Glu Ala Val Arg Cys Asp Ala
            420                 425                 430

Val His Gln Pro Pro Lys Gly Leu Val Arg Cys Ala His Ser Pro Ile
        435                 440                 445

Gly Glu Phe Thr Tyr Lys Ser Ser Cys Ala Phe Ser Cys Glu Glu Gly
        450                 455                 460

Phe Glu Leu His Gly Ser Thr Gln Leu Glu Cys Thr Ser Gln Gly Gln
465                 470                 475                 480

Trp Thr Glu Glu Val Pro Ser Cys Gln Val Val Lys Cys Ser Ser Leu
                485                 490                 495

Ala Val Pro Gly Lys Ile Asn Met Ser Cys Ser Gly Glu Pro Val Phe
            500                 505                 510

Gly Thr Val Cys Lys Phe Ala Cys Pro Glu Gly Trp Thr Leu Asn Gly
        515                 520                 525

Ser Ala Ala Arg Thr Cys Gly Ala Thr Gly His Trp Ser Gly Leu Leu
        530                 535                 540

Pro Thr Cys Glu Ala Pro Thr Glu Ser Asn Ile Pro Leu Val Ala Gly
545                 550                 555                 560

Leu Ser Ala Ala Gly Leu Ser Leu Leu Thr Leu Ala Pro Phe Leu Leu
                565                 570                 575

Trp Leu Arg Lys Cys Leu Arg Lys Ala Lys Lys Phe Val Pro Ala Ser
            580                 585                 590

Ser Cys Gln Ser Leu Glu Ser Asp Gly Ser Tyr Gln Lys Pro Ser Tyr
        595                 600                 605

Ile Leu
    610
```

<210> SEQ ID NO 22
<211> LENGTH: 610
<212> TYPE: PRT
<213> ORGANISM: Homo sapiens

<400> SEQUENCE: 22

```
Met Ile Ala Ser Gln Phe Leu Ser Ala Leu Thr Leu Val Leu Leu Ile
  1               5                  10                  15

Lys Glu Ser Gly Ala Trp Ser Tyr Asn Thr Ser Thr Glu Ala Met Thr
             20                  25                  30

Tyr Asp Glu Ala Ser Ala Tyr Cys Gln Gln Arg Tyr Thr His Leu Val
         35                  40                  45

Ala Ile Gln Asn Lys Glu Glu Ile Glu Tyr Leu Asn Ser Ile Leu Ser
 50                  55                  60

Tyr Ser Pro Ser Tyr Tyr Trp Ile Gly Ile Arg Lys Val Asn Asn Val
 65                  70                  75                  80

Trp Val Trp Val Gly Thr Gln Lys Pro Leu Thr Glu Glu Ala Lys Asn
                 85                  90                  95

Trp Ala Pro Gly Glu Pro Asn Asn Arg Gln Lys Asp Glu Asp Cys Val
            100                 105                 110

Glu Ile Tyr Ile Lys Arg Glu Lys Asp Val Gly Met Trp Asn Asp Glu
        115                 120                 125

Arg Cys Ser Lys Lys Lys Leu Ala Leu Cys Tyr Thr Ala Ala Cys Thr
130                 135                 140

Asn Thr Ser Cys Ser Gly His Gly Glu Cys Val Glu Thr Ile Asn Asn
145                 150                 155                 160

Tyr Thr Cys Lys Cys Asp Pro Cys Phe Ser Gly Leu Lys Cys Glu Gln
                165                 170                 175

Ile Val Asn Cys Thr Ala Leu Glu Ser Pro Glu His Gly Ser Leu Val
            180                 185                 190

Cys Ser His Pro Leu Gly Asn Phe Ser Tyr Asn Ser Ser Cys Ser Ile
        195                 200                 205

Ser Cys Asp Arg Gly Tyr Leu Pro Ser Ser Met Glu Thr Met Gln Cys
210                 215                 220

Met Ser Ser Gly Glu Trp Ser Ala Pro Ile Pro Ala Cys Asn Val Val
225                 230                 235                 240

Glu Cys Asp Ala Val Thr Asn Pro Ala Asn Gly Phe Val Glu Cys Phe
                245                 250                 255

Gln Asn Pro Gly Ser Phe Pro Trp Asn Thr Thr Cys Thr Phe Asp Cys
            260                 265                 270

Glu Glu Gly Phe Glu Leu Met Gly Ala Gln Ser Leu Gln Cys Thr Ser
        275                 280                 285

Ser Gly Asn Trp Asp Asn Glu Lys Pro Thr Cys Lys Ala Val Thr Cys
290                 295                 300

Arg Ala Val Arg Gln Pro Gln Asn Gly Ser Val Arg Cys Ser His Ser
305                 310                 315                 320

Pro Ala Gly Glu Phe Thr Phe Lys Ser Ser Cys Asn Phe Thr Cys Glu
                325                 330                 335

Glu Gly Phe Met Leu Gln Gly Pro Ala Gln Val Glu Cys Thr Thr Gln
            340                 345                 350

Gly Gln Trp Thr Gln Gln Ile Pro Val Cys Glu Ala Phe Gln Cys Thr
        355                 360                 365

Ala Leu Ser Asn Pro Glu Arg Gly Tyr Met Asn Cys Leu Pro Ser Ala
370                 375                 380
```

```
Ser Gly Ser Phe Arg Tyr Gly Ser Ser Cys Glu Phe Ser Cys Glu Gln
385                 390                 395                 400

Gly Phe Val Leu Lys Gly Ser Lys Arg Leu Gln Cys Gly Pro Thr Gly
            405                 410                 415

Glu Trp Asp Asn Glu Lys Pro Thr Cys Glu Ala Val Arg Cys Asp Ala
            420                 425                 430

Val His Gln Pro Pro Lys Gly Leu Val Arg Cys Ala His Ser Pro Ile
            435                 440                 445

Gly Glu Phe Thr Tyr Lys Ser Ser Cys Ala Phe Ser Cys Glu Glu Gly
        450                 455                 460

Phe Glu Leu Tyr Gly Ser Thr Gln Leu Glu Cys Thr Ser Gln Gly Gln
465                 470                 475                 480

Trp Thr Glu Glu Val Pro Ser Cys Gln Val Val Lys Cys Ser Ser Leu
                485                 490                 495

Ala Val Pro Gly Lys Ile Asn Met Ser Cys Ser Gly Glu Pro Val Phe
            500                 505                 510

Gly Thr Val Cys Lys Phe Ala Cys Pro Glu Gly Trp Thr Leu Asn Gly
            515                 520                 525

Ser Ala Arg Thr Cys Gly Ala Thr Gly His Trp Ser Gly Leu Leu
530                 535                 540

Pro Thr Cys Glu Ala Pro Thr Glu Ser Asn Ile Pro Leu Val Ala Gly
545                 550                 555                 560

Leu Ser Ala Ala Gly Leu Ser Leu Leu Thr Leu Ala Pro Phe Leu Leu
                565                 570                 575

Trp Leu Arg Lys Cys Leu Arg Lys Ala Lys Lys Phe Val Pro Ala Ser
                580                 585                 590

Ser Cys Gln Ser Leu Glu Ser Asp Gly Ser Tyr Gln Lys Pro Ser Tyr
            595                 600                 605

Ile Leu
    610

<210> SEQ ID NO 23
<211> LENGTH: 306
<212> TYPE: PRT
<213> ORGANISM: Artificial Sequence
<220> FEATURE:
<223> OTHER INFORMATION: A synthetic recombinant E-Selectin

<400> SEQUENCE: 23

Met Pro Leu Tyr Lys Leu Leu Asn Val Leu Trp Leu Val Ala Val Ser
1               5                   10                  15

Asn Ala Ile Pro Gly Ser Trp Ser Tyr Asn Thr Ser Thr Glu Ala Met
            20                  25                  30

Thr Tyr Asp Glu Ala Ser Ala Tyr Cys Gln Gln Arg Tyr Thr His Leu
        35                  40                  45

Val Ala Ile Gln Asn Lys Glu Glu Ile Glu Tyr Leu Asn Ser Ile Leu
    50                  55                  60

Ser Tyr Ser Pro Ser Tyr Tyr Trp Ile Gly Ile Arg Lys Val Asn Asn
65                  70                  75                  80

Val Trp Val Trp Val Gly Thr Gln Lys Pro Leu Thr Glu Glu Ala Lys
                85                  90                  95

Asn Trp Ala Pro Gly Glu Pro Asn Asn Arg Gln Lys Asp Glu Asp Cys
            100                 105                 110

Val Glu Ile Tyr Ile Lys Arg Glu Lys Asp Val Gly Met Trp Asn Asp
            115                 120                 125
```

Glu Arg Cys Ser Lys Lys Leu Ala Leu Cys Tyr Thr Ala Ala Cys
        130                 135                 140

Thr Asn Thr Ser Cys Ser Gly His Gly Glu Cys Val Glu Thr Ile Asn
145                 150                 155                 160

Asn Tyr Thr Cys Lys Cys Asp Pro Gly Phe Ser Gly Leu Lys Cys Glu
                165                 170                 175

Gln Ile Val Asn Cys Thr Ala Leu Glu Ser Pro Glu His Gly Ser Leu
            180                 185                 190

Val Cys Ser His Pro Leu Gly Asn Phe Ser Tyr Asn Ser Ser Cys Ser
        195                 200                 205

Ile Ser Cys Asp Arg Gly Tyr Leu Pro Ser Ser Met Glu Thr Met Gln
210                 215                 220

Cys Met Ser Ser Gly Glu Trp Ser Ala Pro Ile Pro Ala Cys Asn Val
225                 230                 235                 240

Val Glu Cys Asp Ala Val Thr Asn Pro Ala Asn Gly Phe Val Glu Cys
                245                 250                 255

Phe Gln Asn Pro Gly Ser Phe Pro Trp Asn Thr Thr Cys Thr Phe Asp
            260                 265                 270

Cys Glu Glu Gly Phe Glu Leu Met Gly Ala Gln Ser Leu Gln Cys Thr
        275                 280                 285

Ser Ser Gly Asn Trp Asp Asn Glu Lys Pro Thr Cys Lys Ala Val Thr
290                 295                 300

Arg Ser
305

<210> SEQ ID NO 24
<211> LENGTH: 331
<212> TYPE: PRT
<213> ORGANISM: Artificial Sequence
<220> FEATURE:
<223> OTHER INFORMATION: A synthetic recombinant E-Selectin protein with
      c-myc

<400> SEQUENCE: 24

Met Gly Trp Ser Trp Ile Phe Leu Phe Leu Leu Ser Gly Thr Ala Ser
1               5                   10                  15

Val His Ser Trp Ser Tyr Asn Thr Ser Thr Glu Ala Met Thr Tyr Asp
            20                  25                  30

Glu Ala Ser Ala Tyr Cys Gln Gln Arg Tyr Thr His Leu Val Ala Ile
        35                  40                  45

Gln Asn Lys Glu Glu Ile Glu Tyr Leu Asn Ser Ile Leu Ser Tyr Ser
    50                  55                  60

Pro Ser Tyr Tyr Trp Ile Gly Ile Arg Lys Val Asn Asn Val Trp Val
65                  70                  75                  80

Trp Val Gly Thr Gln Lys Pro Leu Thr Glu Glu Ala Lys Asn Trp Ala
                85                  90                  95

Pro Gly Glu Pro Asn Asn Arg Gln Lys Asp Glu Asp Cys Val Glu Ile
            100                 105                 110

Tyr Ile Lys Arg Glu Lys Asp Val Gly Met Trp Asn Asp Glu Arg Cys
        115                 120                 125

Ser Lys Lys Lys Leu Ala Leu Cys Tyr Thr Ala Ala Cys Thr Asn Thr
    130                 135                 140

Ser Cys Ser Gly His Gly Glu Cys Val Glu Thr Ile Asn Asn Tyr Thr
145                 150                 155                 160

Cys Lys Cys Asp Pro Gly Phe Ser Gly Leu Lys Cys Glu Gln Ile Val
                165                 170                 175

```
Asn Cys Thr Ala Leu Glu Ser Pro Glu His Gly Ser Leu Val Cys Ser
            180                 185                 190

His Pro Leu Gly Asn Phe Ser Tyr Asn Ser Ser Cys Ile Ser Cys
        195                 200                 205

Asp Arg Gly Tyr Leu Pro Ser Ser Met Glu Thr Met Gln Cys Met Ser
    210                 215                 220

Ser Gly Glu Trp Ser Ala Pro Ile Pro Ala Cys Asn Val Val Glu Cys
225                 230                 235                 240

Asp Ala Val Thr Asn Pro Ala Asn Gly Phe Val Glu Cys Phe Gln Asn
                245                 250                 255

Pro Gly Ser Phe Pro Trp Asn Thr Thr Cys Thr Phe Asp Cys Glu Glu
            260                 265                 270

Gly Phe Glu Leu Met Gly Ala Gln Ser Leu Gln Cys Thr Ser Ser Gly
        275                 280                 285

Asn Trp Asp Asn Glu Lys Pro Thr Cys Lys Ala Val Thr Gly Gly Ala
    290                 295                 300

Ser Thr Arg Ala Ala Glu Gln Lys Leu Ile Ser Glu Glu Asp Leu Asn
305                 310                 315                 320

Gly Thr Arg Ser Gly His His His His His
                325                 330

<210> SEQ ID NO 25
<211> LENGTH: 301
<212> TYPE: PRT
<213> ORGANISM: Homo sapiens

<400> SEQUENCE: 25

Met Gly Trp Ser Trp Ile Phe Leu Phe Leu Leu Ser Gly Thr Ala Ser
1               5                   10                  15

Val His Ser Trp Ser Tyr Asn Thr Ser Thr Glu Ala Met Thr Tyr Asp
            20                  25                  30

Glu Ala Ser Ala Tyr Cys Gln Gln Arg Tyr Thr His Leu Val Ala Ile
        35                  40                  45

Gln Asn Lys Glu Glu Ile Glu Tyr Leu Asn Ser Ile Leu Ser Tyr Ser
    50                  55                  60

Pro Ser Tyr Tyr Trp Ile Gly Ile Arg Lys Val Asn Asn Val Trp Val
65                  70                  75                  80

Trp Val Gly Thr Gln Lys Pro Leu Thr Glu Ala Lys Asn Trp Ala
                85                  90                  95

Pro Gly Glu Pro Asn Asn Arg Gln Lys Asp Glu Asp Cys Val Glu Ile
            100                 105                 110

Tyr Ile Lys Arg Glu Lys Asp Val Gly Met Trp Asn Asp Glu Arg Cys
        115                 120                 125

Ser Lys Lys Lys Leu Ala Leu Cys Tyr Thr Ala Ala Cys Thr Asn Thr
    130                 135                 140

Ser Cys Ser Gly His Gly Glu Cys Val Glu Thr Ile Asn Asn Tyr Thr
145                 150                 155                 160

Cys Lys Cys Asp Pro Gly Phe Ser Gly Leu Lys Cys Glu Gln Ile Val
                165                 170                 175

Asn Cys Thr Ala Leu Glu Ser Pro Glu His Gly Ser Leu Val Cys Ser
            180                 185                 190

His Pro Leu Gly Asn Phe Ser Tyr Asn Ser Ser Cys Ile Ser Cys
        195                 200                 205

Asp Arg Gly Tyr Leu Pro Ser Ser Met Glu Thr Met Gln Cys Met Ser
    210                 215                 220
```

```
Ser Gly Glu Trp Ser Ala Pro Ile Pro Ala Cys Asn Val Val Glu Cys
225                 230                 235                 240

Asp Ala Val Thr Asn Pro Ala Asn Gly Phe Val Glu Cys Phe Gln Asn
                245                 250                 255

Pro Gly Ser Phe Pro Trp Asn Thr Thr Cys Thr Phe Asp Cys Glu Glu
            260                 265                 270

Gly Phe Glu Leu Met Gly Ala Gln Ser Leu Gln Cys Thr Ser Ser Gly
            275                 280                 285

Asn Trp Asp Asn Glu Lys Pro Thr Cys Lys Ala Val Thr
        290                 295                 300

<210> SEQ ID NO 26
<211> LENGTH: 302
<212> TYPE: PRT
<213> ORGANISM: Mus musculus

<400> SEQUENCE: 26

Met Gly Trp Ser Trp Ile Phe Leu Phe Leu Leu Ser Gly Thr Ala Ser
1               5                   10                  15

Val His Ser Trp Tyr Tyr Asn Ala Ser Ser Glu Leu Met Thr Tyr Asp
                20                  25                  30

Glu Ala Ser Ala Tyr Cys Gln Arg Asp Tyr Thr His Leu Val Ala Ile
            35                  40                  45

Gln Asn Lys Glu Glu Ile Asn Tyr Leu Asn Ser Leu Lys His Ser
50                  55                  60

Pro Ser Tyr Tyr Trp Ile Gly Ile Arg Lys Val Asn Asn Val Trp Ile
65                  70                  75                  80

Trp Val Gly Thr Gly Lys Pro Leu Thr Glu Glu Ala Gln Asn Trp Ala
                85                  90                  95

Pro Gly Glu Pro Asn Asn Lys Gln Arg Asn Glu Asp Cys Val Glu Ile
            100                 105                 110

Tyr Ile Gln Arg Thr Lys Asp Ser Gly Met Trp Asn Asp Glu Arg Cys
        115                 120                 125

Asn Lys Lys Lys Leu Ala Leu Cys Tyr Thr Ala Ser Cys Thr Asn Ala
130                 135                 140

Ser Cys Ser Gly His Gly Glu Cys Ile Glu Thr Ile Asn Ser Tyr Thr
145                 150                 155                 160

Cys Lys Cys His Pro Gly Phe Leu Gly Pro Asn Cys Glu Gln Ala Val
                165                 170                 175

Thr Cys Lys Pro Gln Glu His Pro Asp Tyr Gly Ser Leu Asn Cys Ser
            180                 185                 190

His Pro Phe Gly Pro Phe Ser Tyr Asn Ser Ser Cys Ser Phe Gly Cys
        195                 200                 205

Lys Arg Gly Tyr Leu Pro Ser Ser Met Glu Thr Thr Val Arg Cys Thr
210                 215                 220

Ser Ser Gly Glu Trp Ser Ala Pro Ala Pro Ala Cys His Val Val Glu
225                 230                 235                 240

Cys Glu Ala Leu Thr His Pro Ala His Gly Ile Arg Lys Cys Ser Ser
                245                 250                 255

Asn Pro Gly Ser Tyr Pro Trp Asn Thr Thr Cys Thr Phe Asp Cys Val
            260                 265                 270

Glu Gly Tyr Arg Arg Val Gly Ala Gln Asn Leu Gln Cys Thr Ser Ser
        275                 280                 285

Gly Ile Trp Asp Asn Glu Thr Pro Ser Cys Lys Ala Val Thr
290                 295                 300
```

```
<210> SEQ ID NO 27
<211> LENGTH: 19
<212> TYPE: PRT
<213> ORGANISM: Artificial Sequence
<220> FEATURE:
<223> OTHER INFORMATION: A synthetic signal sequence

<400> SEQUENCE: 27

Met Gly Trp Ser Trp Ile Phe Leu Phe Leu Leu Ser Gly Thr Ala Ser
 1               5                  10                  15

Val His Ser

<210> SEQ ID NO 28
<211> LENGTH: 19
<212> TYPE: PRT
<213> ORGANISM: Artificial Sequence
<220> FEATURE:
<223> OTHER INFORMATION: A synthetic signal sequence

<400> SEQUENCE: 28

Met Pro Leu Tyr Lys Leu Leu Asn Val Leu Trp Leu Val Ala Val Ser
 1               5                  10                  15

Asn Ala Ile

<210> SEQ ID NO 29
<211> LENGTH: 30
<212> TYPE: PRT
<213> ORGANISM: Artificial Sequence
<220> FEATURE:
<223> OTHER INFORMATION: A synthetic C-terminal tag sequence

<400> SEQUENCE: 29

Gly Gly Ala Ser Thr Arg Ala Ala Glu Gln Lys Leu Ile Ser Glu Glu
 1               5                  10                  15

Asp Leu Asn Gly Thr Arg Ser Gly His His His His His His
            20                  25                  30

<210> SEQ ID NO 30
<211> LENGTH: 331
<212> TYPE: PRT
<213> ORGANISM: Artificial Sequence
<220> FEATURE:
<223> OTHER INFORMATION: A synthetic human E-selectin polypeptide

<400> SEQUENCE: 30

Met Gly Trp Ser Trp Ile Phe Leu Phe Leu Leu Ser Gly Thr Ala Ser
 1               5                  10                  15

Val His Ser Trp Ser Tyr Asn Thr Ser Thr Glu Ala Met Thr Tyr Asp
            20                  25                  30

Glu Ala Ser Ala Tyr Cys Gln Gln Arg Tyr Thr His Leu Val Ala Ile
        35                  40                  45

Gln Asn Lys Glu Glu Ile Glu Tyr Leu Asn Ser Ile Leu Ser Tyr Ser
    50                  55                  60

Pro Ser Tyr Tyr Trp Ile Gly Ile Arg Lys Val Asn Asn Val Trp Val
65                  70                  75                  80

Trp Val Gly Thr Gln Lys Pro Leu Thr Glu Glu Ala Lys Asn Trp Ala
                85                  90                  95

Pro Gly Glu Pro Asn Asn Arg Gln Lys Asp Glu Asp Cys Val Glu Ile
           100                 105                 110

Tyr Ile Lys Arg Glu Lys Asp Val Gly Met Trp Asn Asp Glu Arg Cys
       115                 120                 125
```

-continued

Ser Lys Lys Lys Leu Ala Leu Cys Tyr Thr Ala Ala Cys Thr Asn Thr
        130                 135                 140

Ser Cys Ser Gly His Gly Glu Cys Val Glu Thr Ile Asn Asn Tyr Thr
145                 150                 155                 160

Cys Lys Cys Asp Pro Gly Phe Ser Gly Leu Lys Cys Glu Gln Ile Val
            165                 170                 175

Asn Cys Thr Ala Leu Glu Ser Pro Glu His Gly Ser Leu Val Cys Ser
        180                 185                 190

His Pro Leu Gly Asn Phe Ser Tyr Asn Ser Ser Cys Ser Ile Ser Cys
            195                 200                 205

Asp Arg Gly Tyr Leu Pro Ser Ser Met Glu Thr Met Gln Cys Met Ser
        210                 215                 220

Ser Gly Glu Trp Ser Ala Pro Ile Pro Ala Cys Asn Val Val Glu Cys
225                 230                 235                 240

Asp Ala Val Thr Asn Pro Ala Asn Gly Phe Val Glu Cys Phe Gln Asn
            245                 250                 255

Pro Gly Ser Phe Pro Trp Asn Thr Thr Cys Thr Phe Asp Cys Glu Glu
            260                 265                 270

Gly Phe Glu Leu Met Gly Ala Gln Ser Leu Gln Cys Thr Ser Ser Gly
        275                 280                 285

Asn Trp Asp Asn Glu Lys Pro Thr Cys Lys Ala Val Thr Gly Gly Ala
290                 295                 300

Ser Thr Arg Ala Ala Glu Gln Lys Leu Ile Ser Glu Glu Asp Leu Asn
305                 310                 315                 320

Gly Thr Arg Ser Gly His His His His His
            325                 330

<210> SEQ ID NO 31
<211> LENGTH: 312
<212> TYPE: PRT
<213> ORGANISM: Artificial Sequence
<220> FEATURE:
<223> OTHER INFORMATION: A synthetic human E-selectin polypeptide

<400> SEQUENCE: 31

Trp Ser Tyr Asn Thr Ser Thr Glu Ala Met Thr Tyr Asp Glu Ala Ser
1               5                   10                  15

Ala Tyr Cys Gln Gln Arg Tyr Thr His Leu Val Ala Ile Gln Asn Lys
            20                  25                  30

Glu Glu Ile Glu Tyr Leu Asn Ser Ile Leu Ser Tyr Ser Pro Ser Tyr
        35                  40                  45

Tyr Trp Ile Gly Ile Arg Lys Val Asn Asn Val Trp Val Trp Val Gly
    50                  55                  60

Thr Gln Lys Pro Leu Thr Glu Glu Ala Lys Asn Trp Ala Pro Gly Glu
65                  70                  75                  80

Pro Asn Asn Arg Gln Lys Asp Glu Asp Cys Val Glu Ile Tyr Ile Lys
            85                  90                  95

Arg Glu Lys Asp Val Gly Met Trp Asn Asp Glu Arg Cys Ser Lys Lys
            100                 105                 110

Lys Leu Ala Leu Cys Tyr Thr Ala Ala Cys Thr Asn Thr Ser Cys Ser
        115                 120                 125

Gly His Gly Glu Cys Val Glu Thr Ile Asn Asn Tyr Thr Cys Lys Cys
    130                 135                 140

Asp Pro Gly Phe Ser Gly Leu Lys Cys Glu Gln Ile Val Asn Cys Thr
145                 150                 155                 160

Ala Leu Glu Ser Pro Glu His Gly Ser Leu Val Cys Ser His Pro Leu

```
                       165                 170                 175
Gly Asn Phe Ser Tyr Asn Ser Ser Cys Ser Ile Ser Cys Asp Arg Gly
                180                 185                 190

Tyr Leu Pro Ser Ser Met Glu Thr Met Gln Cys Met Ser Ser Gly Glu
            195                 200                 205

Trp Ser Ala Pro Ile Pro Ala Cys Asn Val Val Glu Cys Asp Ala Val
        210                 215                 220

Thr Asn Pro Ala Asn Gly Phe Val Glu Cys Phe Gln Asn Pro Gly Ser
225                 230                 235                 240

Phe Pro Trp Asn Thr Thr Cys Thr Phe Asp Cys Glu Glu Gly Phe Glu
                245                 250                 255

Leu Met Gly Ala Gln Ser Leu Gln Cys Thr Ser Ser Gly Asn Trp Asp
            260                 265                 270

Asn Glu Lys Pro Thr Cys Lys Ala Val Thr Gly Gly Ala Ser Thr Arg
        275                 280                 285

Ala Ala Glu Gln Lys Leu Ile Ser Glu Glu Asp Leu Asn Gly Thr Arg
    290                 295                 300

Ser Gly His His His His His His
305                 310

<210> SEQ ID NO 32
<211> LENGTH: 301
<212> TYPE: PRT
<213> ORGANISM: Artificial Sequence
<220> FEATURE:
<223> OTHER INFORMATION: A synthetic human E-selectin polypeptide

<400> SEQUENCE: 32

Met Gly Trp Ser Trp Ile Phe Leu Phe Leu Leu Ser Gly Thr Ala Ser
  1               5                  10                  15

Val His Ser Trp Ser Tyr Asn Thr Ser Thr Glu Ala Met Thr Tyr Asp
                20                  25                  30

Glu Ala Ser Ala Tyr Cys Gln Gln Arg Tyr Thr His Leu Val Ala Ile
            35                  40                  45

Gln Asn Lys Glu Glu Ile Glu Tyr Leu Asn Ser Ile Leu Ser Tyr Ser
        50                  55                  60

Pro Ser Tyr Tyr Trp Ile Gly Ile Arg Lys Val Asn Asn Val Trp Val
65                  70                  75                  80

Trp Val Gly Thr Gln Lys Pro Leu Thr Glu Glu Ala Lys Asn Trp Ala
                85                  90                  95

Pro Gly Glu Pro Asn Asn Arg Gln Lys Asp Glu Asp Cys Val Glu Ile
            100                 105                 110

Tyr Ile Lys Arg Glu Lys Asp Val Gly Met Trp Asn Asp Glu Arg Cys
        115                 120                 125

Ser Lys Lys Lys Leu Ala Leu Cys Tyr Thr Ala Ala Cys Thr Asn Thr
130                 135                 140

Ser Cys Ser Gly His Gly Glu Cys Val Glu Thr Ile Asn Asn Tyr Thr
145                 150                 155                 160

Cys Lys Cys Asp Pro Gly Phe Ser Gly Leu Lys Cys Glu Gln Ile Val
                165                 170                 175

Asn Cys Thr Ala Leu Glu Ser Pro Glu His Gly Ser Leu Val Cys Ser
            180                 185                 190

His Pro Leu Gly Asn Phe Ser Tyr Asn Ser Ser Cys Ser Ile Ser Cys
        195                 200                 205

Asp Arg Gly Tyr Leu Pro Ser Ser Met Glu Thr Met Gln Cys Met Ser
    210                 215                 220
```

Ser Gly Glu Trp Ser Ala Pro Ile Pro Ala Cys Asn Val Val Glu Cys
225                 230                 235                 240

Asp Ala Val Thr Asn Pro Ala Asn Gly Phe Val Glu Cys Phe Gln Asn
            245                 250                 255

Pro Gly Ser Phe Pro Trp Asn Thr Thr Cys Thr Phe Asp Cys Glu Glu
        260                 265                 270

Gly Phe Glu Leu Met Gly Ala Gln Ser Leu Gln Cys Thr Ser Ser Gly
    275                 280                 285

Asn Trp Asp Asn Glu Lys Pro Thr Cys Lys Ala Val Thr
    290                 295                 300

<210> SEQ ID NO 33
<211> LENGTH: 302
<212> TYPE: PRT
<213> ORGANISM: Artificial Sequence
<220> FEATURE:
<223> OTHER INFORMATION: A synthetic mouse E-selectin polypeptide

<400> SEQUENCE: 33

Met Pro Leu Tyr Lys Leu Leu Asn Val Leu Trp Leu Val Ala Val Ser
1               5                   10                  15

Asn Ala Ile Trp Tyr Tyr Asn Ala Ser Ser Glu Leu Met Thr Tyr Asp
            20                  25                  30

Glu Ala Ser Ala Tyr Cys Gln Arg Asp Tyr Thr His Leu Val Ala Ile
        35                  40                  45

Gln Asn Lys Glu Glu Ile Asn Tyr Leu Asn Ser Asn Leu Lys His Ser
    50                  55                  60

Pro Ser Tyr Tyr Trp Ile Gly Ile Arg Lys Val Asn Asn Val Trp Ile
65                  70                  75                  80

Trp Val Gly Thr Gly Lys Pro Leu Thr Glu Glu Ala Gln Asn Trp Ala
            85                  90                  95

Pro Gly Glu Pro Asn Asn Lys Gln Arg Asn Glu Asp Cys Val Glu Ile
        100                 105                 110

Tyr Ile Gln Arg Thr Lys Asp Ser Gly Met Trp Asn Asp Glu Arg Cys
    115                 120                 125

Asn Lys Lys Lys Leu Ala Leu Cys Tyr Thr Ala Ser Cys Thr Asn Ala
130                 135                 140

Ser Cys Ser Gly His Gly Glu Cys Ile Glu Thr Ile Asn Ser Tyr Thr
145                 150                 155                 160

Cys Lys Cys His Pro Gly Phe Leu Gly Pro Asn Cys Glu Gln Ala Val
            165                 170                 175

Thr Cys Lys Pro Gln Glu His Pro Asp Tyr Gly Ser Leu Asn Cys Ser
        180                 185                 190

His Pro Phe Gly Pro Phe Ser Tyr Asn Ser Ser Cys Ser Phe Gly Cys
    195                 200                 205

Lys Arg Gly Tyr Leu Pro Ser Ser Met Glu Thr Thr Val Arg Cys Thr
    210                 215                 220

Ser Ser Gly Glu Trp Ser Ala Pro Ala Pro Ala Cys His Val Val Glu
225                 230                 235                 240

Cys Glu Ala Leu Thr His Pro Ala His Gly Ile Arg Lys Cys Ser Ser
            245                 250                 255

-continued

```
Asn Pro Gly Ser Tyr Pro Trp Asn Thr Thr Cys Thr Phe Asp Cys Val
            260                 265                 270

Glu Gly Tyr Arg Arg Val Gly Ala Gln Asn Leu Gln Cys Thr Ser Ser
        275                 280                 285

Gly Ile Trp Asp Asn Glu Thr Pro Ser Cys Lys Ala Val Thr
    290                 295                 300
```

TREATMENT AND PREVENTION OF VASCULAR DEMENTIA

This application is a continuation-in-part of PCT Application Ser. No. PCT/US2006/034432, filed Aug. 30, 2006, which claims benefit of the filing date of U.S. Provisional Application Ser. No. 60/712,359, filed Aug. 30, 2005, the contents of which applications are specifically incorporated herein in their entireties. This application is also a continuation-in-part of PCT Application Ser. No. PCT/US2007/021682, filed Oct. 9, 2007, which claims benefit of the filing dates of U.S. Provisional Application Ser. Nos. 60/828,732 and 60/905,741, filed Oct. 9, 2006 and Mar. 8, 2007, respectively, the contents of which applications are specifically incorporated herein in their entireties. This application is also a continuation-in-part of U.S. application Ser. No. 11/820,326, filed Jun. 19, 2007, which is a continuation of U.S. application Ser. No. 10/296,423, filed Jun. 11, 2003 now U.S. Pat. No. 7,261 896, which was filed as a national stage application of PCT application PCT/US01/16583, filed May 23, 2001, which claims priority to U.S. Provisional Application Ser. No. 60/206,693, filed May 24, 2000, the contents of which applications are specifically incorporated herein in their entireties.

GOVERNMENT FUNDING

The invention described herein was developed with support from the National Institutes of Health. The U.S. Government has certain rights in the invention.

FIELD OF THE INVENTION

The invention relates to compositions and methods for treatment of vascular dementia in a mammalian subject that involve inducing tolerance to E-selectin in the subject.

BACKGROUND OF THE INVENTION

Vascular dementia can be defined as the loss of cognitive function resulting from ischemic, ischemic-hypoxic, or hemorrhagic brain lesions as a result of cardiovascular diseases and cardiovascular pathologic changes. See, e.g., G. C. Roman, Med. Clin. North. Am., 86, pp. 477-99 (2002). Vascular dementia is a chronic disorder. The symptoms of vascular dementia include cognitive loss, headaches, insomnia and memory loss. Vascular dementia may be caused by multiple strokes (MID or post-stroke dementia) but also by single strategic strokes, multiple lacunes, and hypoperfusion lesions such as border zone infarcts and ischemic periventricular leukoencephalopathy (Binswanger's disease). See, G. C. Roman, supra. In Asian countries such as China, Japan and Korea, vascular dementia is observed in over 60% of patients with dementia. Primary and secondary prevention of stroke and cardiovascular disease decreases the burden of vascular dementia.

Treatment of vascular dementia typically involves control of risk factors (i.e., hypertension, diabetes, smoking, hyperfibrinogenemia, hyperhomocystinemia, orthostatic hypotension, cardiac arrhythmias). See, G. C. Roman, supra. Researchers have also investigated whether hormone replacement therapy and estrogen replacement therapy could delay the onset of dementia in women. See, E. Hogervorst et al., Cochrane Database Syst. Rev., 3, CD003799 (2002). However, such hormone replacement therapy has negative side effects. Moreover, although aspirin is widely prescribed for vascular dementia, there is very limited evidence that aspirin is actually effective in treating vascular dementia patients. See, P. S. Williams et al., Cochrane Database Syst. Rev., 2, CD001296 (2000). Nimodipine has been implicated as a drug demonstrating short-term benefits in vascular dementia patients, but has not been justified as a long-term anti-dementia drug. See, J. M. Lopez-Arrieta and J. Birks, Cochrane Database Syst. Rev., 3, CD000147 (2002). In addition, clinical efficacy data of piracetam does not support the use of this drug in the treatment of dementia or cognitive impairment. L. Flicker and G. Grimley Evans, Cochrane Database Syst. Rev., 2, CD001011 (2001).

Thus, new agents and procedures for treating vascular dementia are needed.

SUMMARY OF THE INVENTION

The invention involves methods and compositions for preventing and treating vascular dementia. Surprisingly, the inventors have discovered that vascular dementia can be treated by inducing immunological tolerance to E-selectin, a cell adhesion molecule that mediates the adhesion of various leukocytes, including neutrophils, monocytes, eosinophils, natural killer (NK) cells, and a subset of T cells, to activated endothelium. Such immunological tolerance leads to the release immune system suppressive cytokines after subsequent stimulation by E-selectin, which is released in response to endothelia activation.

Thus, one aspect of the invention is a pharmaceutical formulation comprising a pharmaceutically acceptable carrier and an effective amount of E-selectin, wherein the formulation is formulated for mucosal administration of E-selectin. For example, the mucosal administration can be intranasal, oral, enteral, vaginal, rectal, or respiratory administration. In some embodiments, the formulation is formulated for intra nasal administration, for example, as an aerosol. The aerosol can be a dry aerosol. Alternatively, the aerosol can be an atomized aqueous solution. The E-selectin is an E-selectin polypeptide. Such an E-selectin polypeptide can be a mammalian E-selectin polypeptide, for example, a human E-selectin, a bovine E-selectin, a murine E-selectin, a rat E-selectin or any other E-selectin polypeptide from a mammalian source.

The pharmaceutical formulation of the invention is typically administered in an effective amount (i.e., a therapeutically effective amount). Such an effective amount of E-selectin is generally sufficient to induce tolerance to E-selectin in a mammal. In some embodiments, an effective amount of E-selectin is sufficient to promote bystander-effect tolerance to E-selectin in a mammal. Examples of effective amounts of E-selectin include ranges of E-selectin of about 0.005 mg to about 500 mg. Another example of an effective amount of E-selectin is a range of E-selectin of about 5 µg to about 50 mg.

Another aspect of the invention is a method for treating or preventing vascular dementia in a mammal comprising mucosal administration of an amount of E-selectin polypeptide sufficient to induce bystander immune tolerance in the mammal. Such vascular dementia can involve reduced blood flow to the brain. In some embodiments, the E-selectin is administered to mucosal surfaces of the mammal. For example, such mucosal administration of E-selectin can include nasal, oral, enteral, vaginal, rectal, or respiratory administration. In some embodiments, the administration is nasal or intranasal. The inventive methods can involve a series of separate E-selectin administrations. In some embodiments, the method involves a first series of administrations of E-selectin over a period of about two weeks. Such a first series of administrations can include about three to about seven administrations of E-selectin over the period of about two weeks. The method can further comprise at least one booster series of administrations of E-selectin after at least two weeks from the first series of administrations. In some embodiments, each booster series of administrations comprise about three to about seven administrations of E-selectin over the period of two weeks.

Another aspect of the invention is a method for treating or preventing vascular dementia in a mammal comprising mucosal administration of an amount of E-selectin polypeptide sufficient to induce bystander immune tolerance in the mammal.

The E-selectin employed in the methods and compositions of the invention can include any of the following sequences: SEQ ID NO:5-8, 18, 19, 30-33, or a combination thereof.

DESCRIPTION OF THE FIGURES

The patent or application file contains at least one drawing executed in color. Copies of this patent or patent application publication with color drawing(s) will be provided by the Office upon request and payment of the necessary fee.

FIG. 1A-B is the mucosal tolerance induction schedules employed for illustrative experiments described herein. For induction of mucosal tolerance, intranasal application of E-selectin was carried out. FIG. 1A shows the schedule for rats that received just a single series of E-selectin or PBS (control) administrations; rats receiving the single series of administrations are sometimes referred to herein as the "non-booster group." FIG. 1B shows the schedule for rats that received a series of booster administrations of E-selectin or PBS (control) every three weeks; animals receiving such a series of administrations are sometimes referred to herein as the "booster group."

FIG. 5A shows the percentage of correct choices made by E-selectin tolerized, PBS control and sham operated animals two weeks after carotid artery ligation. FIG. 5B shows the percentage of correct choices made by E-selectin tolerized, PBS control and sham operated animals six weeks after carotid artery ligation. FIG. 5C shows the percentage of correct choices made by E-selectin tolerized, PBS control and sham operated animals ten weeks after carotid artery ligation. Some variability in the E-selectin group responses was observed at six weeks after ligation (FIG. 5B), but in general, by the third day after acquisition, the percentages of correct T-arm entries of the E-selectin and sham-operated animals were significantly increased as compared with the PBS group.

FIG. 11A-B show rat corpus callosum sections immunohistochemically stained for CD4 (a marker for T cells). Sham-treated rats exhibited little or no CD4 positive T cell infiltration (FIG. 11A). In contrast, after carotid artery occlusion, increased numbers of CD4 positive T cells were observed in the corpus callosum of rats (FIG. 11B).

FIG. 17A-C provides a comparison of E-selectin sequences where Line 1 is wild type E-Selectin (human), GenBank Acc. No. M30640 (SEQ ID NO:21); Line 2: wild type E-Selectin (human), GenBank Acc. No. NM_000450 (SEQ ID NO:22); Line 3: "new" recombinant E-Selectin, no tags (SEQ ID NO:23). Line 4: "old" recombinant E-Selectin protein with c-myc, Histidine tags (SEQ ID NO:24). The Underlined sequences are signal peptide sequences; the symbol ****** indicates that the sequences are part of the transmembrane domain; the symbol ###### indicates that the sequences are c-myc and/or Histidine tags; the symbol ////// indicates that the sequences Lectin C-type domain sequences; the symbol @@@@@@ indicates that the sequences are Calcium binding EGF-like domain sequences. See, Nession et al., PNAS 87, 1673-1677 (1990); Zhang et al., FEMS Microbiol Lett 227, 303-309 (2003); Kiely et al., J Immunol 171, 3216-3224 (2003).

FIG. 18 is a comparison of human (SEQ ID NO:25, top sequence) and mouse (SEQ ID NO:26, bottom sequence) E-selectin sequences.

DETAILED DESCRIPTION OF THE INVENTION

Figure 2:
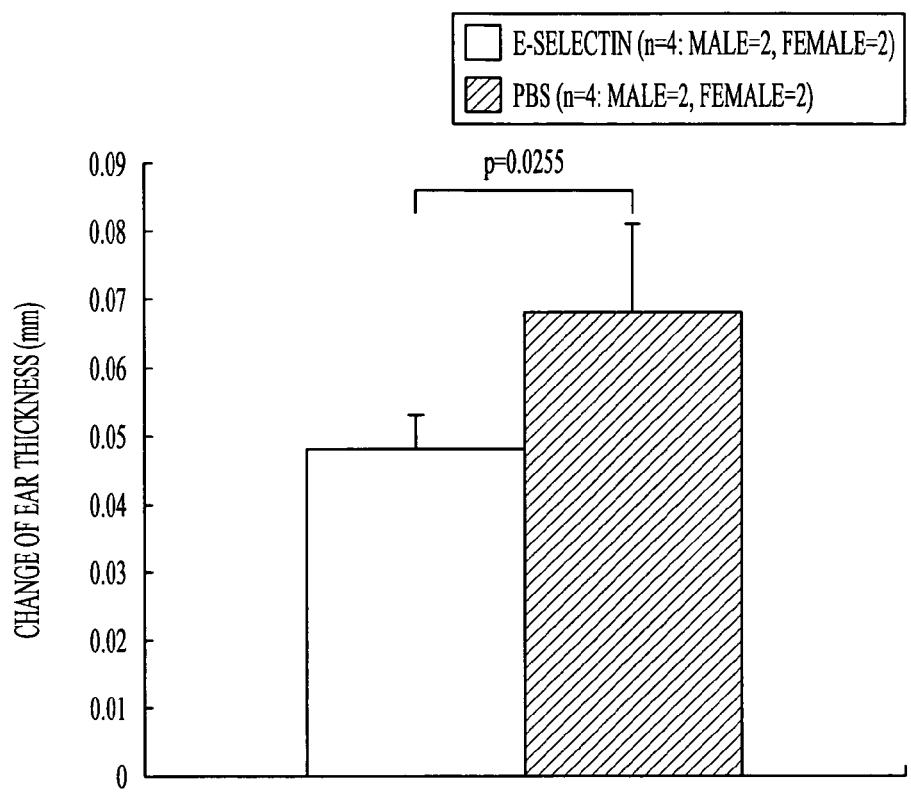
FIG. 2 graphically illustrates the delayed type hypersensitivity (DTH) reaction in E-selectin-tolerized rats compared with PBS-tolerized rats. For this experiment, rats received an intranasal administration of E-selectin or phosphate buffered saline (PBS, control), and then were immunized with E-selectin in the footpad prior to challenge by an injection of E-selectin in the ear. This bar graph illustrates the change in thickness of the ear in animals that received intranasal instillation of E-selectin compared to the ear swelling in animals that received intranasal PBS. E-selectin administration on a single tolerization schedule significantly suppressed the delayed type hypersensitivity (DTH) induction of ear swelling in these animals. Therefore, intranasal instillation of E-selectin in the doses used in these animals does produce a state of immunological tolerization.

The invention provides compositions and methods for treating, inhibiting and/or preventing negative consequences of vascular dementia.
Definitions
As used herein, "tolerance" refers to an antigen-induced immune unresponsiveness upon re-exposure to the antigen. The antigen has previously been administered to induce such immune unresponsiveness. The induced immune unresponsiveness may be specific for the administered antigen or may be antigen-non-specific as a result of production of an antigen-non-specific suppressor substance such as transforming growth factor beta (TGFβ), interleukin-4 (IL-4) or interleukin-10 (IL-10).

As used herein "bystander tolerance" means that T-cells, which are primed to recognize a specific antigen (E-selectin), release immune system suppressive cytokines after subsequent stimulation by that antigen (E-selectin). Such suppressor T cells arise in the mucosal immune system and migrate to systemic sites where, upon antigen-specific reactivation, the suppressor T cells release TGFβ, IL-4, IL-10 and other suppressive cytokines A delayed type hypersensitivity reaction as used herein is a measure of whether the immune system actively reacts to an antigen or whether the immune system exhibits tolerance towards the antigen. An antigen is introduced intradermally, and after about 48-72 hours post-injection the site of intradermal administration is observed. If the immune system does not exhibit tolerance, the injection site will appear red, inflamed, thickened, and tender. The swelling and thickening of the skin are a result of an immune response. The lack of a delayed type hypersensitivity response to the antigen indicates that the immune system is tolerant of the antigen.

As used herein, a "subject" is a mammal or bird to which the E-selectin compositions of the invention are administered. Thus, the subject can be bovine, rat, mouse, dog, pig, horse, goat, monkey, ape, human or other domestic or zoo mammal. In addition, the subject can be chicken, turkey, parrot or other domestic or zoo bird.

As used herein, vascular dementia is a loss of cognitive function as a result of diminished blood flow to the brain. Vascular dementia can arise from diminished blood flow in arteries within the heart and/or in blood vessels leading to the brain. While vascular dementia need not be a result of blockage in blood vessels within the brain, in some instances, vascular dementia can occur as a result of such diminished blood flow in blood vessels within the brain. Vascular dementia can occur as a result of single event that reduces blood flow from the heart and/or with blood vessels leading to the brain. However, vascular dementia can also have a slow onset, for example, as a result of progressive decrease in blood flow from the heart to the brain over time.
E-Selectin E-selectin (also known as ELAM-1, CD62, and CD62E) is a cytokine-inducible cell surface glycoprotein that is found on endothelial cells. E-selectin is a cell adhesion molecule that mediates the adhesion of various leukocytes, including neutrophils, monocytes, eosinophils, natural killer (NK) cells, and a subset of T cells, to activated endothelium. See, e.g., Bevilacqua, et al., "Endothelial leukocyte adhesion molecule 1: an inducible receptor for neutrophils related to complement regulatory proteins and lectins," Science 243; 1160 (1989); Graber, et al., "T cells bind to cytokine-activated endothelial cells via a novel, inducible sialoglycoprotein and endothelial leukocyte adhesion molecule-1" J. Immunol. 145: 819 (1990); Carlos, et al., "Human monocytes bind to two cytokine-induced adhesive ligands on cultured human endothelial cells: endothelial-leukocyte adhesion molecule-1 and vascular cell adhesion molecule-1" Blood 77: 2266 (1991); Hakkert, et al., "Neutrophil and monocyte adherence to and migration across monolayers of cytokine-activated endothelial cells: the contribution of CD18, ELAM-1, and VLA-4" Blood 78: 2721 (1991); and Picker, et al., "ELAM-1 is an adhesion molecule for skin-homing T cells" Nature 349: 796 (1991).

E-selectin is expressed in vascular endothelial tissue. Pober, J. S., et al., J. Immunol. 136: 1680 (1986); Bevilacqua M. P., et al., Proc. Natl. Acad. Sci. 84: 9238 (1987). Expression of E-selectin is induced in response to the cytokines IL-1 and TNF, as well as bacterial lipopolysaccharide (LPS), through transcriptional up-regulation. Pobor et al., supra; see also, Montgomery, et al., "Activation of endothelial-leukocyte adhesion molecule 1 (ELAM-1) gene transcription" Proc. Natl. Acad. Sci. 88: 6523 (1991)). Some workers hypothesize that activation of vascular endothelial cells is involved in inflammatory vascular tissue damage leading to thrombosis. Fareed, J. et al., "Molecular markers of hemostatic activation. Implications in the diagnosis of thrombosis, vascular, and cardiovascular disorders," Clin. Lab. Med. 15: 39 (1995).

Structurally, E-selectin belongs to a family of adhesion molecules termed "selectins." This family also includes P-selectin and L-selectin. Review articles relating to these selectins are provide in Lasky, "Selectins: interpreters of cell-specific carbohydrate information during inflammation" Science 258: 964 (1992) and Bevilacqua and Nelson, "Selectins" J. Clin. Invest. 91: 379 (1993). These molecules are characterized by common structural features such as an amino-terminal lectin-like domain, an epidermal growth factor (EGF) domain, and a discrete number of complement repeat modules (approximately 60 amino acids each) similar to those found in certain complement binding proteins.

Examples of nucleic acid and amino acid sequences for different types and species of E-selectin can be found in the art, for example, in the NCBI database. See website at ncbi.nlm.nih.gov. Thus, for example, the NCBI database provides a human E-selectin precursor amino acid sequence as accession number P16581 (gi: 126180). This sequence is provided below for easy reference as SEQ ID NO1.

```
  1 MIASQFLSAL TLVLLIKESG AWSYNTSTEA MTYDEASAYC
 41 QQRYTHLVAI QNKEEIEYLN SILSYSPSYY WIGIRKVNNV
 81 WVWVGTQKPL TEEAKNWAPG EPNNRQKDED CVEIYIKREK
121 DVGMWNDERC SKKKLALCYT AACTNTSCSG HGECVETINN
161 YTCKCDPGFS GLKCEQIVNC TALESPEHGS LVCSHPLGNF
201 SYNSSCSISC DRGYLPSSME TMQCMSSGEW SAPIPACNVV
241 ECDAVTNPAN GFVECFQNPG SFPWNTTCTF DCEEGFELMG
281 AQSLQCTSSG NWDNEKPTCK AVTCRAVRQP QNGSVRCSHS
321 PAGEFTFKSS CNFTCEEGFM LQGPAQVECT TQGQWTQQIP
361 VCEAFQCTAL SNPERGYMNC LPSASGSFRY GSSCEFSCEQ
401 GFVLKGSKRL QCGPTGEWDN EKPTCEAVRC DAVHQPPKGL
441 VRCAHSPIGE FTYKSSCAFS CEEGFELHGS TQLECTSQGQ
481 WTEEVPSCQV VKCSSLAVPG KINMSCSGEP VFGTVCKFAC
521 PEGWTLNGSA ARTCGATGHW SGLLPTCEAP TESNIPLVAG
561 LSAAGLSLLT LAPFLLWLRK CLRKAKKFVP ASSCQSLESD
601 GSYQKPSYIL
```

The mature sequence for this human E-selectin extends from about amino acid 22 to amino acid 610. The sequence for this mature E-selectin polypeptide is therefore as follows (SEQ ID NO:2).

```
 22                    WSYNTSTEA MTYDEASAYC
 41 QQRYTHLVAI QNKEEIEYLN SILSYSPSYY WIGIRKVNNV
 81 WVWVGTQKPL TEEAKNWAPG EPNNRQKDED CVEIYIKREK
121 DVGMWNDERC SKKKLALCYT AACTNTSCSG HGECVETINN
161 YTCKCDPGFS GLKCEQIVNC TALESPEHGS LVCSHPLGNF
201 SYNSSCSISC DRGYLPSSME TMQCMSSGEW SAPIPACNVV
241 ECDAVTNPAN GFVECFQNPG SFPWNTTCTF DCEEGFELMG
281 AQSLQCTSSG NWDNEKPTCK AVTCRAVRQP QNGSVRCSHS
321 PAGEFTFKSS CNFTCEEGFM LQGPAQVECT TQGQWTQQIP
361 VCEAFQCTAL SNPERGYMNC LPSASGSFRY GSSCEFSCEQ
401 GFVLKGSKRL QCGPTGEWDN EKPTCEAVRC DAVHQPPKGL
441 VRCAHSPIGE FTYKSSCAFS CEEGFELHGS TQLECTSQGQ
481 WTEEVPSCQV VKCSSLAVPG KINMSCSGEP VFGTVCKFAC
521 PEGWTLNGSA ARTCGATGHW SGLLPTCEAP TESNIPLVAG
561 LSAAGLSLLT LAPFLLWLRK CLRKAKKFVP ASSCQSLESD
601 GSYQKPSYIL
```

An extracellular E-selectin domain may be used for tolerization of a subject. The extracellular domain of the human E-selectin provided above includes a sequence of about amino acid 22 to about amino acid 556 and therefore has the following sequence (SEQ ID NO:3).

```
 22                    WSYNTSTEA MTYDEASAYC
 41 QQRYTHLVAI QNKEEIEYLN SILSYSPSYY WIGIRKVNNV
 81 WVWVGTQKPL TEEAKNWAPG EPNNRQKDED CVEIYIKREK
121 DVGMWNDERC SKKKLALCYT AACTNTSCSG HGECVETINN
161 YTCKCDPGFS GLKCEQIVNC TALESPEHGS LVCSHPLGNF
201 SYNSSCSISC DRGYLPSSME TMQCMSSGEW SAPIPACNVV
241 ECDAVTNPAN GFVECFQNPG SFPWNTTCTF DCEEGFELMG
281 AQSLQCTSSG NWDNEKPTCK AVTCRAVRQP QNGSVRCSHS
321 PAGEFTFKSS CNFTCEEGFM LQGPAQVECT TQGQWTQQIP
361 VCEAFQCTAL SNPERGYMNC LPSASGSFRY GSSCEFSCEQ
401 GFVLKGSKRL QCGPTGEWDN EKPTCEAVRC DAVHQPPKGL
441 VRCAHSPIGE FTYKSSCAFS CEEGFELHGS TQLECTSQGQ
481 WTEEVPSCQV VKCSSLAVPG KINMSCSGEP VFGTVCKFAC
521 PEGWTLNGSA ARTCGATGHW SGLLPTCEAP TESNIP
```

In some embodiments human E-selectin may be administered to a subject. As is known to the skilled artisan, some sequence variation exists in human E-selectins. Thus, other human E-selectin amino acid sequences can be found in the NCBI database, for example, as accession numbers AANO1237 (gi: 22536178), CAA17434 (gi: 3115964), AAA52376 (gi: 537524), CAI119357 (gi: 56417699), among others. According to the invention, any such human E-selectin polypeptides can be used for administration to a subject.

As indicated above, wild type E-selectins have a total about of 589 amino acids. Such wild type E-selectins include a lectin domain, an epidermal growth factor-like (EGF) domain, and a series of between 2 and 9 consensus repeat domains similar to those of complement proteins. Thus, wild type E-selectin, for example, the E-selectin sequences provided in FIG. 17, can generally include the structural elements shown below.

Amino acids 1-21: signal sequence
Amino acids 22-140: lectin like domain
Amino acid 144-175: EGF like domain
Amino acid 180-237: first consensus repeat domain
Amino acid 242-300: second consensus repeat domain
Amino acid 300-363: third consensus repeat domain
Amino acid 367-426: fourth consensus repeat domain
Amino acid 430-489: fifth consensus repeat domain
Amino acid 493-548: sixth consensus repeat domain A membrane spanning domain of about 22 amino acids and an intracellular domain of about 32 amino acids are also present at the carboxyl terminus of wild type E-selectin (see FIG. 17). However, neither the membrane-spanning domain nor the intracellular domain need be present in the E-selectins used in the compositions and methods of the invention. Moreover, several of the consensus repeat domains can be eliminated from the E-selectin used in the compositions and methods of the invention.

Thus, in some embodiments, the E-selectin is a soluble E-selectin that does not contain the membrane spanning domain or the intracellular domain. Soluble E-selectin can be generated by enzymatic cleavage (to eliminate the membrane spanning domain and/or the intracellular domain) or by recombinant expression of the soluble E-selectin portion of the molecule. The exact amino acid sequence of E-selectin can therefore vary depending on the cleavage site chosen for deleting the membrane spanning and/or the intracellular domains, or the C-terminus selected for making a recombinant soluble E-selectin. In addition, the number of complement-like consensus repeats can vary.

Thus, in some embodiments, the extracellular portion of the E-selectin molecule is used. Such an extracellular region of E-selectin can have up to about 550 amino acids or more desirably up to about 535 amino acids. However, in many embodiments the extracellular domain of E-selectin has less than about 550 to 535 amino acids. For example, the extracellular domain used in the compositions and methods of the invention can have about 1 to about 260 amino acids, or any integer in between, fewer amino acids than the 535-550 amino acids that generally comprises the E-selectin extracellular domain. Thus, the extracellular domain of E-selectin that is used in the compositions and methods of the invention can have at least about 275, about 280, about 285, about 290, about 295, about 300, about 310, about 315, about 320, about 325 amino acids or any integer from at least about 275 to at least about 325 amino acids.

In general, the extracellular domain of E-selectin includes, from the amino terminus of the E-selectin protein: the lectin domain, the epidermal growth factor-like (EGF) domain, and a series of between 2 and 9 consensus repeat domains similar to those of complement proteins. Thus, the E-selectin can have about 2, about 3, about 4, about 5, about 6, about 7, about 8 or about 9 consensus repeat domains. Depending on the number of consensus repeat domains, the total number of amino acids and the molecular weight of E-selectin will therefore change.

The consensus repeat domains of E-selectin are also called complement control protein (CCP) modules, short consensus repeats (SCRs) or SUSHI repeats. These consensus repeat domains contain approximately 60 amino acid residues and have been identified in several proteins of the complement system. For example, there are two consensus repeat domains at positions 13-53 and 57-112 in the following sequence (NCBI accession number AAQ67702; gi: 34420911; SEQ ID NO:4).

```
  1 PKGLVRCAHS PIGEFTYKSS CAFSCEEGFE LYGSTQLECT

41 SQGQWTEEVP SCQVVKCSSL AVPGKINMSC SGEPVFGTVC

81 KFACPEGWTL NGSAARTCGA TGHWSGLLPT CEAPTESNIP

121 LVAGLSAAGL SLLTLAPF
```

In one embodiment, a human E-selectin protein is used in the compositions and methods of the invention that has about 306 amino acids (e.g. SEQ ID NO:5).

```
  1 MPLYKLLNVL WLVAVSNAIP GSWSYNTSTE AMTYDEASAY

41 CQQRYTHLVA TQNKEEIEYL NSILSYSPSY YWIGIRKVNN

81 VWVWVGTQKP LTEEAKNWAP GEPNNRQKDE DCVEIYIKRE

121 KDVGMWNDER CSKKKLALCY TAACTNTSCS GHGECVETIN

161 NYTCKCDPGE SGLKCEQIVN CTALESPEHG SLVCSHPLGN

201 FSYNSSCSIS CDRGYLPSSM ETMQCMSSGE WSAPIPACNV

241 VECDAVTNPA NGFVECFQNP GSFPWNTTCT FDCEEGFELM

281 GAQSLQCTSS GNWDNEKPTC KAVTRS
```

The SEQ ID NO:5 E-selectin sequence is part of the third sequence identified as the "new" recombinant E-Selectin with no tags shown in FIG. 18. In another embodiment, the human E-selectin protein used in the compositions and methods of the invention that has about 304 amino acids (e.g. SEQ ID NO:6), because the C-terminal arginine and serine residues are not present.

```
  1 MPLYKLLNVL WLVAVSNAIP GSWSYNTSTE AMTYDEASAY

41 CQQRYTHLVA IQNKEEIEYL NSILSYSPSY YWIGIRKVNN

81 VWVWVGTQKP LTEEAKNWAP GEPNNRQKDE DCVEIYIKRE

121 KDVGMWNDER CSKKKLALCY TAACTNTSCS GHGECVETIN

161 NYTCKCDPGF SGLKCEQIVN CTALESPEHG SLVCSHPLGN

201 FSYNSSCSIS CDRGYLPSSM ETMQCMSSGE WSAPIPACNV

241 VECDAVTNPA NGFVECFQNP GSFPWNTTCT FDCEEGFELM

281 GAQSLQCTSS GNWDNEKPTC KAVT
```

In another embodiment, a human E-selectin protein without a signal sequence is used in the compositions and methods of the invention that has about 284 amino acids (e.g. SEQ ID NO: 7).

```
  1 WSYNTSTEAM TYDEASAYCQ QRYTHLVAIQ NKEEIEYLNS

41 ILSYSPSYYW IGIRKVNNVW VWVGTQKPLT EEAKNWAPGE

81 PNNRQKDEDC VEIYIKREKD VGMWNDERCS KKKLALCYTA

121 ACTNTSCSGH GECVETINNY TCKCDPGFSG LKCEQIVNCT

161 ALESPEHGSL VCSHPLGNFS YNSSCSISCD RGYLPSSMET
```

```
201 MQCMSSGEWS APIPACNVVE CDAVTNPANG FVECFQNPGS

241 FPWNTTCTFD CEEGFELMGA QSLQCTSSGN WDNEKPTCKA

281 VTRS
```

In a further embodiment, the human E-selectin protein used in the compositions and methods of the invention that has about 282 amino acids (e.g. SEQ ID NO:8), because the signal sequence and the C-terminal arginine and serine residues are not present.

```
  1 WSYNTSTEAM TYDEASAYCQ QRYTHLVAIQ NKEEIEYLNS

41 ILSYSPSYYW IGIRKVNNVW VWVGTQKPLT EEAKNWAPGE

81 PNNRQKDEDC VEIYIKREKD VGMWNDERCS KKKLALCYTA

121 ACTNTSCSGH GECVETINNY TCKCDPGFSG LKCEQIVNCT

161 ALESPEHGSL VCSHPLGNFS YNSSCSISCD RGYLPSSMET

201 MQCMSSGEWS APIPACNVVE CDAVTNPANG FVECFQNPGS

241 FPWNTTCTFD CEEGFELMGA QSLQCTSSGN WDNEKPTCKA

281 VT
```

These approximate 282-284 amino acid sequences for E-selectin has the lectin domain, the EGF domain, and two complement-like consensus repeats.

In some embodiments, a signal sequence may be present on the N-terminus of the E-selectin. One example of a signal sequence that can be used is the MGWSWIFLFLLSGTASVHS (SEQ ID NO:27) signal sequence. Another example of a signal sequence that can be used is the MPLYKLLNVLWLVAVSNAI (SEQ ID NO:28) signal sequence. Also in some embodiments, a C-terminal tag sequence may be used with the E-selectin. One example of a C-terminal tag sequence that can be used is a histidine tag sequence, for example, the GGASTRAAEQKLI SEEDLNGTRSGHHHHHH (SEQ ID NO:29) tag sequence.

In addition, in some embodiments it may be useful to administer E-selectin from non-human species to the subject. Thus, for example, non-human E-selectin may optimally inhibit inflammation and/or induce tolerization to E-selectin in some human subjects. Therefore, the invention is directed to administering non-human E-selectin to subjects, and such non-human E-selectin can include just the extracellular portion of the E-selectin and/or the extracellular portion of E-selectin with just 2 to about 9 consensus repeat domains. Many sources and examples of non-human E-selectin are available. For example, nucleic acid and amino acid sequences for different types of non-human E-selectin can be found in the art, for example, in the NCBI database. See website at ncbi.nlm.nih.gov. Thus, for example, bovine, rat, mouse, dog, pig, horse, goat, monkey, ape or other mammalian E-selectin polypeptides can be administered to a subject. Sequences for such mammalian E-selectins are available, for example, in the NCBI database.

One example of a bovine E-selectin polypeptide sequence that can be found in the NCBI database is the bovine E-selectin sequence with accession number P98107 (gi: 1346435). This bovine E-selectin sequence is the precursor sequence and is provided below for easy reference (SEQ ID NO:9).

```
  1 MIVSQYLSAL TFVLLLFKES RTWSYHASTE MMTFEEARDY

41 CQKTYTALVA IQNQEEIEYL NSTFSYSPSY YWIGIRKING

81 TWTWIGTNKS LTKEATNWAP GEPNNKQSDE DCVEIYIKRE

121 KDSGKWNDEK CTKQKLALCY KAACNPTPCG SHGECVETIN

161 NYTCQCHPGF KGLKCEQVVT CPAQKHPEHG HLVCNPLGKF

201 TYNSSCSISC AEGYLPSSTE ATRCMSSGEW STPLPKCNVV

241 KCDALSNLDN GVVNCSPNHG SLPWNTTCTF ECQEGYKLTG

281 PQHLQCTSSG IWDNKQPTCK AVSCAAISHP QNGTVNCSHS

321 VVGDFAEKSS CHFTCAEGFT LQGPTQVECT AQGQWTQRVP

361 VCEVVRCSRL DVSGKLNMNC SGEPVLGTEC TFACPERWTL

401 NGSVVLTCGA TGHWSGMLPT CEAPTVSQTP LAVGLSTAGV

441 SLVTIPSFLF WLLKRLQKKA KKFSPASSCS SLKSNGCYST

481 PSKLI
```

The mature sequence for this bovine E-selectin extends from about amino acid 23 to amino acid 485. The sequence for this mature bovine E-selectin polypeptide is therefore as follows (SEQ ID NO:10).

```
 23                              WSYHASTE MMTFEEARDY

41 CQKTYTALVA IQNQEEIEYL NSTFSYSPSY YWIGIRKING

81 TWTWIGTNKS LTKEATNWAP GEPNNKQSDE DCVEIYIKRE

121 KDSGKWNDEK CTKQKLALCY KAACNPTPCG SHGECVETIN

161 NYTCQCHPGF KGLKCEQVVT CPAQKHPEHG HLVCNPLGKF

201 TYNSSCSISC AEGYLPSSTE ATRCMSSGEW STPLPKCNVV

241 KCDALSNLDN GVVNCSPNHG SLPWNTTCTF ECQEGYKLTG

281 PQHLQCTSSG IWDNKQPTCK AVSCAAISHP QNGTVNCSHS

321 VVGDFAFKSS CHFTCAEGFT LQGPTQVECT AQGQWTQRVP

361 VCEVVRCSRL DVSGKLNMNC SGEPVLGTEC TFACPERWTL

401 NGSVVLTCGA TGHWSGMLPT CEAPTVSQTP LAVGLSTAGV

441 SLVTIPSFLF WLLKRLQKKA KKFSPASSCS SLKSNGCYST

481 PSKLI
```

An extracellular E-selectin domain may be used for tolerization of a subject. The extracellular domain of the bovine E-selectin provided above includes a sequence of about amino acid 23 to about amino acid 430 and therefore has the following sequence (SEQ ID NO:11).

```
 23                              WSYHASTE MMTFEEARDY

41 CQKTYTALVA IQNQEEIEYL NSTFSYSPSY YWIGIRKING

81 TWTWIGTNKS LTKEATNWAP GEPNNKQSDE DCVEIYIKRE

121 KDSGKWNDEK CTKQKLALCY KAACNPTPCG SHGECVETIN

161 NYTCQCHPGF KGLKCEQVVT CPAQKHPEHG HLVCNPLGKF

201 TYNSSCSISC AEGYLPSSTE ATRCMSSGEW STPLPKCNVV

241 KCDALSNLDN GVVNCSPNHG SLPWNTTCTF ECQEGYKLTG
```

```
281 PQHLQCTSSG IWDNKQPTCK AVSCAAISHP QNGTVNCSHS

321 VVGDFAFKSS CHFTCAEGFT LQGPTQVECT AQGQWTQRVP

361 VCEVVRCSRL DVSGKLNMNC SGEPVLGTEC TFACPERWTL

401 NGSVVLTCCA TGHWSGMLPT CEAPTVSQTP
```

As is known to the skilled artisan, some sequence variation exists among bovine E-selectins. Thus, other bovine E-selectin amino acid sequences can be found in the NCBI database, for example, as accession numbers S36772 (gi: 480377) and NP 776606 (gi: 27806407), among others. According to the invention, any such bovine E-selectin polypeptides can be used for tolerization of a subject to E-selectin.

One example of a rat E-selectin polypeptide sequence that can be found in the NCBI database is the rat E-selectin sequence with accession number P98105 (gi: 1346437). This rat E-selectin sequence is the precursor sequence and is provided below for easy reference (SEQ ID NO:12).

```
  1 MNASCFLSAL TFVLLIGKSI AWYYNASSEL MTYDEASAYC

41 QRDYTHLVAI QNKEEINYLN STLRYSPSYY WIGIRKVNNV

81 WIWVGTQKPL TEEAKNWAPG EPNNKQRNED CVEIYTQRPK

121 DSGMWNDERC DKKKLALCYT ASCTNTSCSG HGECVETINS

161 YTCKCHPGFL GPKCDQVVTC QEQEYPDHGS LNCTHPFGLF

201 SYNSSCSFSC ERGYVPSSME TTVRCTSSGE WSAPAPACHV

241 VECKALTQPA HGVRKCSSNP GSYPWNTTCT FDCEEGYRRV

281 GAQNLQCTSS GVWDNEKPSC KAVTCDAIPR PQNGSVSCSN

321 STAGALAFKS SCNFTCEHSF TLQGPAQVEC SAQGQWTPQI

361 PVCKASQCEA LSAPQRGHMK CLPSASAPFQ SGSSCKFSCD

401 EGFELKGSRR LQCGPRGEWD SEKPTCAGVQ CSSLDLPGKM

441 NMSCSCPAVF GTVCEFTCPE GWTLNGSSIL TCGATGRWSA

481 MLPTCEAPAN PPRPLVVALS VAATSLLTLS SLIYVLKRFF

521 WKKAKKFVPA SSCQSLQSFE NYQGPSYII
```

The mature sequence for this rat E-selectin extends from about amino acid 22 to amino acid 549. The sequence for this mature rat E-selectin polypeptide is therefore as follows (SEQ ID NO:13).

```
 22                    WYYNASSEL MTYDEASAYC

41 QRDYTHLVAI QNKEEINYLN STLRYSPSYY WIGIRKVNNV

81 WIWVGTQKPL TEEAKNWAPG EPNNKQRNED CVEIYIQRPK

121 DSGMWNDERC DKKKLALCYT ASCTNTSCSG HGECVETINS

161 YTCKCHPGFL GPKCDQVVTC QEQEYPDHGS LNCTHPFGLF

201 SYNSSCSFSC ERGYVPSSME TTVRCTSSGE WSAPAPACHV

241 VECKALTQPA HGVRKCSSNP GSYPWNTTCT FDCEEGYRRV

281 GAQNLQCTSS GVWDNEKPSC KAVTCDAIPR PQNGSVSGSN

321 STAGALAFKS SCNFTCEHSF TLQGPAQVEC SAQGQWTPQI

361 PVCKASQCEA LSAPQRGHMK CLPSASAPFQ SGSSCKFSCD

401 EGFELKGSRR LQCGPRGEWD SEKPTCAGVQ CSSLDLPGKM

441 NMSCSGPAVF GTVCEFTCPE GWTLNGSSIL TCGATGRWSA

481 MLPTCEAPAN PPRPLVVALS VAATSLLTLS SLIYVLKREF

521 WKKAKKFVPA SSCQSLQSFE NYQOPSYII
```

An extracellular E-selectin domain may be used for tolerization of a subject. The extracellular domain of the rat E-selectin provided above includes a sequence of about amino acid 22 to about amino acid 494 and therefore has the following sequence (SEQ ID NO:14).

```
 21                    AWYYNASSEL MTYDEASAYC

41 QRDYTHLVAI QNKEEINYLN STLRYSPSYY WIGIRKVNNV

81 WIWVGTQKPL TEEAKNWAPG EPNNKQRNED CVEIYIQRPK

121 DSGMWNDERC DKKKLALCYT ASCTNTSCSG HGECVETINS

161 YTCKCHPGFL GPKCDQVVTC QEQEYPDHGS LNCTHPFGLF

201 SYNSSCSFSC ERGYVPSSME TTVRCTSSGE WSAPAPACHV

241 VECKALTQPA HGVRKCSSNP GSYPWNTTCT FDCEEGYRRV

281 GAQNLQCTSS GVWDNEKPSC KAVTCDAIPR PQNGSVSCSN

321 STAGALAFKS SCNFTCEHSF TLQGPAQVEC SAQGQWTPQI

361 PVCKASQCEA LSAPQRGHMK CLPSASAPFQ SGSSCKFSCD

401 EGFELKGSRR LQCGPRGEWD SEKPTCAGVQ CSSLDLPGKM

441 NMSCSGPAVF GTVCEFTCPE GWTLNGSSIL TCGATGRWSA

481 MLPTCEAPAN PPRP
```

One example of a mouse E-selectin polypeptide sequence that can be found in the NCBI database is the mouse E-selectin sequence with accession number B42755 (gi: 25295806). This mouse E-selectin sequence is the precursor sequence and is provided below for easy reference (SEQ ID NO:15).

```
  1 MNASRFLSAL VFVLLAGEST AWYYNASSEL MTYDEASAYC

41 QRDYTHLVAI QNKEEINYLN SNLKHSPSYY WIGIRKVNNV

81 WIWVGTGKPL TEEAQNWAPG EPNNKQRNED CVEIYIQRTK

121 DSGMWNDERC NKKKLALCYT ASCTNASCSG HGECIETINS

161 YTCKCHPGFL GPNCEQAVTC KPQEHPDYGS LNCSHPFGPF

201 SYNSSCSFGC KRGYLPSSME TTVRCTSSGE WSAPAPACHV

241 VECEALTHPA HGIRKCSSNP GSYPWNTTCT FDCVEGYRRV

281 GAQNLQCTSS GIWDNETPSC KAVTCDAIPQ PQNGFVSCSH

321 STAGELAFKS SCNFTCEQSF TLQGPAQVEC SAQGQWTPQI

361 PVCKAVQCEA LSAPQQGNMK CLPSASGPFQ NGSSCEFSCE

401 EGFELKGSRR LQCGPRGEWD SKKPTCSAVK CDDVPRPQNG

441 VMECAHATTG EFTYKSSCAF QCNEGFSLHG SAQLECTSQG

481 KWTQEVPSCQ VVQCPSLDVP GKMNMSCSGT AVFGTVCEFT
```

```
521 CPDDWTLNGS AVLTCGATGR WSGMPPTCEA PVSPTRPLVV

561 ALSAAGTSLL TSSSLLYLLM RYFRKKAKKF VPASSCQSLQ

601 SFENYHVPSY NV
```

The mature sequence for this mouse E-selectin extends from about amino acid 22 to amino acid 612. The sequence for this mature mouse E-selectin polypeptide is therefore as follows (SEQ ID NO:16).

```
 22                      WYYNASSEL MTYDEASAYC

41 QRDYTHLVAI QNKEEINYLN SNLKHSPSYY WIGIRKVNNV

81 WIWVGTGKPL TEEAQNWAPG EPNNKQRNED CVEIYIQRTK

121 DSGMWNDERC NKKKLALCYT ASCTNASCSG HGECIETINS

161 YTCKCHPGFL GPNCEQAVTC KPQEHPDYGS LNCSHPFGPF

201 SYNSSCSFGC KRGYLPSSME TTVRCTSSGE WSAPAPACHV

241 VECEALTHPA HGIRKCSSNP GSYPWNTTCT FDCVEGYRRV

281 GAQNLQCTSS GIWDNETPSC KAVTCDAIPQ PQNGFVSCSH

321 STAGELAFKS SCNFTCEQSF TLQGPAQVEC SAQGQWTPQI

361 PVCKAVQCEA LSAPQQGNMK CLPSASGPFQ NGSSCEFSCE

401 EGFELKGSRR LQCGPRGEWD SKKPTCSAVK CDDVPRPQNG

441 VMECAHATTG EFTYKSSCAF QCNEGFSLHG SAQLECTSQC

481 KWTQEVPSCQ VVQCPSLDVP GKMNMSCSGT AVFGTVCEFT

521 CPDDWTLNGS AVLTCGATGR WSGMPPTCEA PVSPTRPLVV

561 ALSAAGTSLL TSSSLLYLLM RYFRKKAKKF VPASSCQSLQ

601 SFENYHVPSY NV
```

An extracellular E-selectin domain may be used for tolerization of a subject. The extracellular domain of the mouse E-selectin provided above includes a sequence of about amino acid 22 to about amino acid 557 and therefore has the following sequence (SEQ ID NO:17).

```
 22                      WYYNASSEL MTYDEASAYC

41 QRDYTHLVAI QNKEEINYLN SNLKHSPSYY WIGIRKVNNV

81 WIWVGTGKPL TEEAQNWAPG EPNNKQRNED CVEIYIQRTK

121 DSGMWNDERC NKKKLALCYT ASCTNASCSG HGECIETINS

161 YTCKCHPGFL GPNCEQAVTC KPQEHPDYGS LNCSHPFGPF

201 SYNSSCSFGC KRGYLPSSME TTVRCTSSGE WSAPAPACHV

241 VECEALTHPA HGIRKCSSNP GSYPWNTTCT FDCVEGYRRV

281 GAQNLQCTSS GIWDNETPSC KAVTCDAIPQ PQNGFVSCSH

321 STAGELAFKS SCNFTCEQSF TLQGPAQVEC SAQGQWTPQI

361 PVCKAVQCEA LSAPQQGNMK CLPSASGPFQ NGSSCEFSCE

401 EGFELKGSRR LQCGPRGEWD SKKPTCSAVK CDDVPRPQNG

441 VMECAHATTG EFTYKSSCAF QCNEGFSLHG SAQLECTSQG

481 KWTQEVPSCQ VVQCPSLDVP GKMNMSCSGT AVFGTVCEFT

521 CPDDWTLNGS AVLTCGATGR WSGMPPTCEA PVSPTRP
```

Another example of a mouse E-selectin polypeptide sequence that can be found in the NCBI database is the mouse E-selectin sequence with accession number NP_035475.1 (gi: 6755452). This mouse E-selectin sequence has the signal sequence and is provided below for easy reference (SEQ ID NO:18).

```
  1 MGWSWIFLFL LSGTASVHSW YYNASSELMT YDEASAYCQR

41 DYTHLVAIQN KEEINYLNSN LKHSPSYYWI GIRKVNNVWI

81 WVGTGKPLTE EAQNWAPGEP NNKQRNEDCV EIYIQRTKDS

121 GMWNDERCNK KKLALCYTAS CTNASCSGHG ECIETINSYT

161 CKCHPGFLGP NCEQAVTCKP QEHPDYGSLN CSHPFGPFSY

201 NSSCSFCCKR GYLPSSMETT VRCTSSGEWS APAPACHVVE

241 CEALTHPAHG IRKCSSNPGS YPWNTTCTFD CVEGYRRVGA

281 QNLQCTSSGI WDNETPSCKA VT
```

When the SEQ ID NO:18 mouse E-selectin sequence does not have the signal sequence, it has the following sequence (SEQ ID NO:19).

```
  1                    W YYNASSELMT YDEASAYCQR

41 DYTHLVAIQN KEEINYLNSN LKHSPSYYWI GIRKVNNVWI

81 WVGTGKPLTE EAQNWAPGEP NNKQRNEDCV EIYIQRTKDS

121 GMWNDERCNK KKLALCYTAS CTNASCSGHG ECIETINSYT

161 CKCHPGFLGP NCEQAVTCKP QEHPDYGSLN CSHPFGPFSY

201 NSSCSFGCKR GYLPSSMETT VRCTSSGEWS APAPACHVVE

241 CEALTHPAHG IRKCSSNPGS YPWNTTCTFD CVEGYRRVGA

281 QNLQCTSSGI WDNETPSCKA VT
```

Sources of E-selectin that can be used with the current invention include E-selectin that has been substantially purified from natural sources, recombinant E-selectin produced in prokaryotic or eukaryotic host cells by methods available in the art, and fragments of E-selectin. Furthermore, small organic molecules or peptides with structures that mimic an immunoreactive portion of E-selectin can also be used.

In some embodiments, the E-selectin is produced by recombinant procedures. For example, a codon-optimized nucleic acid encoding the mouse E-selectin polypeptide with SEQ ID NO:18, with the following sequence (SEQ ID NO:20) can be used for recombinant production of mouse E-selectin.

```
  1 ATGGGTTGGT CCTGGATCTT CCTGTTTCTC TTGTCTGGCA

41 CCGCTAGCGT GCACTCATGG TACTATAACG CCTCGAGTGA

81 GCTTATGACT TACGACGAAG CGTCCGCATA CTGCCAGCGT

121 GATTATACAC ATCTGGTCGC TATTCAAAAT AAGGACGAAA

161 TCAACTACCT CAATTCTAAC TTGAAACACA GCCCCTCATA

201 CTATTGGATT GGAATCCGCA AGGTTAACAA TGTATGGATC

241 TGGGTGGGTA CCGGCAAACC TCTTACCGAG CAAGCCCAGA

281 ACTGGGCGCC AGGAGACOCO AACAATAAGC AAAGGAACGA
```

```
-continued
321  AGATTGTGTC GAGATTTACA TCCAGAGAAC TAAGGATTCG

361  GGTATGTGGA ACGACGAACG ATGCAATAAA AAGAAGCTGG

401  CACTCTGTTA CACAGCTAGT TGCACGAACG CCTCCTGTTC

441  TGGCCATGGA GAGTGCATTG AGACCATCAA CAGCTATACT

481  TGCAAATGTC ACCCCGGTTT CTTGGGCCCT AATTGCGAAC

521  AAGCTGTTAC ATGTAAGCCA CAGGAGCACC CGGATTACGG

561  ATCACTGAAC TGCTCCCATC CCTTCGGTCC TTTTTCGTAC

601  AATAGTTCTT GCAGCTTCGG CTGTAAACGT GGATATCTTC

641  CATCATCCAT GGAAACCACG GTACGCTGCA CTTCGAGTGG

681  TGAGTGGTCT GCGCCGGCCC CCGCATGTCA CGTGGTCGAA

721  TGCGAGGCTC TCACCCATCC TGCCCACGGC ATCAGGAAGT

761  GCAGCTCCAA CCCAGGATCA TACCCCTGGA ACACAACTTG

801  TACCTTCGAC TGCGTTGAAG GTTACAGACG TGTGGGCGCG

841  CAAAATTTGC AGTGTACGTC GTCTGGAATT TGGGACAACG

881  AGACACCTAG TTGCAAGGCT GTCACTTAA
```

Recombinant procedures for production of E-selectin polypeptides can employ expression systems for small or large scale production of E-selectin. Expression systems useful for making E-selectin include, but are not limited to, cells or microorganisms that are transformed with a recombinant nucleic acid construct that contains a nucleic acid segment encoding an E-selectin polypeptide. Examples of recombinant nucleic acid constructs may include bacteriophage DNA, plasmid DNA, cosmid DNA, or viral expression vectors. Examples of cells and microorganisms that may be transformed include bacteria (for example, *E. coli* or *B. subtilis*); yeast (for example, *Saccharomyces* and *Pichia*); insect cell systems (for example, baculovirus in *Spodoptera frugiperda*, Sf9 cells); plant cell systems; or mammalian cell systems (for example, COS, CHO, BHK, 293, VERO, HeLa, MDCK, W138, and NIH 3T3 cells). Also useful as host cells are primary or secondary cells obtained directly from a mammal that are transfected with a plasmid vector or infected with a viral vector. Examples of suitable expression vectors include, without limitation, plasmids and viral vectors such as herpes viruses, retroviruses, vaccinia viruses, attenuated vaccinia viruses, canary pox viruses, adenoviruses, adeno-associated viruses, lentiviruses and herpes viruses, among others. Synthetic methods may also be used to produce polypeptides and peptide fragments of the invention. Such methods are known and have been reported. Merrifield, *Science,* 85:2149 (1963).

In some embodiments, the expression system includes use of Chinese Hamster Ovary (CHO) cells or insect cells as the host cells. The glycosylation with a mammalian cell such as a CHO cell is known to differ from that of an insect expression system such as the baculovirus expression vector system. The difference is that glycosylation of a protein molecule derived from the baculovirus vector inserted into an insect expression system leads to an asparagine attached di-N-acetylglycosamine to which a terminal trimannose is attached. This is termed the paucimannose structure and it facilitates interaction with mannose receptors on antigen-presenting cells. Hence, there may be an advantage in some situations to utilize a baculovirus expression vector system. In other embodiments, a mammalian expression system may be used, where additional N-linked glycans may be attached to the three mannoses of the terminal trimannose (paucimannose) structure generated in the insect expression system. These N-linked glycans include N-acetylglycosamine, galactose, and N-acetylneuraminic acid (also known as sialic acid). Therefore, a variety of host cells can be used to generate E-selectin polypeptides with somewhat different glycosylation patterns. The invention is directed to compositions and methods of using E-selectin with any type of glycosylation, or no glycosylation.

Immune Tolerance

The immune system has the remarkable ability to mount a highly specific response against invading pathogens while ignoring self molecules. This specificity is determined in part by the T lymphocyte, which expresses a randomly generated and unique T-cell receptor (TCR) that recognizes a peptide antigen bound to a major histocompatibility complex (MHC) molecule. MHC molecules can bind both to self peptides as well as to foreign peptides, where the self peptides are from the same organism as the MHC molecules (i.e., the host) and the foreign peptides are from a different, foreign organism. Thus, the specificities of the peripheral TCR repertoire and/or the function of self-reactive T cells must be regulated such that the immune system ignores the self peptides or responds in a way that does not injure the host. The physical elimination of autoreactive T cells during thymocyte development is the primary mechanism used by the immune system to establish such self-tolerance. However, not all self peptides are present in the thymus. Therefore, the immune system must either ignore a tissue-specific self peptide, or develop an active self-tolerance that relies on the suppression, physical elimination, or functional inactivation of mature autoreactive T cells.

The following observations are generally applicable to immune tolerance: (1) tolerance refers to a selective inability of the immune system to respond to antigens and, for purposes of this invention, is a "learned" phenomenon; (2) both foreign and self-antigens can be targets of tolerogenic processes; (3) although tolerance can be mediated by suppressor cells, tolerance is not the same as immune suppression, either mechanistically or clinically; (4) tolerance can be maintained by active or passive processes and can result from cell inactivation, altered cellular function, or cell death; and (5) tolerance can be induced centrally (in the thymus) or peripherally.

According to the invention, immune tolerance is generated by exposure of mucosal surfaces to a tolerizing antigen (here, E-selectin). Immune responses in mucosal tissues are self-limited, and repeated challenge with selected antigens results in a diminished response. Mucosal administration of both high- and low-dose antigen results in immune tolerance, in which the immune response to subsequent systemic administration of antigen is blocked. However, at least two mechanisms of immune tolerance may exist. Tolerance to high-doses of an antigen appears to occur by inactivation or clonal deletion of Th1 and Th2 cells. In contrast, tolerance to low doses of antigen leads to "bystander" immune suppression mediated by stimulation of regulatory cells to produce Th2- and Th3 type cytokines, with interleukin-4 (IL-4), interleukin-10 (IL-10) and TGF-β being the major suppressive cytokines.

Inactivation of T cells by the clonal deletion tolerance mechanism is called clonal anergy and was originally described using a tissue culture system of cloned T cells. Clonal anergy has since been defined as a reversible, induced tolerance state in which the T lymphocyte cannot produce its autocrine growth factor IL-2 or proliferate in response to the antigen it recognizes. In vitro, this unresponsive state is induced by stimulation of the T cell through its TCR in the absence of costimulatory signals, such as those occurring as a result of the interaction of B7 molecules on the antigen presenting cell (APC) with CD28 receptors on the T cell. In the absence of such costimulatory signals, T cells fail to proliferate, and TCR occupancy unaccompanied by proliferation down-regulates the T cell's responsiveness.

Bystander suppression relies on the induction of regulatory cells in mucosal tissues that are specific for the mucosally administered antigen. So called "bystander antigens" cause regulatory (suppressor) T-cells to be induced in the gut-associated lymphoid tissue (GALT), or bronchial associated lymphoid tissue (BALT), or most generally, mucosa associated lymphoid tissue (MALT). MALT includes both GALT and BALT. After migration to the diseased or affected organ, these regulatory cells can be activated by the presence of the antigen, and will secrete immunosuppressive cytokines (IL-4, IL-10, and TGF-β), thereby leading to suppression of ongoing immune responses to the antigen against which tolerance was induced and to unrelated self antigens. Evidence suggests that immune regulation and bystander suppression occur after administration of intermediate or lower antigen doses, whereas clonal deletion or clonal anergy of antigen-reactive lymphocytes generally occurs at high dosages.

IL-4, IL-10 and TGF-β are antigen-nonspecific immunosuppressive factors that suppress immune attack regardless of the antigen that triggers the attack. However, because oral or mucosal tolerization with a bystander antigen only causes the release of these cytokines in the vicinity of autoimmune attack, no systemic immunosuppression ensues. TGF-β is thought to be one of the most important cytokines for bystander tolerance. IL-4 enhances Th2 response (i.e., acts on T-cell precursors and causes them to differentiate preferentially into Th2 cells at the expense of Th1 responses). IL-4 also indirectly inhibits Th1 exacerbation. IL-10 is a direct inhibitor of Th1 responses.

After orally tolerizing mammals afflicted with autoimmune disease conditions with bystander antigens, increased levels of TGF-β, IL-4, and IL-10 are observed at the locus of autoimmune attack (Chen, Y. et al., "Regulatory T cell clones induced by oral tolerance: suppression of autoimmune encephalomyelitis," Science, 265: 1237-1240, (1994)). The bystander suppression mechanism has also been confirmed by von Herrath et al., "Oral insulin treatment suppresses virus-induced antigen-specific destruction of beta cells and prevents autoimmune diabetes in transgenic mice," J. Clin. Invest., 96: 1324-1331, (1996).

According to the invention, inducing E-selectin tolerance has many utilities. For example, it can be used in preventing and treating vascular dementia, strokes and other forms of vascular disease. Additionally, it can be used in treating disorders in which E-selectin has been determined, or may be determined, to play a role, such as, for example, lung injury, psoriasis, contact dermatitis, inflammatory bowel disease, arthritis, and the like. (See, e.g., Washington R., et al., "Expression of immunologically relevant endothelial cell activation antigens on isolated central nervous system microvessels from patients with multiple sclerosis," Ann. Neurol. 35: 89 (1994); Bevilacqua (1989); Bevilacqua and Nelson, "Selectins," J. Clin. Invest. 91: 379 (1993); Koch, et al., "Immunolocalization of endothelial and leukocyte adhesion molecules in human rheumatoid and osteoarthritic synovial tissues," Lab Invest. 64: 313 (1991); Mulligan, et al., "Role of endothelial-leukocyte adhesion molecule 1 (ELAM-1) in neutrophil-mediated lung injury in rats," J. Clin. Invest. 88: 1396 (1991); and Mulligan, et al., "Protective effects of oligosaccharides in P-selectin-dependent lung injury," Nature 364: 149 (1993)).

Vascular Dementia

As indicated above, vascular dementia is a loss of cognitive function as a result of diminished blood flow to the brain. Vascular dementia can arise from diminished blood flow in arteries within the heart and/or in blood vessels leading to the brain. Thus, while vascular dementia can be a result of blockage in blood vessels within the brain, it can also be caused by poor blood flow to the brain. Moreover, while vascular dementia may occur as a result of single event that reduces blood flow from the heart and/or with blood vessels leading to the brain, vascular dementia can also have a slow onset, for example, as a result of progressive decrease in blood flow from the heart to the brain over time.

Vascular dementia can therefore result from ischemic or hemorrhagic brain lesions as well as from lesions that develop elsewhere during protracted hypoperfusion. The subcortical ischemic form of vascular dementia is a common type of vascular cognitive impairment and dementia, and one of the major causes of cognitive decline in elderly people. Subcortical ischemic vascular dementia mainly results from small-vessel disease, which causes lacunes and extensive white matter lesions, and can be compared to large vessel dementia or cortical vascular dementia (Roman G C, Neurology. 1993; 43:250-260, Roman G C Lancet Neurol. 2002; 1:426-436). The ischemic lesions in subcortical ischemic vascular dementia particularly affect the frontal-subcortical circuits, an observation that explains the major cognitive and clinical neurological effects of vascular dementia (Ishii N, Neurology 1986; 36: 340-45, Cummings J L, Arch Neurol 1993; 50:873-80). Subcortical ischemic vascular dementia is also caused by persistent hypertension (de Leeuw F E, Brain. 2002; 125:765-772) and hypoperfusion due to congestive heart failure (Roman G C. Neurol Res. 2004; 26:454-458), atrial fibrillation (de Leeuw F E, Neurology. 2000; 54:1795-1801), and obstructive sleep apnea (Kamba M, J. Neurol. Neurosurg. Psychiatry. 2001; 71; 334-339).

Ischemic white matter lesions, a common finding in elderly people, are the characteristic pathological changes in subcortical ischemic vascular dementia and cognitive impairment, and cognitive dysfunctions are related to lesion severity (Hachinski V C, Arch Neurol. 1987; 4:21-23, Pantoni L, Alzheimer Dis. Assoc. Disord. 1999; 13 (suppl 3):S49-S54, de Groot J C, Neurology 2001; 56:1539-1545). Cerebrovascular white matter lesions constitute the core pathology in several types of vascular dementia, such as Binswanger's disease, cerebral amyloid angiopathy, and cerebral autosomal dominant arteriopathy with subcortical infarcts and leukoencephalopathy (CADASIL). These cerebrovascular white matter lesions are caused by chronic cerebral hypoperfusion, which result from the severe stenosis of several arteries or arterioles mainly in deep white matter (Pantoni L, Stroke 1997; 28:652-659, de Groot J C, Neurology 2001; 56:1539-1545, Roman G C, Neurol. Res. 2004; 26:454-458, Capizzano A A, Am J Neuroradiol 2000; 21:621-630).

Animal models exist for vascular dementia, permitting analysis of the effects of drugs and drug dosages on the development, prognosis and recovery from vascular dementia. In particular, cerebrovascular white matter lesions can be experimentally induced in the rat brains as a result of protracted hypoperfusion induced by the permanent occlusion of both common carotid arteries (Wakita H, Acta Neuropathol. (Bert) 1994; 87: 484-492). In this model, cerebral blood flow decreases to about 40% of the normal blood flow and the gradually increase to about 82% of normal blood flow over extended periods of time (Tsuchiya M, Exp. Brain Res. 89:87-92 (1992): Otori T, Cerebrovasc. Dis. 6 (suppl): 71 (1996); Tomimoto H, Brain Nerve 49:639-644 (1997); Ouchi Y, J Nucl Med. 39:198-202 (1998)). These animals exhibit delayed white matter lesions and memory impairment correlated with the damage of frontal-subcortical circuits. This method of inducing forebrain ischemia can thus be used as a model for vascular dementia (Wakita H, Acta Neuropathol. (Berl) 87: 484-492 (1994); Pappas B A, Brain Res. 708:50-58 (1996); Ohta H, Neuroscience 79:1039-1050 (1997); Wakita H, Brain Res. 924:63-70 (2002)); Sarti C, Behav Brain Res. 136:13-20 (2002)).

Previous studies using this animal model for vascular dementia have demonstrated that CD4- or CD8-positive T cells infiltrate in the neural parenchyma, and that microglia, the immune effector cells of the central nervous system, are activated and express MHC class I and II antigens briefly after ischemia in a manner predictive of the extent and the severity of demyelination and axonal damage (Wakita H, Acta Neuropathol. (Berl) 87: 484-492 (1994); Wakita H, Stroke 26:1415-1422 (1995); Wakita H, Brain Res. 792:105-113 (1998); Wakita H, Neuroreport 14:1461-1465 (1999); Wakita H. Brain Res. 924:63-70 (2002)). The suppression of these activated microglia by immunosuppressive and anti-inflammatory drugs results in an attenuation of the white matter lesions (Wakita H, Stroke 26:1415-1422 (1995); Wakita H, Brain Res. 792:105-113 (1998); Wakita H, Neuroreport 14:1461-1465 (1999); Wakita H., Brain Res. 992:53-59 (2003)). The activation of microglia can also be detected in the early stage of human cerebrovascular white matter lesions, and is associated with degradation of myelin and axonal damage (Suenaga T, Acta Neuropathol (Berl). 87:450-455 (1994); Akiguchi I, Stroke. 28:1423-1429 (1997)). These data suggest that the immunological and inflammatory reactions can augment the white matter damage under chronic ischemia.

As described above, E-selectin, a glycoprotein, is a cell surface-bound leukocyte adhesion molecule specific to endothelial cells (Bevilacqua M P, Science 243 (4895):1160-1165 (1989)). It mediates the interaction between leukocytes, platelets, and the endothelium (Bevilacqua (1989)). Normal resting endothelial cells do not express E-selectin (Pigott R, BBRC 187:584-9 (1992)). The expression of E-selectin is induced in response to proinflammatory cytokines, such as IL-1 and TNF, and its increased surface expression is a reflection of endothelial activation (Bevilcqua M P, Annu. Rev. Immunol. 11:767-804 (1993)). In patients with cerebrovascular disease, including subcortical ischemic vascular dementia, the serum concentration of the soluble isoform of E-selectin is increased (Fassbender K, Stroke 26:1361-1364 (1995); Frijns C J, Stroke 28: 2214-2218 (1997); Fassbender K, Stroke 30:1647-1650 (1999)). The upregulation of E-selectin expression in the ischemic cerebral vasculature has been shown in experimental cerebral ischemia (Wang X, Stroke 26:1665-1669 (1995); Haring H-P, Stroke 27:1386-1392 (1996); Zhang R L, J Cereb Blood Flow Metab. 16:1126-113 (1996); Huang J, Stroke 31:3047-3053 (2000)). Moreover, administration of anti-E-selectin antibody reduces the infarct volume and neurological deficits in murine transient focal ischemia model (Huang J, Stroke 31:3047-3053 (2000)).

In view of these observations, and the results provided herein, vessel activation and E-selectin expression play a pivotal role in the inflammatory process and subsequent tissue injury after cerebral ischemia through leukocyte-endothelial attachment and infiltration of leukocytes.

Thus, a novel method to induce generation of regulatory T cells targeted to activating blood vessels has been developed involving administration of E-selectin to induce mucosal tolerance to that antigen. Mucosal tolerance to E-selectin prevents ischemic and hemorrhagic strokes in spontaneously hypertensive stroke prone rats (Takeda H, Stroke 33:2156-2164 (2002)) and protects against ischemic brain damage after permanent middle cerebral artery occlusion in spontaneously hypertensive stroke prone rats (Chen Y, Proc. Natl. Acad. Sci. U.S.A. 100:15107-12 (2003)). These findings suggest that E-selectin participates in inflammation and immunological responses during and after an ischemic insult and serves to target immunomodulatory regulatory T cells to blood vessel segments that are undergoing endothelial cell activation. As illustrated in a previous application by the inventors U.S. Ser. No. 10/296,423 (filed Jun. 11, 2003, and incorporated herein in its entirety), these regulatory T cells may prevent stroke and protect against ischemic brain damage through "bystander suppression."

Administration

One aspect of the current invention is a method for inducing E-selectin tolerance in a subject. This method involved administering E-selectin to mucosal tissues of a subject. According to the invention any E-selectin that can induce immune tolerance in the subject to E-selectin can be used. Thus, for example, an E-selectin with any of SEQ ID NO:1-26, 30-33 can be used in the methods and compositions of the invention.

Tolerance to an antigen such as E-selectin can be induced by administration to many types of mucosal tissues including oral, nasal, enteral, vaginal, rectal and respiratory mucosa. By reducing enzymatic degradation in the gastrointestinal tract, lower doses of antigen may sometimes be used for nonoral routes of administration. In some embodiments, tolerance is induced by intranasal administration of E-selectin.

Tolerance, including bystander tolerance, can be induced by a single series of E-selectin administrations. Thus, for example, E-selectin tolerance or E-selectin bystander tolerance can be induced by an administration protocol involving a single series of five administrations of E-selectin over a period of two weeks. In other embodiments, this regimen of five administrations over two weeks is repeated at least once. Repeating a series of E-selectin administration is referred to herein a "booster" series of administrations. Thus, a single series of E-selectin dosages is administered within about one to two weeks. The "booster" administrations repeat this series of E-selectin administrations after a period of several weeks without any E-selectin administrations. In some embodiments, this booster regimen is repeated every three weeks for the remainder of the life of the subject.

Dosages, E-selectin sources, formulations, dosage volumes, regimens, and methods for analyzing results aimed at optimizing E-selectin tolerance can vary. Thus, minimum and maximum effective dosages vary depending on the method of administration. Suppression of the clinical and histological changes associated with vascular dementia can occur within a specific dosage range, which, however, varies depending on the organism receiving the dosage, the route of administration, whether E-selectin is administered in conjunction with other co-stimulatory molecules, and the specific regimen of E-selectin administration. For example, in general, nasal administration requires a smaller dosage than oral, enteral, rectal, or vaginal administration.

When E-selectin is administered mucosally, dosages are used that range from about 0.005 to about 500 mg/day, or from about 0.05 to about 50 mg/day. In some embodiments, mucosal dosages are from about 0.5 µg to about 50 mg per administration, or from about 0.5 µg to about 5 mg per administration. In view of the guidelines provided herein, optimization of the dosage necessary for immune suppression involves no more than routine experimentation.

E-selectin formulations of the present invention may comprise inert constituents including pharmaceutically-acceptable carriers, diluents, solubilizing agents, emulsifying agents, salts, and the like, as are available in the art. Preferred E-selectin formulations are intranasal formulations including normal saline solutions, such as, for example, isotonic and physiologically buffered saline solutions and phosphate-buffered saline (PBS) solutions. The total volume of the intranasal formulations is typically less than 1 milliliter, preferably less than 100 μl.

For oral or enteral E-selectin formulations for use with the present invention, tablets may be formulated in accordance with conventional procedures employing solid carriers well-known in the art. Capsules employed for oral formulations to be used with the methods of the present invention may be made from any pharmaceutically acceptable material, such as gelatin or cellulose derivatives. Sustained release oral delivery systems and/or enteric coatings for orally administered dosage forms are also contemplated, such as those described in U.S. Pat. No. 4,704,295, "Enteric Film-Coating Compositions," issued Nov. 3, 1987; U.S. Pat. No. 4,556,552, "Enteric Film-Coating Compositions," issued Dec. 3, 1985; U.S. Pat. No. 4,309,404, "Sustained Release Pharmaceutical Compositions," issued Jan. 5, 1982; and U.S. Pat. No. 4,309,406, "Sustained Release Pharmaceutical Compositions," issued Jan. 5, 1982.

Examples of solid carriers include starch, sugar, bentonite, silica, and other commonly used carriers. Further non-limiting examples of carriers and diluents which may be used in the formulations of the present invention include saline, syrup, dextrose, and water.

E-selectin can also be administered in an aerosol or inhaled form. Examples of formulations for tolerizing agents administered by inhalation are provided in Weiner, H. et al., "Improved treatment of autoimmune diseases by aerosol administration of auto antigens," WO9108760 (1991). The antigens can be administered as dry powder particles or as an atomized aqueous solution suspended in a carrier gas (e.g., air, N.sub.2, and the like).

Dry aerosol in the form of finely divided solid particles of E-selectin that are not dissolved or suspended in a liquid can also be used in the practice of the present invention. E-selectin formulations may be in the form of dusting powders and comprise finely divided particles having an average particle size of between about 1 and 5 microns, preferably between 2 and 3 microns. Finely divided particles may be prepared by pulverization and screen filtration using techniques available in the art. The particles may be administered by inhaling a predetermined quantity of the finely divided or powdered material.

The E-selectin formulations of the present invention may also be administered in soluble form as an aerosol spray using, for example, a nebulizer such as those described in U.S. Pat. No. 4,624,251 issued Nov. 25, 1986; U.S. Pat. No. 3,703,173 issued Nov. 21, 1972; U.S. Pat. No. 3,561,444 issued Feb. 9, 1971; and U.S. Pat. No. 4,635,627 issued Jan. 13, 1971. Other systems of aerosol delivery, such as the pressurized metered dose inhaler (MDI) and the dry powder inhaler (see, e.g., Newman, S. P. in Aerosols and the Lung, Clarke, S. W. and Davia, D. eds. pp. 197-224, Butterworths, London, England, 1984) can be used when practicing the present invention.

One useful animal model for the analysis of E-selectin formulations and their effectiveness in treating or preventing stroke is the stroke-prone and spontaneously hypertensive SHR-SP rat (Okamoto, K. et al., "Establishment of the stroke-prone spontaneously hypertensive rat (SHR)," Circ. Res. (Suppl.) 34, 35: 1 (1974)). SHR-SP rats may be obtained from professor Yukio Yamori, Graduate School of Human and Environmental Studies, Kyoto University, Yoshida Nihonmatsu-cho, Sakyo-ku, Kyoto, 606-8316, Japan. SHR-SP rats typically die of early-onset cardiovascular disease, sometimes as early as 14 weeks of age, although some SHR-SP rats live to more than 56 weeks of age. Frequently, the cardiovascular disease manifests as a stroke in these rats. The occurrence of a stroke in these rats is diagnosed by measuring behavioral status that could be divided into 4 patterns: no abnormalities (grade 1), irritable (grade 2), lethargic (grade 3), akinetic (grade 4) (Yamori, U. et al., Japanese Circulation Journal 46: 274 (1982)).

The brains of SHR-SP rats at the time of death, typically contain numerous infarcts and intraparenchymal hemorrhage areas that can be counted and measured through microscopic analysis of brain sections. Thus, the effectiveness of an E-selectin formulation can be determined by comparing infarct and intraparenchymal hemorrhage numbers and areas in SHR-SP rats that have been treated with control or test E-selectin formulations. The administration regimen can be evaluated in a similar manner. The control formulations can consist of only carrier components or non-specific antigens (e.g., ovalbumin). In addition, the efficacy of a regimen of booster administrations versus a single series of E-selectin administration can be compared. Examples of these procedures and comparisons are disclosed in the Examples section of this specification.

Another useful animal model for the analysis of E-selectin formulations and their effectiveness in treating or preventing vascular dementia involves occlusion of carotid arteries in rats. See, e.g., Sarti et al., *Persistent impairment of gait performances and working memory after bilateral common carotid artery occlusion in the adult Wistar rat*, BEHAVIOURAL BRAIN RESEARCH 136: 13-20 (2002). Thus, cerebrovascular white matter lesions can be experimentally induced in the rat brain as a result of chronic cerebral hypoperfusion. This model is created by permanent occlusion of both common carotid arteries. For example, Wistar rats can be anesthetized, the bilateral common carotid arteries are exposed through a midline cervical incision and the common carotid arteries are double-ligated with silk sutures bilaterally. The cerebral blood flow (CBF) then initially decreases by about 30 to 50% of the control after ligation. The CBF values later range from 40 to 80% of control after about 1 week to about 1 month.

As illustrated herein, white matter rarefaction is detected in rats with occluded carotid arteries after 3 days or more of ligation Microglia and astroglia were activated after arterial occlusion in a manner that predicts the extent and severity of the subsequent white matter damages. A few lymphocytes, labeled with CD4 or CD8 antibodies, can be detected as scattered in the white matter after arterial occlusion. Other pathological changes include axonal damage and demyelination in white matter lesions. Blood-brain barrier disruptions have also been observed as well as increased matrix metalloproteinase activity in white matter lesions. These changes appear very similar to those in human cerebrovascular white matter lesions. Moreover, these results suggest that inflammatory and immunologic reactions play a role in the pathogenesis of the white matter changes.

Such physiological changes are correlated with learning and memory problems in the occluded carotid artery rat model. Thus, the gait performance of rats with occluded arteries declines over time in comparison with baseline. At 60 and 90 days, rats with bilateral common carotid artery occlusion showed decreased performances on object recognition and Y maze spontaneous alternation test in comparison with sham-operated rats. Thus, this rat model of experimental chronic cerebral hypoperfusion by permanent occlusion of the bilateral common carotid arteries exhibited significant learning impairments along with rarefaction of the white matter. This model is a useful tool to assess the effectiveness of E-selectin tolerization on the pathophysiology of chronic cerebral hypoperfusion, and to provide data for determining optimal dosages and dosage regimens for preventing the cognitive impairment and white matter lesions in patients with cerebrovascular disease.

The effectiveness of an E-selectin formulation for treating or preventing vascular dementia can therefore be determined by observing the gait performance, memory, learning abilities and the incidence and severity of white matter lesions in rats with carotid artery occlusions. Similarly, the E-selectin dosage and administration schedule can be adjusted pursuant to the memory and learning abilities of human patients being treated for vascular dementia.

Assessment of the effect of E-selectin formulations on an immune response to E-selectin can also be made, for example, by determining diminution in certain inflammation markers, such as the number of activated T-cell clones directed against activated vascular tissue. Immunological tolerance can be measured by a number of methods that are well-known in the art. In one preferred embodiment, delayed type hypersensitivity (DTH) response can measured in animals by injecting E-selectin, for example, into the footpad or ear flap of an organism to be analyzed and then administering a challenge injection, for example into a footpad or an ear, at a later time, typically more than 1 week later, most preferably 2 weeks later. DTH reactions can be measured after the elicitation injection as the increase in swelling at the site of the antigen rechallenge. Footpad or ear swelling can be measured at, for example, 0, 24 and 48 hr after challenge.

In some embodiments, the optimum dosage of E-selectin is one that induces E-selectin tolerance, for example, bystander tolerance. In other embodiments, the optimum dosage of E-selectin is one that generates the maximum protective effect in preventing vascular dementia, stroke and the like. In other embodiments, the optimum dosage of E-selectin is one generating the maximum beneficial effect on damaged tissue caused by arterial occlusion. An effective dosage causes at least a statistically or clinically significant attenuation of at least one marker, symptom, or histological evidence characteristic of vascular dementia. Markers, symptoms and histological evidence characteristic of vascular dementia include memory loss, confusion, disturbances in axonal transport, demyelination, induction of metalloproteinases (MMPs), activation of glial cells, infiltration of lymphocytes, edema, inflammation and immunological reactions that lead to tissue damage and further vascular injury. Stabilization of symptoms or diminution of tissue damage, under conditions wherein control patients or animals experience a worsening of symptoms or tissue damage, is one indicator of efficacy of a suppressive treatment.

Ascertaining the effective dosage range as well as the optimum amount of E-selectin is accomplished using the teachings of the present application as well as any available teachings in the art. For example, an optimum regimen for administering E-selectin is determined in light of the information disclosed herein and well known information concerning administration of bystander antigens and autoantigens. Routine variation of dosages, combinations, and duration of treatment is performed under circumstances wherein the effects of such variations on the organism can be measured.

For example, dosages for mammals and humans can be determined by beginning with a relatively low dose (e.g., 1 microgram) and progressively increasing the dosage while measuring appropriate responses (e.g., number of TGF-β, IL-4, and/or IL-10 secreting cells; number and activation of immune attack T-cells in the blood (e.g., by limiting dilution analysis and ability to proliferate); and/or disease severity). The optimum dosage provides maximal prevention from vascular dementia or the maximum protection from tissue damage caused by vascular occlusion while minimizing undesirable side effects. Potential side effects include the generation of pathogenic autoantibodies (Hu, W. et al., "Experimental mucosal induction of uveitis with the 60-kDa heat shock protein-derived peptide 336-351," Eur. J. Immunol. 28: 2444 (1998); Genain C. P., et al., "Late complications of immune deviation therapy in a nonhuman primate," Science 274: 2054 (1996)) or a cytotoxic T lymphocyte response that induces autoimmunity (Blanas E., et al., "Induction of autoimmune diabetes by oral administration of autoantigen," Science 274: 1707 (1996)).

An effective dosage causes at least a statistically or clinically significant attenuation of at least one symptom of vascular dementia, or at least a statistically or clinically significant attenuation of the occurrence rate or time to onset of vascular occlusion. The maximum effective dosage of a bystander antigen in humans can be ascertained by testing progressively higher dosages in clinical trials starting with a relatively low dosage, for example 0.5 μg per administration.

Preferred dosages for intranasal instillations are from about 0.5 to about 50 mg per administration, preferably for humans approximately from about 0.5 μg to 5 mg per administration. For rats, one preferred dosage is 5 μg per administration. Preferred aerosol pharmaceutical formulations may comprise, for example, a physiologically-acceptable buffered saline solution containing between about 0.1 mg and about 300 mg, or about 1 mg and about 300 mg of E-selectin.

In some embodiments, E-selectin is administered in a series of administrations. Typically these administrations are spaced apart over a period of 1 to 2 weeks. For example and as further detailed in the Examples, E-selectin can be administered in five intranasal administrations over a two week period. This protocol can involve administering E-selectin every other day for ten days. Preferably, the administration regimen is repeated in booster administrations that are generally administered several weeks apart. In one embodiment, booster administrations are given after every three weeks. Booster administrations may include a series of administrations, as described above for initial administrations.

Cytokine and non-cytokine synergists can be used in conjunction with E-selectin in the present invention to enhance the effectiveness of E-selectin tolerization. Administration "in conjunction with" encompasses simultaneous and sequential administration, as well as administration in combined form or separately. Oral and parenteral use of cytokine synergists (Type I interferons) has been described in Hafler, D. A. et al., "Treatment of autoimmune disease using oral tolerization and/or type 1 interferon," WO9527499 (1995). Administration of Th2 enhancing cytokines is described in Weiner H. L., et al., "Treatment of autoimmune disease using oral tolerization and/or Th2-enhancing cytokines," WO95275000 (1995). For example, IL-4 and IL-10 can be administered in the manner described in Weiner et al. Id.

Non-limiting examples of non-cytokine synergists for use in the present invention include bacterial lipopolysaccharides from a wide variety of gram negative bacteria such as various subtypes of *E. coli* and *Salmonella* (LPS, Sigma Chemical Co., St. Louis, Mo.; Difco, Detroit, Mich.; BIOMOL Res.

Labs., Plymouth, Pa.), Lipid A (Sigma Chemical Co., St. Louis, Mo.; ICN Biochemicals, Cleveland, Ohio; Polysciences, Inc., Warrington, Pa.); immunoregulatory lipoproteins, such as peptides covalently linked to tripalmitoyl-5-glycarylcysteinyl-seryl-serine (P.sub.3 C55) which can be obtained as disclosed in Deres, K. et al. (Nature, 342: 561-564, "In vivo priming of virus-specific cytotoxic T lymphocytes with synthetic lipopeptide vaccine," 1989) or "Braun's" lipoprotein from E. coli which can be obtained as disclosed in Braun, V., Biochim. Biophys. Acta 435: 335-337, 1976; and cholera toxin .beta.-chain (CTB) the synergist ability of which has been described (though not in connection with abatement of autoimmune reaction) by Sun, J-B et al., "Cholera toxin B subunit: an efficient transmucosal carrier-delivery system for induction of peripheral immunological tolerance," Proc. Natl. Acad. Sci. (USA) 91: 10795 (1994). The effective dosage range for noncytokine synergists for mammals is from about 15 ng to about 15 mg per kg weight and preferably 300 ng-12 mg per kg weight. The effective dosage range for oral Type I interferon for mammals is from 1,000-150,000 units with no maximum effective dosage having been discerned. Another active compound that may be useful in combination with E-selectin is methotrexate which is known to cause a marked Th2 immune deviation with greatly increased IL-4 secretion when given on a pulse regimen (Weiner et al., "Treatment of Autoimmune Disease Using Tolerization in Combination with Methotrexate," U.S. Pat. No. 5,935,577 (1999).

Ascertaining the optimum regimen for administering E-selectin and/or the co-stimulatory molecule is determined in light of the information disclosed herein and well known information concerning administration of bystander antigens and autoantigens. Routine variation of dosages, combinations, and duration of treatment is performed under circumstances wherein the effects of such variations on the organism can be measured. The co-stimulatory agent is preferably administered within 24 hours of administration of E-selectin. More preferably, it is administered at the same time as E-selectin. Most preferably, both are administered in a combined oral formulation.

The following examples describe and illustrate the methods and compositions of the invention. These examples are intended to be merely illustrative of the present invention, and not limiting thereof in either scope or spirit. Those of skill in the art will readily understand that variations of the materials used in, and the conditions and processes of, the procedures described in these examples can be used.

EXAMPLE 1

Reduction of Brain Infarcts by Administration of E-Selectin

This Example illustrates the effects of administering E-selectin on reducing the incidence and size of infarcts in the brains of stroke-prone rats. Further information on stroke treatment by E-selectin tolerization can be obtained in a related application, PCT Application Ser. No. PCT/US01/16583, which is incorporated by reference herein in its entirety.

Materials and Methods

Male and female stroke-prone and spontaneously hypertensive (SHR-SP) 8-10 week-old rats were obtained from the NIH colony. Okamoto (1974) Circ. Res. (Suppl.) 34, 35: 1 (1974). At 11 weeks of age, soluble human E-selectin (encoding the following domains: human E-selectin lectin, EGF, CR1, CR2 with a myc peptide tail), ovalbumin or vehicle (PBS) were administered intranasally. Purified human E-selectin was obtained from Protein Design Laboratories (Fremont, Calif.).

E-selectin and control preparations were administered in the following manner: SHR-SP rats were divided into three groups: (1) a saline (PBS) control group, (2) an E-selectin administration group (ES group), and (3) an ovalbumin (OVA) administration group (OVA group). In addition, ES and OVA groups were divided into single (non-booster) and repetitive (booster) administration groups. For the control group, 20 µl of phosphate-buffered saline (PBS) was administered into each nostril every other day for 10 days for a total of 5 administrations. For the ES non-booster group, 2.5 µg E-selectin in 20 µl PBS was administered into each nostril every other day for 10 days for a total of 5 administrations. For the ES booster group, an initial 2.5 µg of E-selectin in 20 µl PBS was administered as above for the non-booster group; additionally, 2.5 µg of E-selectin in 20 µl of PBS was administered intranasally into each nostril every other day for 10 days (3 weeks after the first E-selectin course) and repeated every 3 weeks until the animals were sacrificed. For the OVA non-booster group, 2.5 µg ovalbumin in 20 µl PBS was administered into each nostril every other day for 10 days for a total of 5 administrations. For the OVA booster group, an initial 2.5 µg of ovalbumin in 20 µl PBS was administered into each nostril as above for the non-booster group; additionally, 2.5 µg of ovalbumin in 20 µl of PBS was administered intranasally into each nostril every other day for 10 days (3 weeks after the first ovalbumin course) and repeated every 3 weeks until the animals were sacrificed.

The rats were evaluated for physical and neurological signs of stroke. These evaluations included an assessment of excitement (i.e., piloerection, hyperkinesis), hyperirratibility (i.e., jumping, trying to escape), behavioral and psychological depression (i.e., hypokinesis, hyposthenia, hyporesponsiveness), motion disturbance (i.e., transient episode of repetitive lifting of paws, ataxia, paresis, paralysis), and late symptoms observed near the time of death (i.e., apathy, coma, urinary incontinence). The rats were also monitored by measuring arterial blood pressure, body weight, heart weight, and arterial blood gas using methods available in the art.

Infarcts were evaluated in the following manner. When animals showed signs of cardiac failure, kidney failure, or stroke, they were perfused and their brains were removed for histology and image processing. Sections from 8 predetermined stereotactic levels were cut from each brain (total of 240 sections). The number and area of infarcts or hemorrhages were determined for each section from each animal. Statistical significance of E-selectin administrations was determined by comparing E-selectin groups to control groups by a Cox Proportional Hazards Model.

The animals lived for variable periods from 14 weeks to the termination of the experiment at 56 weeks. Deaths were caused by heart failure and kidney failure secondary to severe hypertension (mean systolic blood pressure 215 mm Hg), as well as by strokes. Average age at time of death and average systolic blood pressure did not differ among the experimental groups.

Results

The experimental group of animals that received E-selectin with booster administrations had a statistically significant reduction in the frequency and area of infarcts compared to control groups (p<0.0001). Mean area of infarcts decreased from between about 6.873 mm$^2$ to about 27.718 mm$^2$ in control and single administration E-selectin groups to about 0.002 mm$^2$ in the E-selectin booster group (i.e., a greater than 99% reduction; see Tables I-IV). Mean number of infarcts decreased from about 3.0 to about 7.3 for control and single administration E-selectin groups to about 0.3 in E-selectin booster groups (i.e., a greater than 91% reduction; see Tables I-IV). Intraparenchymal hemorrhages were absent from the E-selectin booster group, but were present at an average number of from about 3.2 to about 2.3 per brain section analyzed in control and single E-selectin administration groups (see Tables I-IV).

TABLE I

Group OVA Data

| Sample (sex) | Infracts | | Intraparenchymal Hemorrhage | |
|---|---|---|---|---|
| | Number | Area (mm²) | Number | Area (mm²) |
| 1 (female) | 13 | 6.966 | 2 | 0.439 |
| 2 (female) | 0 | 0 | 0 | 0 |
| 3 (female) | 1 | 0.062 | 15 | 0.390 |
| 4 (female) | 19 | 133.850 | 4 | 0.950 |
| 5 (female) | 15 | 70.559 | 1 | 0.02 |
| 6 (female) | 10 | 10.308 | 0 | 0 |
| 7 (female) | 0 | 0 | 0 | 0 |
| 8 (female) | 0 | 0 | 0 | 0 |
| mean | 7.3 | 27.718 | 2.8 | 2.25 |

TABLE II

Group OVAb Data

| Sample (sex) | Infracts | | Intraparenchymal Hemorrhage | |
|---|---|---|---|---|
| | Number | Area (mm²) | Number | Area (mm²) |
| 1 (female) | 0 | 0 | 0 | 0 |
| 2 (female) | 3 | 0.734 | 1 | 4.784 |
| 3 (female) | 21 | 40.502 | 17 | 1.372 |
| 4 (female) | 0 | 0 | 0 | 0 |
| 5 (female) | 0 | 0 | 1 | 0.063 |
| 6 (female) | 0 | 0 | 0 | 0 |
| mean | 4.0 | 6.873 | 3.2 | 1.037 |

TABLE III

Group ES Data

| Sample (sex) | Infracts | | Intraparenchymal Hemorrhage | |
|---|---|---|---|---|
| | Number | Area (mm²) | Number | Area (mm²) |
| 1 (female) | 0 | 0 | 0 | 0 |
| 2 (male) | 0 | 0 | 0 | 0 |
| 3 (female) | 9 | 13.488 | 5 | 0.177 |
| 4 (female) | 14 | 77.909 | 13 | 7.553 |
| 5 (female) | 0 | 0 | 0 | 0 |
| 6 (female) | 1 | 0.012 | 0 | 0 |
| 7 (male) | 0 | 0 | 0 | 0 |
| 8 (male) | 0 | 0 | 0 | 0 |
| mean | 3.0 | 11.426 | 2.3 | 0.966 |

TABLE IV

Group ESb Data

| Sample (sex) | Infracts | | Intraparenchymal Hemorrhage | |
|---|---|---|---|---|
| | Number | Area (mm²) | Number | Area (mm²) |
| 1 (male) | 0 | 0 | 0 | 0 |
| 2 (female) | 0 | 0 | 0 | 0 |
| 3 (female) | 0 | 0 | 0 | 0 |
| 4 (female) | 0 | 0 | 0 | 0 |
| 5 (male) | 1 | 0.003 | 0 | 0 |
| 6 (female) | 0 | 0 | 0 | 0 |
| 7 (female) | 1 | 0.011 | 0 | 0 |
| 8 (male) | 0 | 0 | 0 | 0 |
| mean | 0.3 | 0.002 | 0 | 0 |

EXAMPLE 2

Induction of Tolerance to E-Selectin

This Example provides data showing that tolerance to E-selectin was induced by the intranasal administration protocol of E-selectin described above, which resulted in decreased stroke-related tissue damage.

For this analysis, either E-selectin or control PBS preparations were administered to rats as described in Example 1 for the non-booster groups. Thus, 2.5 µg E-selectin in 20 µl PBS was administered into each nostril every other day for 10 days for a total of 5 administrations.

Fourteen days after intranasal administration to induce tolerization, delayed-type hypersensitivity (DTH) was analyzed by injecting 5 µg of E-selectin in 50 µl of PBS and 50 µl of complete Freund's adjuvant into hindpads (s.q.). Another fourteen days later, the rats were rechallenged by injecting 5 µg E-selectin in 50 µl PBS into the ear. Ear thickness was measured with microcalipers (Mitsutoyo) 48 hours later to assess to degree of tolerization to E-selectin.

Results of the delayed-type hypersensitivity assay demonstrated that intranasal instillation of human E-selectin induced tolerance. Administration of E-selectin intranasally before footpad and ear injection resulted in a significant suppression of ear swelling compared to control groups, as measured with Mitsutoyo microcalipers. In particular, rats "tolerized" with PBS exhibited a an approximate 55% change in ear thickness (about 0.36 mm swelling), while the E-selectin tolerized rats exhibited only about a 20% change in ear thickness (about 0.11 mm swelling). The difference was statistically significant at the $p<0.01$ level.

These data demonstrate that the E-selectin administration protocol used induced tolerance to E-selectin.

EXAMPLE 3

Vascular Dementia Animal Model

This Example provides information about the animal model used for evaluation of vascular dementia and the effects of E-selectin tolerization on vascular dementia.

The experimental model used for vascular dementia was hypoperfusion of Wistar rat brains. In particular, previous work has shown that cerebrovascular white matter lesions can be experimentally induced in the rat brain as a result of chronic cerebral hypoperfusion and that such hypoperfusion leads to impaired memory. See Sarti et al., *Persistent impairment of gait performances and working memory after bilateral common carotid artery occlusion in the adult Wistar rat*, BEHAVIORAL BRAIN RESEARCH 136: 13-20 (2002). This model is created by permanent occlusion of both common carotid arteries as described below.

The animals were anesthetized with 5% isoflurane for induction and 1.5% isoflurane for maintenance in 30% $O_2$/70% $N_2O$ by facemask. The core body temperature was monitored and maintained at 37.0±0.5° C. using a heating pad and a heating lamp. Through a midline cervical incision, both common carotid arteries were exposed and double-ligated with 5-0 silk sutures as previously described by Wakita H., Acta Neuropathol. (Berl) 1994; 87: 484-492. After the operation, the rats were kept in cages with food and water ad libitum. As controls, four animals were subjected to the same surgical procedures without bilateral carotid ligation.

Cerebral blood flow (CBF) after carotid artery occlusion was 30 to 50% of the control several days after ligation. The CBF decreased to values ranging from 40 to 80% of control over a prolonged period (1 week-1 month).

The effects of carotid artery occlusion upon brain tissues are illustrated in FIGS. 6-13 by comparing results for the PBS treated animals, who received bilateral carotid ligation after administration of PBS during the tolerization schedule (shown in FIG. 1), with the sham-operated animals that did not receive bilateral carotid ligation. As shown FIGS. 6-8, white matter becomes rarefied after carotid artery occlusion (compare PBS vs. Sham-operated tissue sections in FIG. 6-7 and graphic summary in FIG. 8).

Figures 9A, 9B, 9C:
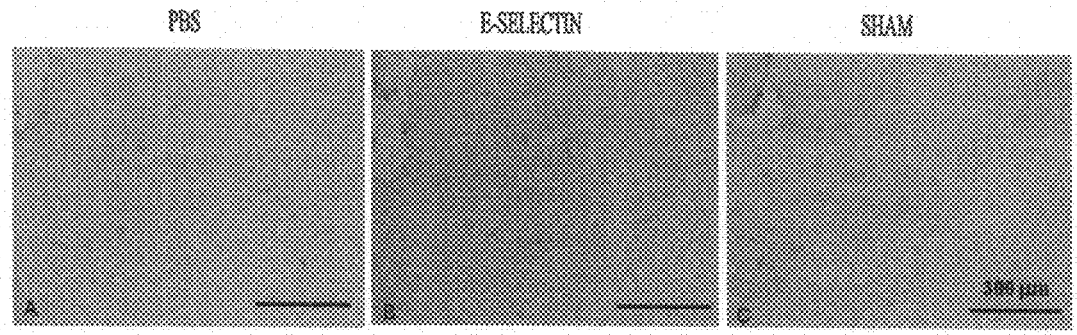
FIG. 9A-F shows photomicrographs of sections immunohistochemically stained for MHC class II antigens from the corpus callosum of rats that were subjected to a sham operation (C, F) or of rats that were subjected to bilateral ligation of the carotid arteries and intranasal PBS (A, D) or E-selectin (B, E) on a booster tolerization schedule. In E-selectin-treated rats, the number of microglia/macrophages positively immuno-labeled for MHC class II antigen in the white matter lesions were somewhat reduced in comparison to PBS-treated animals.
Figures 9D, 9E, 9F:
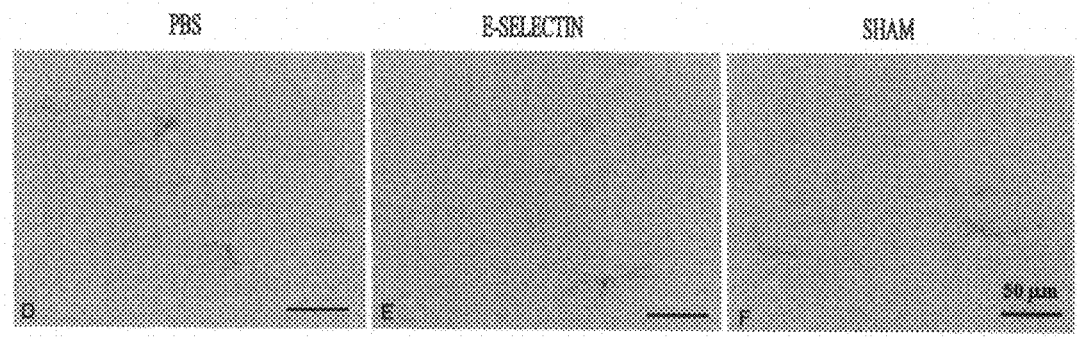

FIG. 9 shows that glial cells become activated in white matter after carotid artery occlusion. In particular, as summarized in FIG. 10, significantly (p=0.177) greater numbers of MHC class II immunopositive microglia are observed in rats who received bilateral carotid ligation ("PBS" rats) than in rats that did not receive bilateral carotid ligation ("Sham" operated rates). Thus, microglia and astroglia were activated briefly after vascular occlusion. Moreover, such activation was predictive of the extent and severity of the subsequent white matter damage.

Figure 11A:
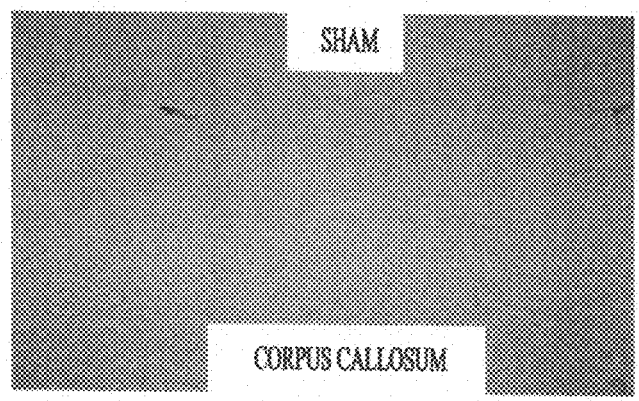
FIG. 11A-B illustrates that CD4 positive T cells infiltrate brain tissues after carotid artery occlusion.
Figure 11B:
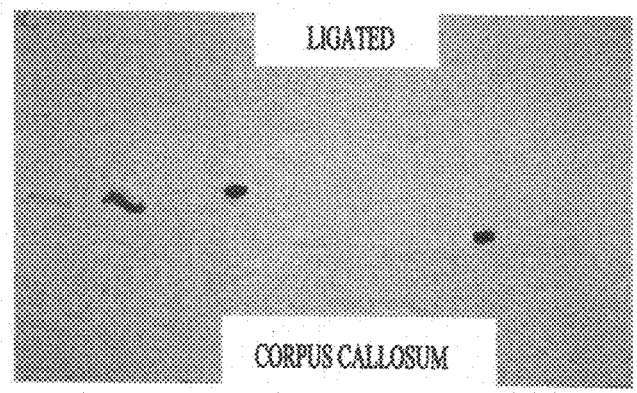

Additional lymphocytes were detected with CD4 or CD8 antibodies (FIG. 4) after occlusion of carotid arteries. As shown in FIG. 11, greater numbers of CD4 positive T cells infiltrated the corpus callosum of rats who received bilateral carotid ligation ("Ligated" rats) than was observed in rats that did not receive bilateral carotid ligation ("Sham" operated rats). These CD4 or CD8 positive T cells were scattered in the white matter after occlusion. These changes are similar to those in human cerebrovascular white matter lesions and suggest that inflammatory and immunologic reactions play a role in the pathogenesis of the white matter changes.

Figures 12A, 12B, 12C:
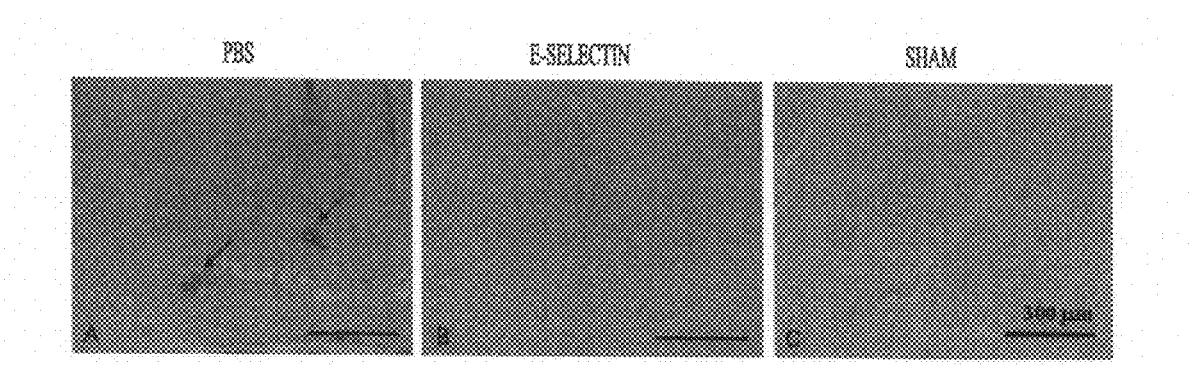
FIG. 12A-F shows photomicrographs of immunohistochemically stained sections for detection of TNF-α in the corpus callosum. The rats were subjected to a sham operation (C, F) or to bilateral ligation of the carotid arteries in animals that also received intranasal PBS (A, D) or E-selectin (B, E) on a booster tolerization schedule. In the E-selectin-treated and sham-operated animals, TNF-immunopositive vessels were markedly less prominent than in PBS-treated animals.
Figures 12D, 12E, 12F:
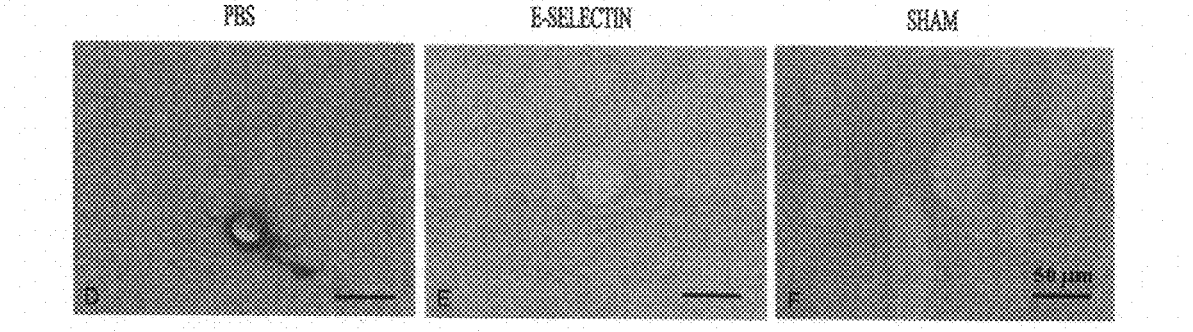

FIG. 12 show that the numbers of TNF-α immunopositive blood vessels increase after carotid artery occlusion. In particular, as summarized in FIG. 13, significantly (p=0.002) greater numbers of TNF-α immunopositive blood vessels are observed in rats who received bilateral carotid ligation ("PBS" rats) than in rats that did not receive bilateral carotid ligation ("Sham" operated rates).

Figure 16:
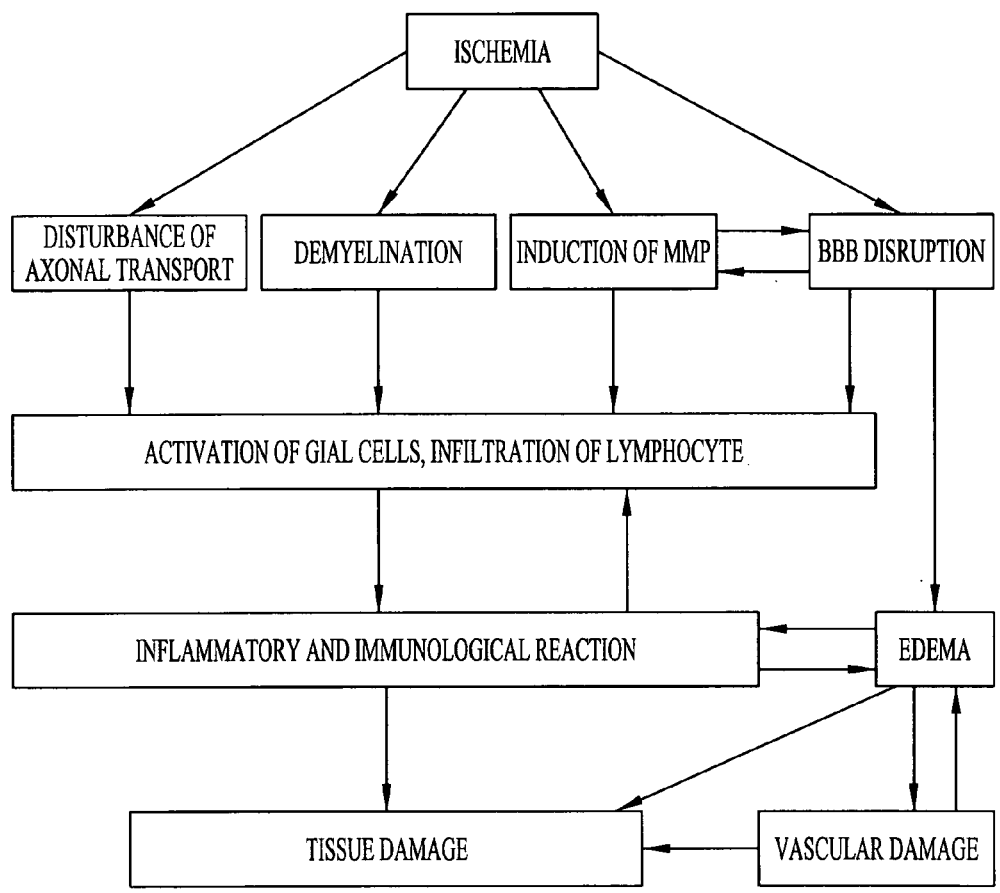
FIG. 16 illustrates that occlusion of blood vessels feeding brain tissues leads to a number of problems, including disturbances in axonal transport, demyelination, induction of metalloproteinases (MMPs), blood brain barrier problems, activation of glial cells, infiltration of lymphocytes, edema, inflammation and immunological reactions that all lead to heightened tissue damage and further vascular injury.

These data indicate that immunological activity accompanies brain damage after carotid artery occlusion. The effects of carotid artery occlusion (ischemia) upon brain function are summarized in FIG. 16.

EXAMPLE 4

E-Selectin Administration Ameliorates Vascular Dementia

This Example illustrates that mucosal tolerization to E-selectin protects against several forms of memory dysfunction and white matter damage in the rat model of vascular cognitive impairment.

Materials and Methods

Animals. A total of 34 Male and female Wistar rats (Charles River Laboratories, Wilmington, Mass., USA) aged 9 weeks were used. The National Institute of Neurological Disorders and Stroke Animal Care and Use Committee approved all experiments.

Tolerization Schedule: Animals were divided into two groups. Intranasal application of E-selectin was carried out with the animals under brief anesthesia with 5% isoflurane in 30% $O_2$/70% $N_2O$. For some experiments E-selectin with SEQ ID NO:30 or SEQ ID NO:31 was used. However, these sequences contain a histidine tag sequence (GGAS-TRAAEQKLI SEEDLNGTRSGHHHHHH (SEQ ID NO:29)), which is used for manufacturing purposes. E-selectin without the histidine tag (e.g., E-selectin with SEQ ID NO:8 or 32, or any of SEQ ID NO:5-8, 18, 19, 30-33) may be more desirable for therapeutic purposes.

Intranasal instillations to animals in groups 1 and 2 were as follows:

(1) Control rats received PBS (Quality biological, Inc, Gaithersburg Md., USA)

(2) Experimental rats received recombinant human E-selectin (Novavax, Rockville Md., USA)

The tolerization schedule involved a single series of administrations or a single series of administrations plus a booster series of administrations as follows (see FIG. 1):

(1) Single or non-booster administration schedule: PBS (20 μl) or E-selectin (2.5 μg/20 μl) was instilled into each nostril every other day for 10 days (total of 5 administrations) (FIG. 1).

(2) Booster administration schedule: intranasal instillations of the same substance at the same volume and concentration on the same schedule as described for the single or non-booster schedule described above, but the administrations were repeated at 3-week intervals from 1 month before surgery to 3 months after surgery (FIG. 1).

Delayed-Type Hypersensitivity Reaction: For assessing the delayed-type hypersensitivity reaction, a single-course tolerization schedule with either PBS or E-selectin was conducted (n=4) (as shown in FIG. 1 for the non-booster group). Fourteen days later, the animals were immunized (hind footpad) with 75 μg E-selectin/200 μl PBS plus 50 μl complete Freund's adjuvant (Sigma, St. Louis, Mo.). Fourteen days after that, ear thickness was measured and the animals were re-challenged with 75 μg E-selectin/100 μl PBS injected into the ear. Ear thickness increase over baseline was measured with microcalipers (Mitsutoyo Co, Ltd, Kawasaki, Kanagawa, Japan) 2 days later.

Surgery: The booster tolerization schedule was repeated at 3-week intervals from 1 month before the surgery to 3 months after the surgery. In order to adjust the surgery workload, half of the rats from each group were randomly selected and subjected to the surgery 3 days after the last dose of the first booster tolerization schedule; and surgery was performed 4 days after the last dose of the first booster tolerization schedule for the remaining half of rats.

The animals were anesthetized with 5% isoflurane for induction and 1.5% isoflurane for maintenance in 30% $O_2$/70% $N_2O$ by facemask. The core body temperature was monitored and maintained at 37.0±0.5° C. using a heating pad and a heating lamp. Through a midline cervical incision, both common carotid arteries were exposed and double-ligated with 5-0 silk sutures as previously described by Wakita H., Acta Neuropathol. (Berl) 1994; 87: 484-492. After the operation, the rats were kept in cages with food and water ad libitum. As controls, four animals were subjected to the same surgical procedures without bilateral carotid ligation.

Behavioral assessment: Behavioral assessment consisted of object recognition, T-maze spontaneous alternation, and T-maze left/right discrimination memory retention tests. An observer who was blind to the treatments performed behavioral assessment.

Object Recognition test. This test evaluates non-spatial working memory related to the frontal subcortical circuits (Ennaceur A. Behav Brain Res 1988; 31:47-59, Sarti C, Behav Brain Res. 2002; 136:13-20). The apparatus was formed by a glass box (30×60×30 cm). The apparatus was illuminated by a 100 W lamp suspended 70 cm above the box in a darkened room. The day before testing, rats were habituated to the test environment by exploring the box for 6 min without objects. On the day of the test, a session of two trials was given. The inter-trial interval was 60 min.

In the first trial, two identical objects were placed on the centerline of the long axis of the floor, 5 cm from each end of the apparatus. Rats were placed into the center of the box and allowed to explore the two objects for 6 min. The amount of time spent exploring each object was recorded. During the second trial, one of the objects presented in the first trial is replaced by a novel object and rats are left in the box for 6 min. The time spent for the exploration of the familiar (Tf) and the novel object (Tn) is recorded separately. Exploration is considered sniffing at the object within a distance of 2 cm from the object and/or touching it with the nose. A discrimination index (Tn−Tf/Tn+Tf) is calculated.

For each animal, one pair of objects in the first trial was selected at random from a set of three plastic objects that differed in shape and color (red cubes, green pyramids, and blue cylinders of 6 cm height), and the role (familiar and novel object) and the position of the two objects in the second trial were randomly changed to avoid object and place preference. After each exposure, the apparatus and the objects were cleaned carefully with 70% alcohol to avoid olfactory stimuli.

T-maze spontaneous alternation: This test evaluates spatial working memory related to the frontal subcortical circuits (Bartolini L., Pharmacol Biochem Behav. 1992; 43:1161-1164, Sarti C, Behav Brain Res. 2002; 136:13-20). Spontaneous alternation was investigated in an acrylic T shaped runway. It consisted of a start box (20×18 cm) and start arm (60 cm long), and two identical goal arms (both 50 cm long). All arms were 10 cm wide and 10 cm high. Spontaneous alternation refers to the instinctive behavioral tendency by which rats typically alternate their choices between the arms of the T-maze more often than they repeat their initial choice. Rats were placed in the start box of the T-maze and a maximum time of 5 min was allowed for them to explore the maze. Spontaneous alternation was defined as following: the rat entered with all four feet into one goal arm, came back, and then entered with all four feet into the opposite goal arm. The number of rats who alternated was recorded.

T-maze left/right discrimination memory retention: This test evaluates spacial reference memory related to the hippocampus and caudoputamen (Oliveira M G, Neurobiol Learn Mem 1997; 68:32-41). This test was repeated at 2, 6 and 10 weeks after surgery. The dimensions of the T-maze apparatus were described above. The exit of the start box and the entrances of the goal arms could be blocked by guillotine doors. Careful consideration was given to avoid providing the animals with any spatial cues. To minimize olfactory cues, the maze was wiped carefully after each run with 70% alcohol.

Training sessions for left/right discrimination memory retention. The day before training, after the spontaneous alternation test, rats were habituated for 15 min to the presence of food pellets (Bacon Softies; Bio-Serv, Frenchtown, N.J., USA) placed at the end of each arm in the T-maze. On days 1 to 3, the rats were food-deprived for 8 to 12 hours each day before the T-maze left/right discrimination training. This training consisted of 3 stages. In the performance of the training, half of the rats from each group were randomly selected and reinforcement (food reward) placed on the right arm; for the other half of the rats from each group, the reinforcement was placed on the left arm. The reinforced arm then remained consistent throughout the training period. The first stage consisted of 5 trials. In this stage, a guillotine door was placed to close off one arm, and the animal was forced to enter the open arm, which was baited with a food reward that the animal was allowed to eat. For all runs the animals remained on the maze until 2 min had elapsed; they were then placed in the start box for 2 min. The second stage consisted of 5 trials. In this stage, a guillotine door was placed to close off the same arm as that in the first stage, and the animal was forced to enter the open arm, which was not baited with a food reward. When the animal entered into the open arm, a food reward was given and the animal was allowed to eat the food. The animals remained on the maze for 2 min and were then placed in the start box for 2 min. In the third stage, a guillotine door was removed, and the animal could enter into either arm (correct side and incorrect side). If the animal chose the arm on the correct side the animal received a food reward and was allowed to eat for 2 min after which it was placed in the start box for 2 min. If the animal chose the incorrect side-arm, the animal was picked up immediately and placed in the start box for 2 min. The third stage was continued until the animals made 4 consecutive correct choices or until they had had 20 training sessions (the training ceiling). This procedure was performed daily on three successive days (on days 1 to 3).

Left/right discrimination memory retention test session. The retention of left/right discrimination memory was evaluated at 1, 2, 3, 5, 7, 10 and 14 days after the training session. The animals were given 10 trials on each testing day. An entry was defined as all four paws entering the arm. The total number of correct entries was recorded.

Histopathology: At 90 days after surgery, the animals were deeply anesthetized with sodium pentobarbital (100 mg/kg, intraperitoneally), perfused transcardially with 0.01 M PBS, and then perfused with a fixative containing 4% paraformaldehyde in 0.1 M phosphate buffer (PB, pH 7.4). Coronal brain blocks including the caudoputamen or optic nerve were embedded in paraffin for histological examination. Two micrometer-thick paraffin sections were then cut on a microtome. The luxol fast blue stain was used to evaluate the myelin damage. Immunocytochemistry with the cocktail of monoclonal antibodies directed against non-phosphorylated neurofilaments (SMI 311, Covance Research Products, Inc., Berkeley, Calif., USA) was used for the assessment of axonal injury (Rosenfeld J, J Neuropathol Exp Neurol. 46:269-282 (1987)). The sections were incubated for 1 hr in 0.1 M PBS containing 0.3% Triton X-100 for permeabilisation. Ten percent donkey serum was applied for blocking followed by incubation overnight in primary antibody (SMI 311) in a dilution of 1:500. The sections were subsequently incubated with a biotinylated anti-mouse IgG raised in donkey (Jackson Immuno Research Labs, West Grove, Pa., USA, 1:2000) for 1 hr, and then incubated with an avidin-biotin peroxidase complex solution (Vector Laboratories, Burlingame, Calif., USA, 1:100) for 1 hr. After each incubation, the sections were rinsed for 30 min with 0.1 M PBS containing 0.3% Triton X-100. The immunoreaction products were visualized with diaminobenzidine (DAB kit, Vector Laboratories, Burlingame, Calif., USA). The severity of the white matter lesions was evaluated by the fiber density of luxol fast blue-stained sections. Monochromatic photo images of both sides of the corpus callosum, the traversing fiber bundles of the caudoputamen bilaterally and both optic nerves were taken by means of a microscope with a ×40 objective connected to a digital camera (MetaMorph Image Processing System, Universal Imaging Corp, Downingtown, Pa., USA). These images were converted into PICT files by Photoshop (Adobe Systems Incorporated, San Jose, Calif., USA) and the fiber density of each PICT file was analyzed with the NIH image computer program. To account for the variation of the fiber density between right and left sides of the corpus callosum and caudoputamen, the average of the fiber densities of both sides was calculated.

For free-floating immunohistochemistry, the rest of the coronal blocks were post-fixed for 12 hrs in 4% paraformaldehyde in 0.1 M PB (pH 7.4), and stored in 20% sucrose in 0.1 M PB (pH 7.4) until used. Serial sections (20 µm thick) were then cut on a cryostat. Endogenous peroxidase was inactivated by immersing the sections in a solution of 0.3% hydrogen peroxide in 10% methanol/0.1 M PBS for 30 min. To block nonspecific staining, sections were incubated in 5% normal horse serum in 0.1 M PBS containing 0.3% Triton X-100 for 1 hr. After blocking, the sections were incubated overnight with the following antibodies (mouse or goat anti-rat) (dilutions in parentheses): against the major histocoinpatibility complex (MHC) class II (Ia) antigen (OX 6, Serotec, Raleigh, N.C., USA, 1:100), against TNF (YC032, Yanaihara Institute, Fujinomiya, Shizuoka, Japan 1:800) and against E-selectin (R and D systems, Minneapolis, Minn., USA 50 µg/ml). The sections were subsequently incubated with a biotinylated anti-mouse IgG or a biotinylated anti-goat IgG (Vector Laboratories, Burlingame, Calif., USA, 1:200) for 1 hr, and then incubated with an avidin-biotin peroxidase complex solution (Vector Laboratories, Burlingame, Calif., USA, 1:100) for 1 hr. After each incubation other than that for blocking nonspecific staining, the sections were rinsed for 15 min with 0.1 M PBS containing 0.3% Triton X-100. Finally, the immunoreaction products were visualized with diaminobenzidine (DAB kit, Vector Laboratories, Burlingame, Calif., USA). For assessment of nonspecific staining, primary antibodies were replaced with normal mouse or goat IgG. We counted the numerical density of the MHC class II (Ia) antigen immunopositive microglia/macrophages in a 0.75 mm$^2$ area in the corpus callosum and the number of TNF or E-selectin immunopositive vessels in the total area of the corpus callosum in a section at a level of −2.3 mm from bregma. To evaluate the hippocampal damage, 20 micrometer-thick frozen sections including hippocampus were stained with cresyl violet.

Immunoassay: The level of plasma TNF concentration was measured by a Rat TNF US ELISA kit (BioSource International, Camarillo, Calif., USA) following the manufacturer's instructions. The O.D. values (450 nm) were measured by SpectraMax M5 (Molecular Devices, Sunnyvale, Calif., USA) and the concentration of the plasma TNF was calculated.

Statistical analysis. Data are represented as mean ±SD. Differences in the mortality rates between groups were determined by Fisher's exact probability test. Differences in the change of ear thickness between the groups were determined by unpaired Student's t-test. Differences in proportions of the T maze spontaneous alternation among each of the three groups were determined by $\chi^2$ test. Differences in the discrimination index of the object recognition test and the percentages of correct arm entries on the T-maze left/right discrimination memory retention test among the groups were determined by repeated measure analysis of variance (ANOVA) followed by post-hoc testing with Fisher's protected least significant difference procedure. Differences in the fiber densities were determined by two-factor ANOVA followed by Fisher's protected least significant difference post-hoc testing. Differences in the numerical densities of either the MHC class II antigen immunoreactive microglia/macrophages, the TNF immunoreactive vessels or E-selectin immunoreactive vessels and in the level of plasma TNF concentration were determined by one-factor ANOVA followed by Fisher's protected least significant difference post-hoc testing. To evaluate the possible effect of optic nerve damage on the object recognition test, a Pearson correlation coefficient was calculated between the fiber density of the optic nerve and discrimination index in the E-selectin treated animals. $p<0.05$ was considered significant.

Results

Mortality rates: None of the sham-operated animals died. Of the 111 animals that received E-selectin, 2 animals (18.2%) died within 7 days after surgery, one animal (9.1%) died by the anesthesia for the nasal instillation of E-selectin at 9 weeks after surgery. Of the 11 animals that received PBS, 4 animals (27.3%) died within 7 days after surgery. There was no significant difference in the mortality rates between the E-selectin and PBS groups.

Cerebral blood flow (CBF) without E-Selectin tolerization: Cerebral blood flow (CBF) was 30 to 50% of the control several days after ligation. The CBF decreased to values ranging from 40 to 80% of control over a prolonged period (1 week-1 month).

Delayed-type hypersensitivity after E-selectin treatment. A single course of tolerization with E-selectin significantly suppressed the ear swelling in the delayed-type hypersensitivity study (p=0.0255). FIG. 2 shows that rats treated with E-selectin had an ear thickness of slightly less than 0.05 mm whereas control rats that received only PBS had an ear thickness of almost 0.07 mm. These data indicate that rats treated with E-selectin became tolerized to later E-selectin administration in the ear flap and therefore did not exhibit as much inflammation and swelling.

Behavioral Assessment

As described in more detail below, tolerization with E-selectin significantly improved the learning and memory impairment in the object recognition test (FIG. 3), T-maze memory retention (FIG. 5) and the ability to handle changes in the T-maze (FIG. 4), compared with the control group of rats that received only PBS.

Neurological impairment without E-Selectin tolerization: Gait performance declined over time in comparison with baseline. At 60 and 90 days, bilateral common carotid artery occlusion rats showed decreased performances on object recognition and T maze spontaneous alternation test in comparison with sham-operated rats.

Object recognition test: There were no significant differences in the discrimination index among the E-selectin, PBS and sham groups before surgery (baseline).

Figure 3:
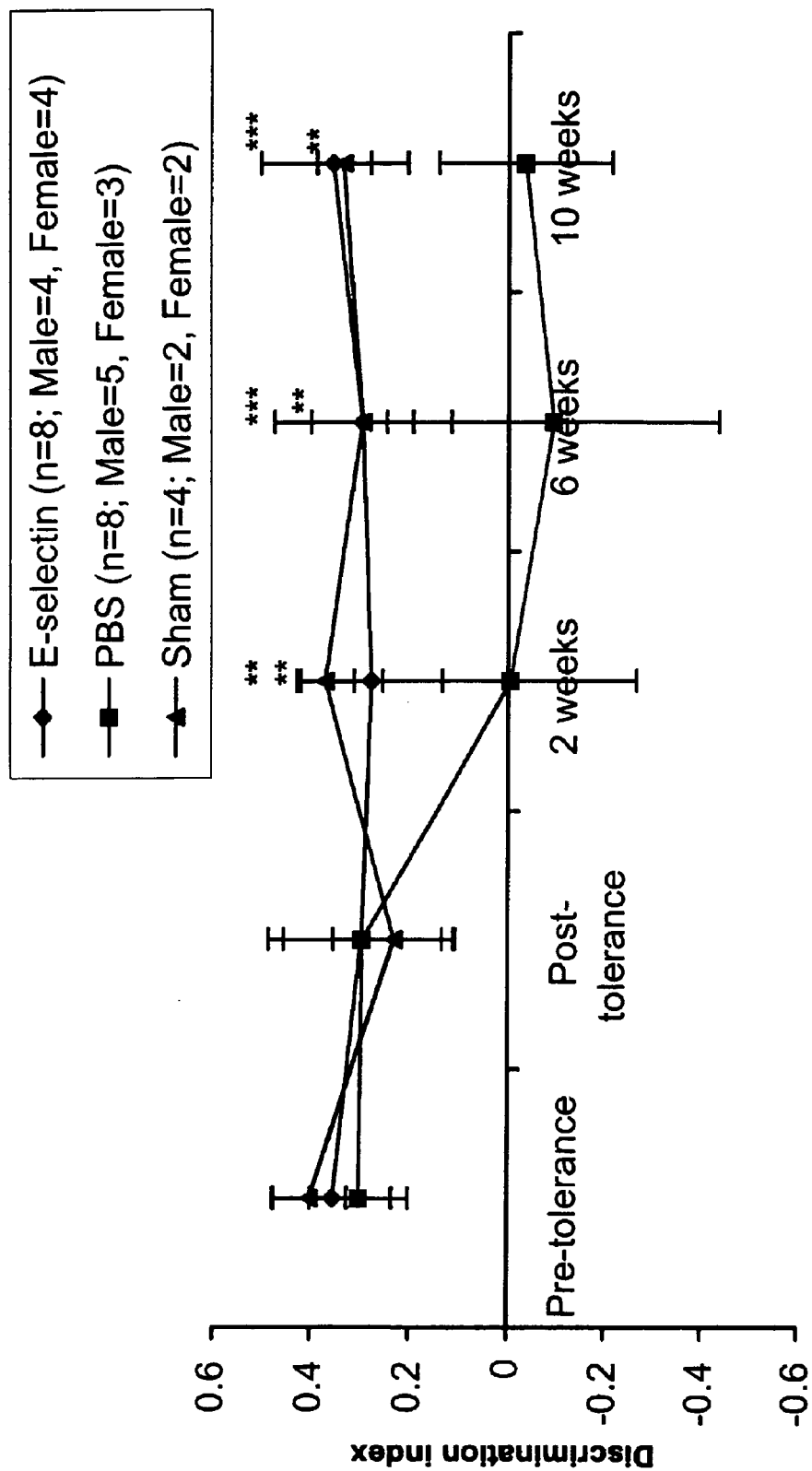
FIG. 3 graphically illustrates the discrimination indices of E-selectin tolerized and non-tolerized rats for the object recognition test. The discrimination indices of the E-selectin and sham groups were significantly increased as compared with the PBS group. *: $p<0.05$, : $p<0.01$, *: $p<0.001$ by Fisher's protected least significant difference procedure, as compared to PBS-treated animals.

After surgery, the PBS group developed a reduced discrimination index. In contrast, the discrimination indices of the E-selectin and sham groups were maintained at the same baseline levels throughout the experiment. The discrimination indices of the PBS group were significantly decreased as compared with the E-selectin and sham groups (p=0.0005, p=0.0059 respectively). There were no significant differences in the discrimination index between the E-selectin and the sham groups (p=0.7397). Thus, induction and maintenance of mucosal tolerance to E-selectin protected against the decrease in discrimination observed in the PBS group. (FIG. 3).

T-maze spontaneous alternation: There were no significant differences in the percentage of spontaneously alternating rats among the E-selectin, PBS and sham groups before surgery and at 2 and 6 weeks after surgery.

Figure 4:
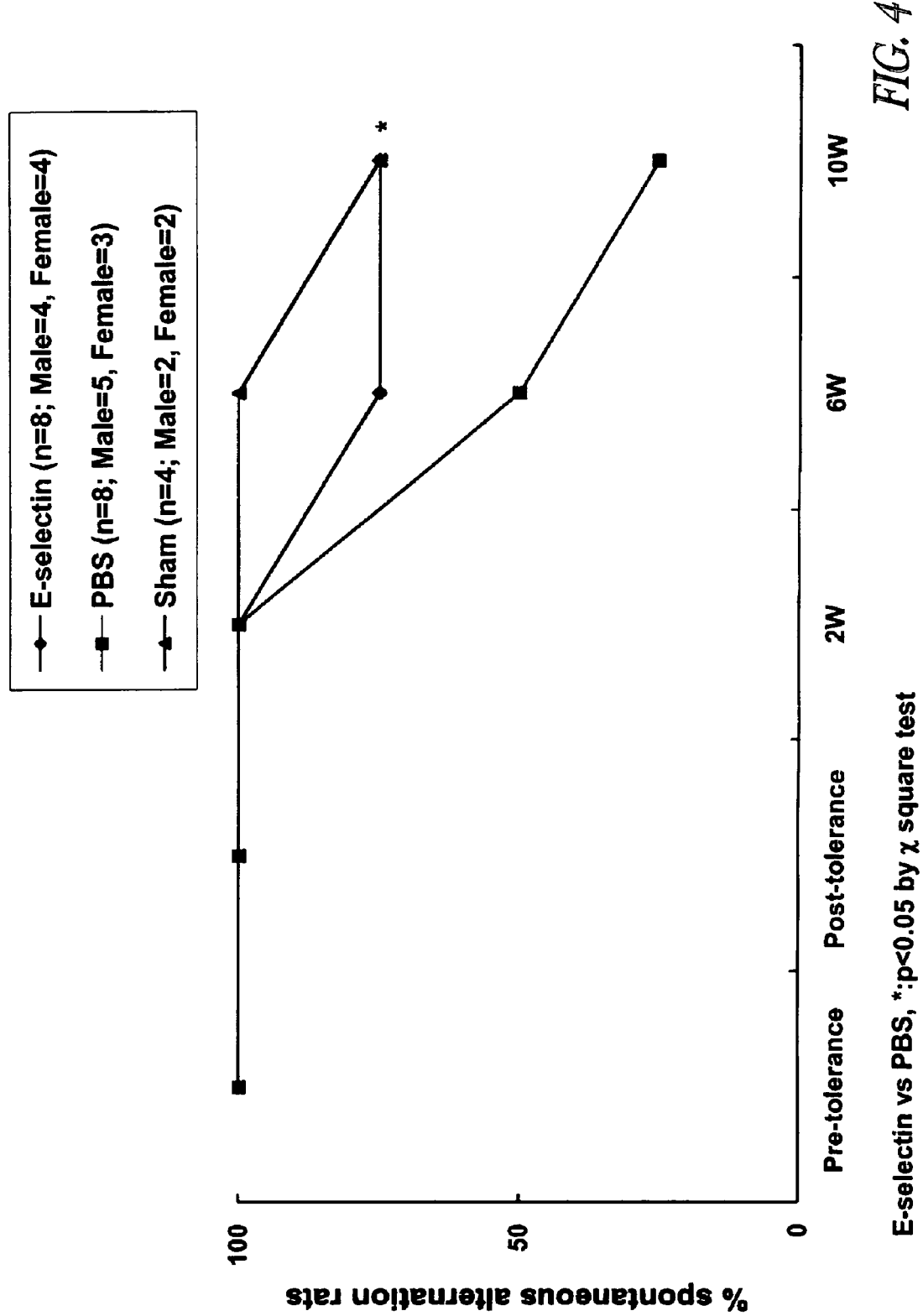
FIG. 4 graphically illustrates of the percent of alternation by rats on the T-maze spontaneous alternation test. Rats have an instinctive behavioral tendency to alternate their choices between the arms of the T-maze more often than they repeat their initial choice. In the E-selectin-treated animals, the percent of rats that alternated was significantly increased at 90 days, as compared with the PBS-treated animals. *: $p<0.05$ by $\chi^2$ test.

However, by 10 weeks after surgery, the percentage of spontaneously alternating rats in the PBS group was significantly decreased compared with the E-selectin group ($p<0.05$). Thus mucosal tolerization to E-selectin protected against loss of the spontaneous alternation tendency seen in PBS tolerized rats. (FIG. 4).

T-Maze Left/Right Discrimination Memory Retention

Figure 5A:
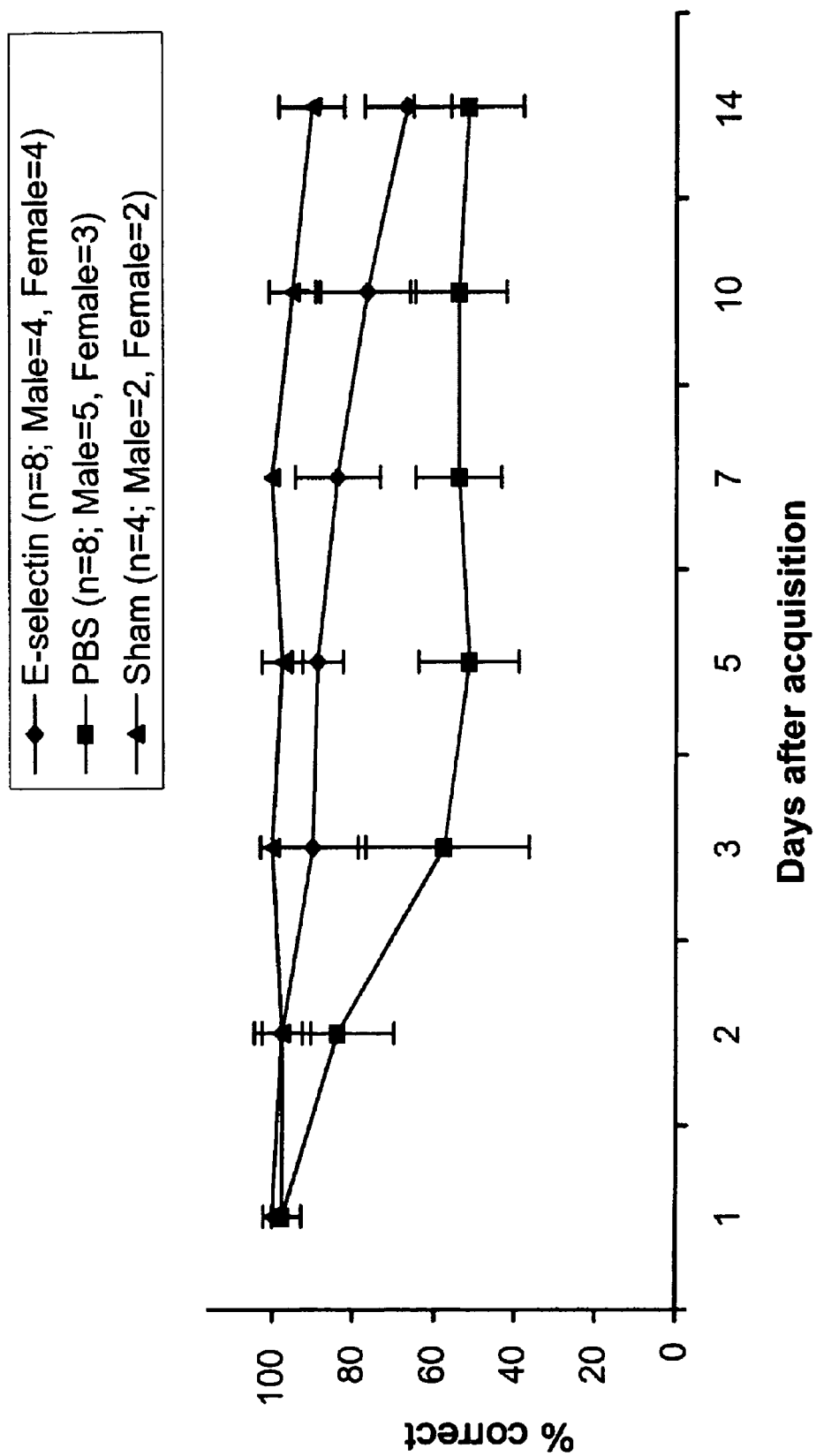
FIG. 5A-C graphically illustrates the percentages of correct arm entrance on the T maze left/right discrimination memory retention test.

Two weeks after surgery: The numbers of correct arm entries did not differ among the E-selectin, PBS and sham groups tested 1 day after the training session. The percentages of correct arm entries were greater than 95%. However, in the PBS group, the number of correct arm entries decreased over time, and the percentage of correct entries between 3 and 14 days after the training session were diminished to 50 to 60%, which is close to a random choice level. This suggests that animals in this group had lost their left/right discrimination memory. The decrease in the number of correct arm entries was less prominent in the E-selectin group, and rats treated with E-selectin had a statistically significantly higher number of correct entries than the PBS-treated animals by repeated measure ANOVA ($p<0.0001$). In contrast with the PBS and E-selectin groups, the sham group retained their left/right discrimination memory at the same level throughout the experiment. The difference between the sham and the PBS groups was statistically significant ($p<0.0001$), and the difference between the sham and the E-selectin groups was also statistically significant by repeated measure ANOVA ($p=0.0040$) (FIG. 5A).

Figure 5B:
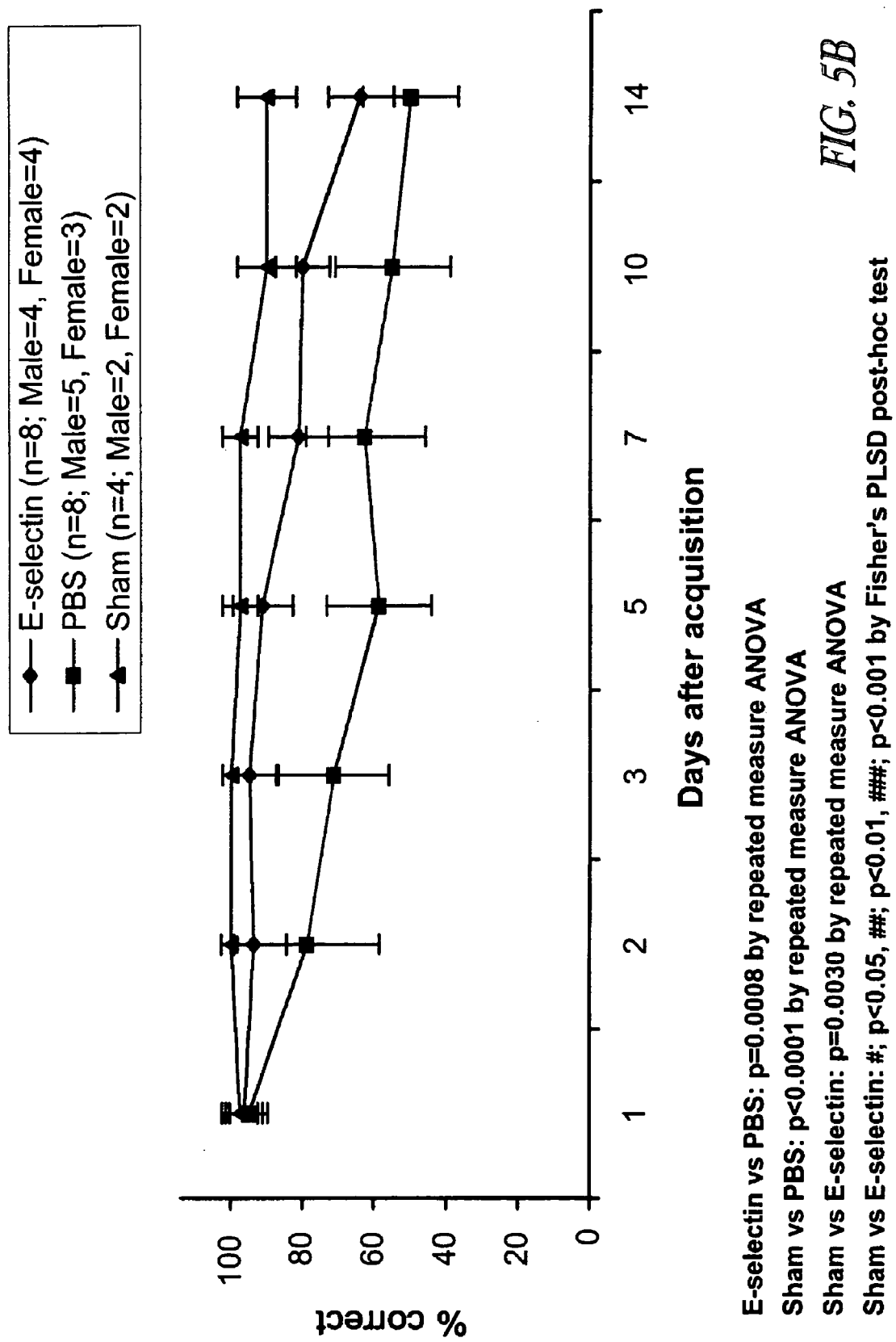

Six weeks after surgery: The E-selectin group had a higher number of correct entries than the PBS group by repeated measure ANOVA ($p=0.008$) (FIG. 5B). However, the difference between sham and E-selectin groups was still statistically significant by repeated measure ANOVA ($p=0.0030$) (FIG. 5B). The difference between sham and PBS groups was also statistically significant ($p<0.0001$). Hence, at six weeks, E-selectin tolerization had not completely ameliorated the effects of carotid ligation.

Figure 5C:
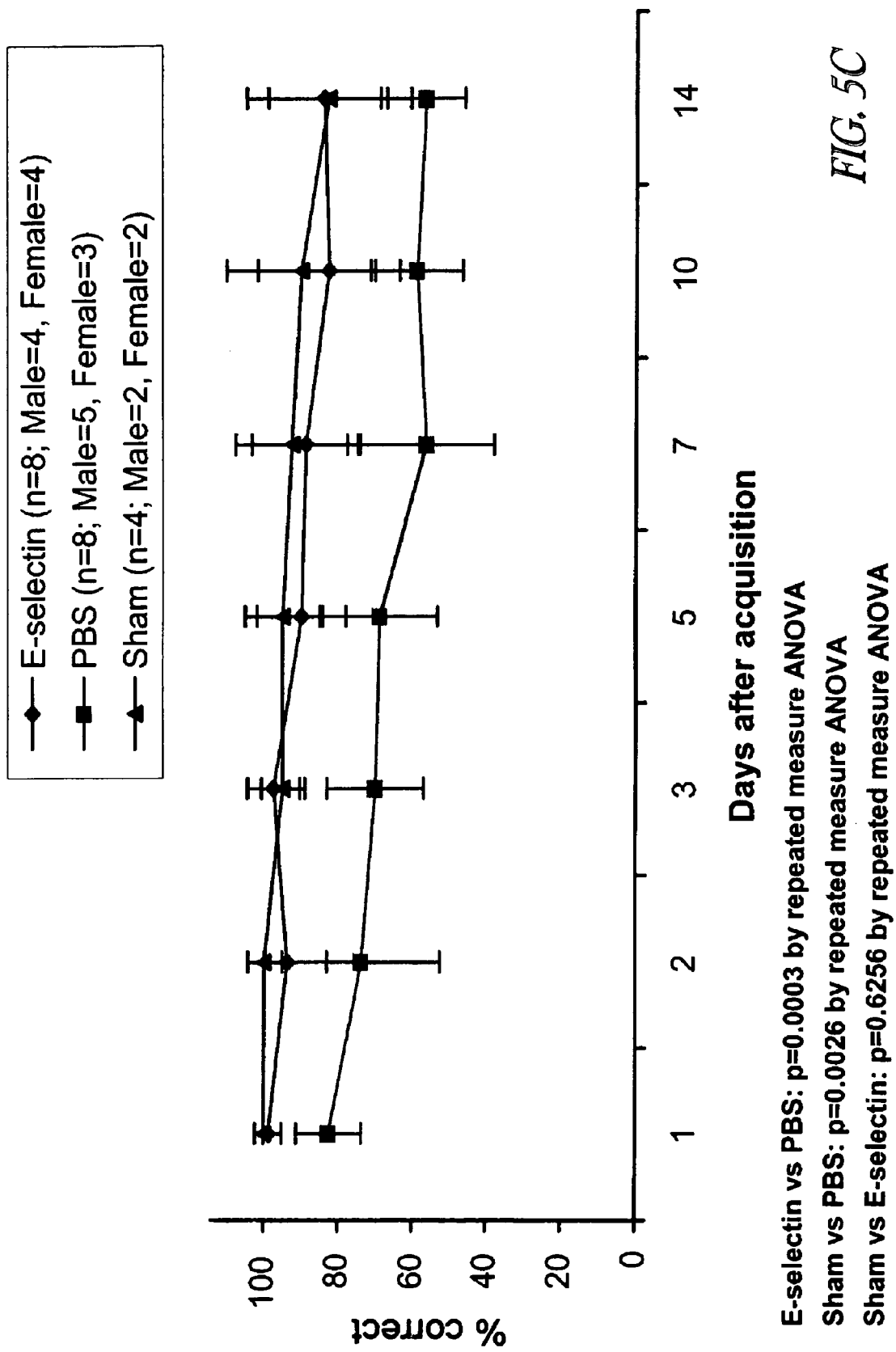

Ten weeks after surgery: In contrast with 2 and 6 weeks after surgery, the sham and the E-selectin groups both retained their left/right discrimination memory throughout the experiment, and there were no significant differences in the number of correct entries between these two groups by repeated measure ANOVA ($p=0.6256$). The E-selectin and sham groups had a higher number of correct entries than the PBS group by repeated measure ANOVA ($p=0.0003$, and $p=0.0026$, respectively) (FIG. 5C). Thus, mucosal tolerance to E-selectin led recovery of the spatial reference memory in left/right discrimination tasks.

Figures 6A, 6B, 6C:
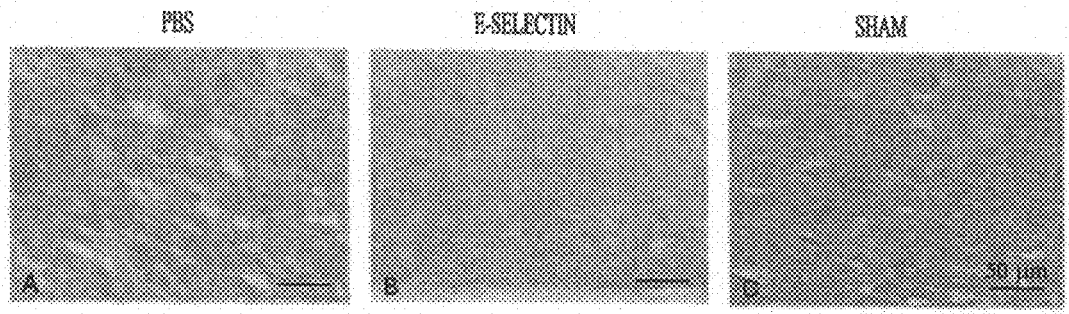
FIG. 6A-I shows photomicrographs of luxol fast blue stained sections of the corpus callosum (A, B, C), caudoputamen (D, E, F) and optic nerve (G, H, I) from rats that were subjected to a sham operation (C, F, I) or to bilateral ligation of the carotid arteries in animals that also received intranasal PBS (A, D, G) or E-selectin (B, E, H) on a booster tolerization schedule. Note that the extent of the white matter rarefaction was less severe in the E-selectin treated and sham-operated rats as compared with PBS group.
Figures 6D, 6E, 6F:
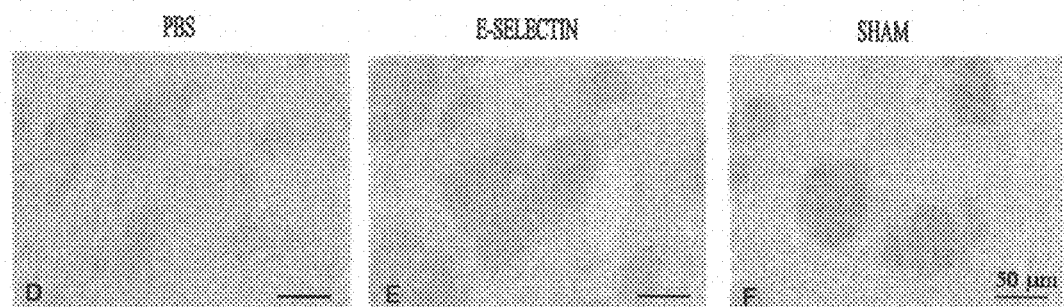
Figures 6G, 6H, 6I:
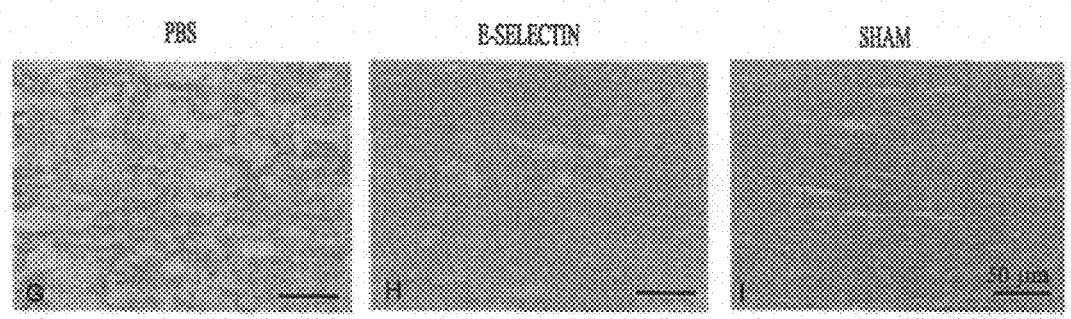
Figures 7A, 7B, 7C:
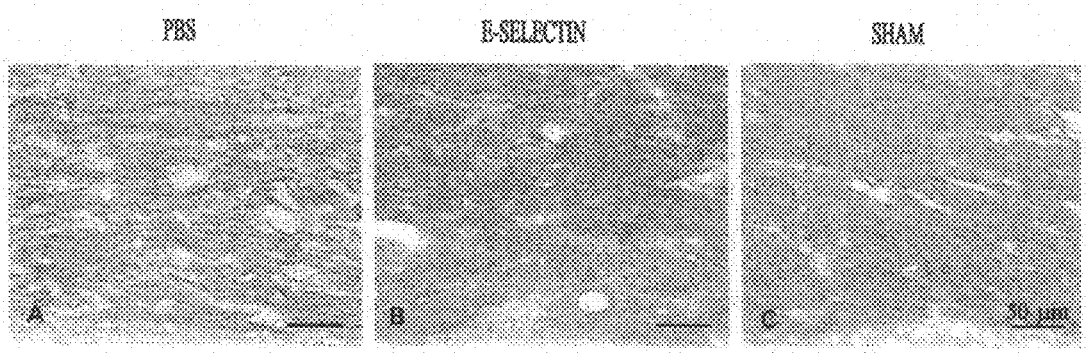
FIG. 7A-F shows photomicrographs of sections immunohistochemical stained using a cocktail of inonoclonal antibodies directed against non-phosphorylated neurofilaments (SMI 311) that were obtained from the corpus callosum (A, B, C) and caudoputamen (D, E, F) from rats. The rats were subjected to a sham operation (C, F) or to bilateral ligation of the carotid arteries in animals that also received intranasal PBS (A, D) or E-selectin (B, E) on a booster tolerization schedule. Note that the extent of the white matter rarefaction was less severe in the E-selectin treated and sham-operated rats as compared with PBS group.
Figures 7D, 7E, 7F:
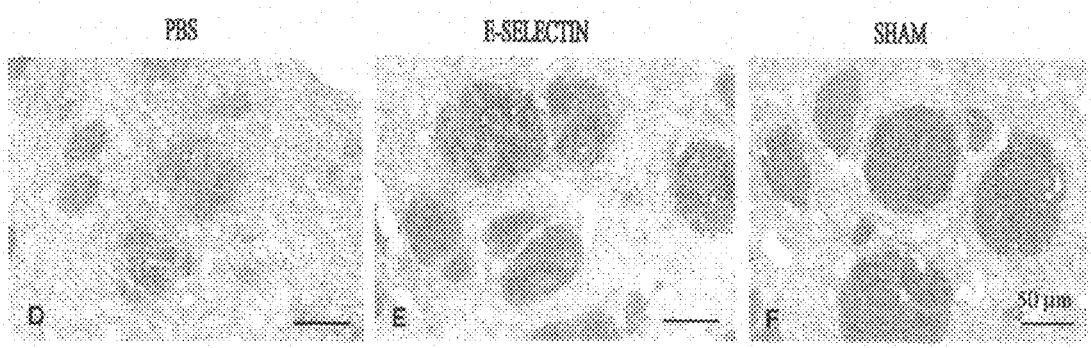
Figure 8:
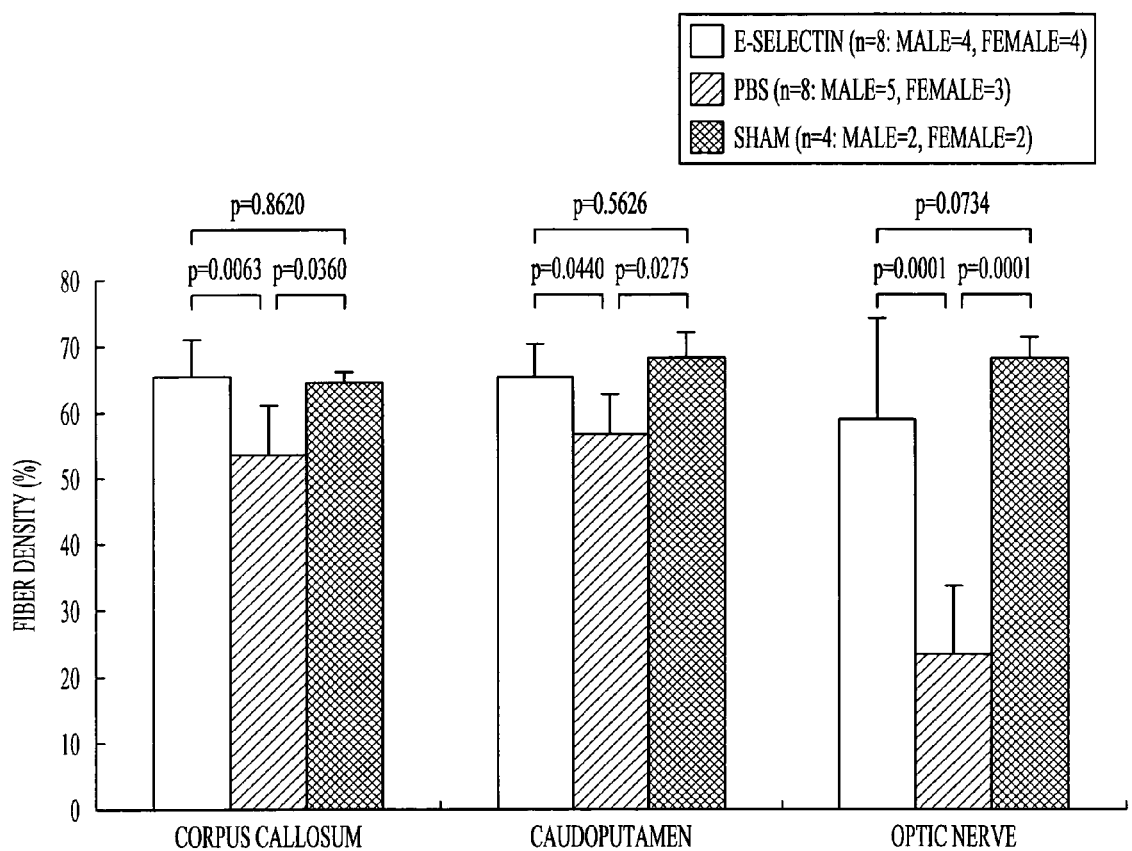
FIG. 8 graphically illustrates the fiber densities of the corpus callosum, caudoputamen and optic nerve in rats subjected to a sham operation or to bilateral ligation of the carotid arteries and intranasal administration of either PBS or E-selectin on a booster tolerization schedule. The fiber densities in E-selectin-treated animals were significantly higher than those in PBS-treated animals.

Histopathology: In the sham-operated animals, there was no detectable rarefaction in the white matter. However, rarefaction of the white matter was observed in the corpus callosum, in caudoputamen traversing fiber bundles and in the optic nerve in the PBS-treated rats. For these studies, luxol fast blue stain and immunocytochemistry with a cocktail of antibodies directed against nonphosphorylated neurofilaments (SMI 311) were used. The severity of the rarefaction was markedly attenuated in the animals treated with E-selectin (FIGS. 6, 7). In particular, the fiber densities in the E-selectin-treated animals were significantly higher than those in the PBS-treated group by two-factor ANOVA ($p<0.0001$). Moreover, there was no significant difference in the fiber densities between sham and E-selectin groups ($p=0.2026$) (FIG. 8). Thus, E-selectin mucosal tolerization had a protective effect against white matter rarefaction induced by protracted hypoperfusion.

The Pearson correlation coefficient between the fiber density of the optic nerve and the discrimination index in the E-selectin treated animals was minus 0.470. This correlation was not significantly different from 0 ($p=0.2537$). A few dark neurons were detected in the unilateral hippocampus of the three E-selectin-treated (27.3%), three PBS-treated animals (27.3%) and one sham-operated animal (25%). There were no obvious differences in the number of the dark neurons among three groups (data not shown).

Figure 10:
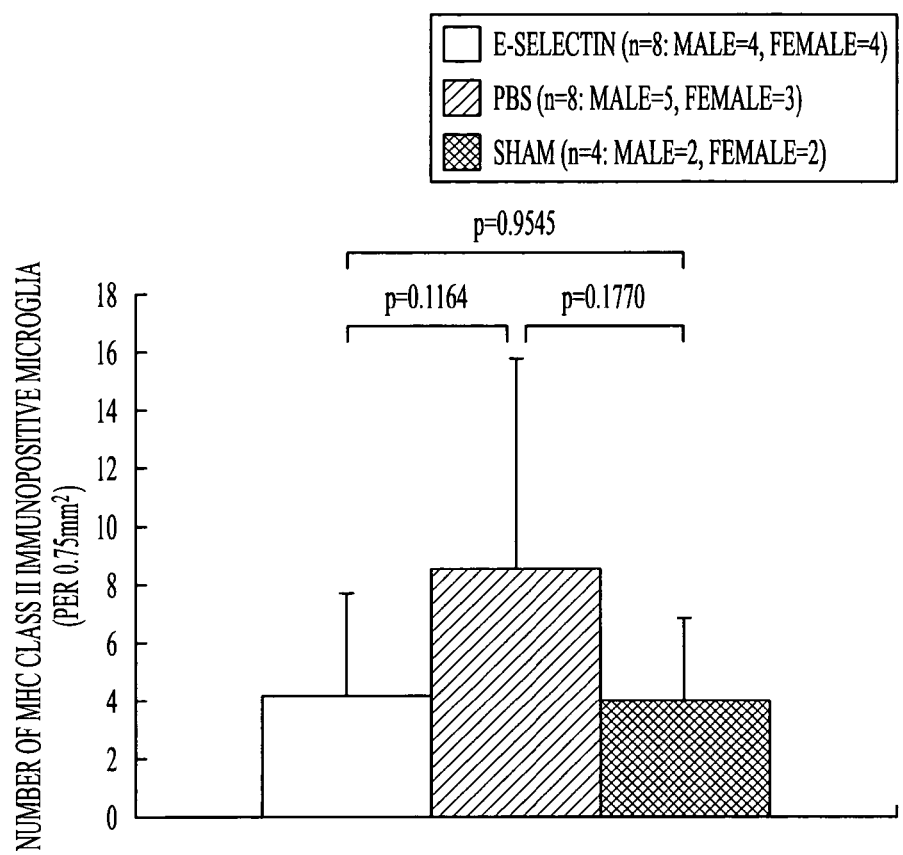
FIG. 10 shows histograms of the numerical densities of MHC class II immunopositive microglia/macrophages in the corpus callosum of rats subjected to a sham operation, or to bilateral ligation of the carotid arteries in animals that also received intranasal PBS or E-selectin on a booster tolerization schedule.

In the white matter of the sham-operated animals, there was positive immunostaining for the MHC class II (Ia) antigen in only a few glial cells. However, the brains of the PBS-treated animals showed an increase in the number of microglia/macrophages that were immunolabeled for the MHC class II (Ia) antigen. These microglia and macrophages were observed in the white matter within the corpus callosum and caudoputamen. In contrast, in E-selectin-treated rats, the number of microglia/macrophages positively immunolabeled for MHC class II antigen tended to correlate with a tendency towards a decrease in the white matter lesions as compared to PBS-treated animals (FIG. 9). However, there were no significant differences among E-selectin-treated group, sham-operated group and PBS-treated group (FIG. 10).

Figure 13:
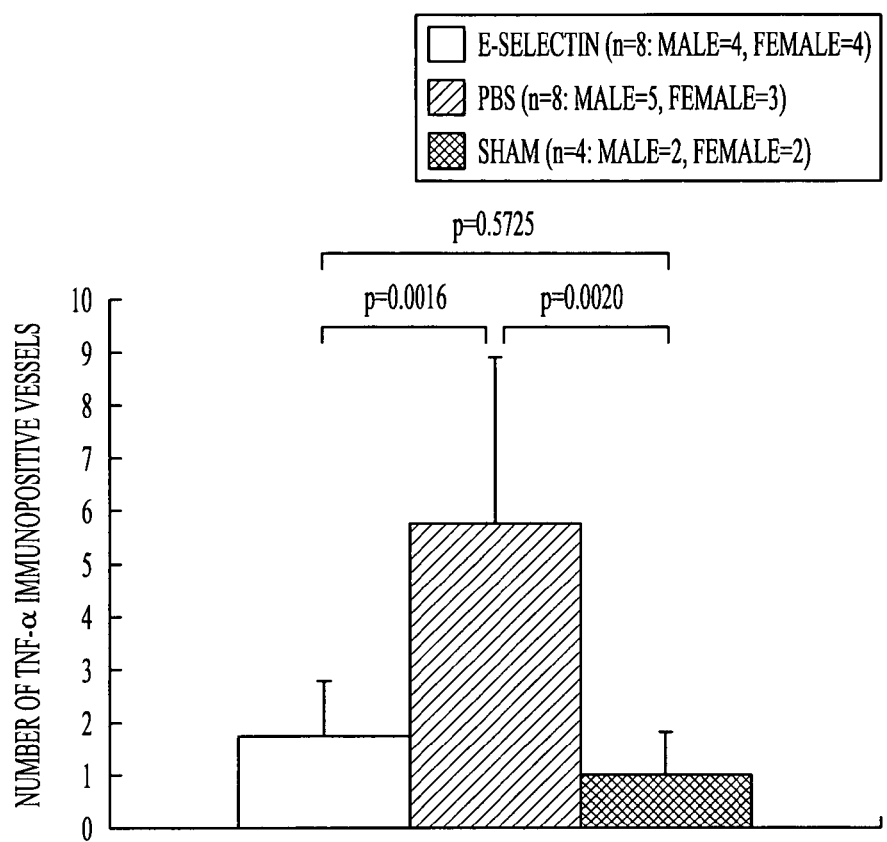
FIG. 13 shows histograms of the numerical density of TNF-α-immunopositive vessels in the corpus callosum of rats subjected to a sham operation, or to bilateral ligation of the carotid arteries in animals that also received intranasal PBS or E-selectin on a booster tolerization schedule. In the E-selectin-treated and sham-operated animals, the number of TNF-α-immunopositive vessels was significantly reduced as compared with the PBS-treated animals.

While TNF-α was prominently expressed in endothelial cells in blood vessels of the white matter, such TNF-α expression was markedly attenuated in E-selectin-tolerized and sham-operated animals (FIG. 12). The TNF immunoreactive vessels were significantly ($p=0.0016$) decreased in number in the E-selectin-treated groups as compared to the PBS-treated group. In contrast, there were no significant differences in the number of TNF immunoreactive vessels between the sham and E-selectin groups ($p=0.5725$) (FIG. 13).

Figures 14A, 14B, 14C:
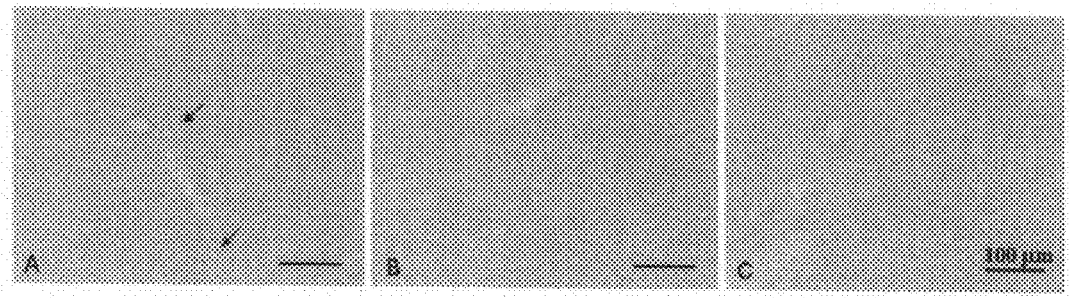
FIG. 14A-F shows photomicrographs of sections immuno-histochemically stained for detection of E-selectin in the corpus callosum. The rats were subjected to a sham operation (C, F) or to bilateral ligation of the carotid arteries in animals that also received intranasal PBS (A, D) or E-selectin (B, E) on a booster tolerization schedule. The sections were taken 90 days after carotid ligation. In the E-selectin-treated and sham-operated animals, E-selectin-immunopositive vessels were less prominent as compared to the PBS-treated animals.
Figures 14D, 14E, 14F:
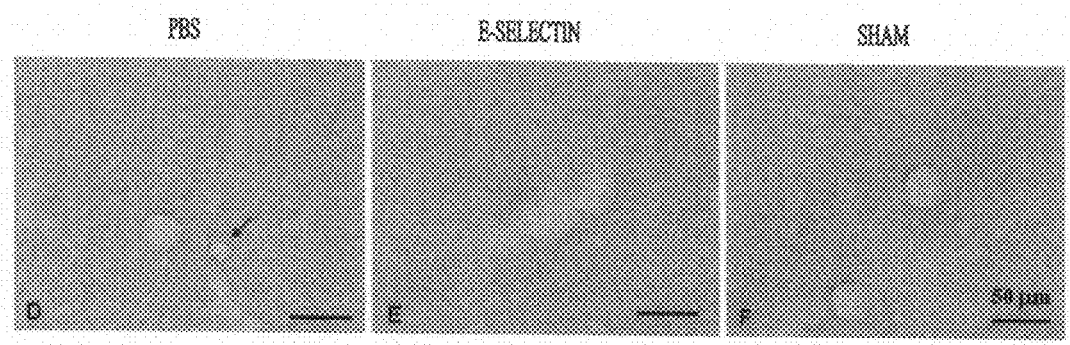
Figure 15:
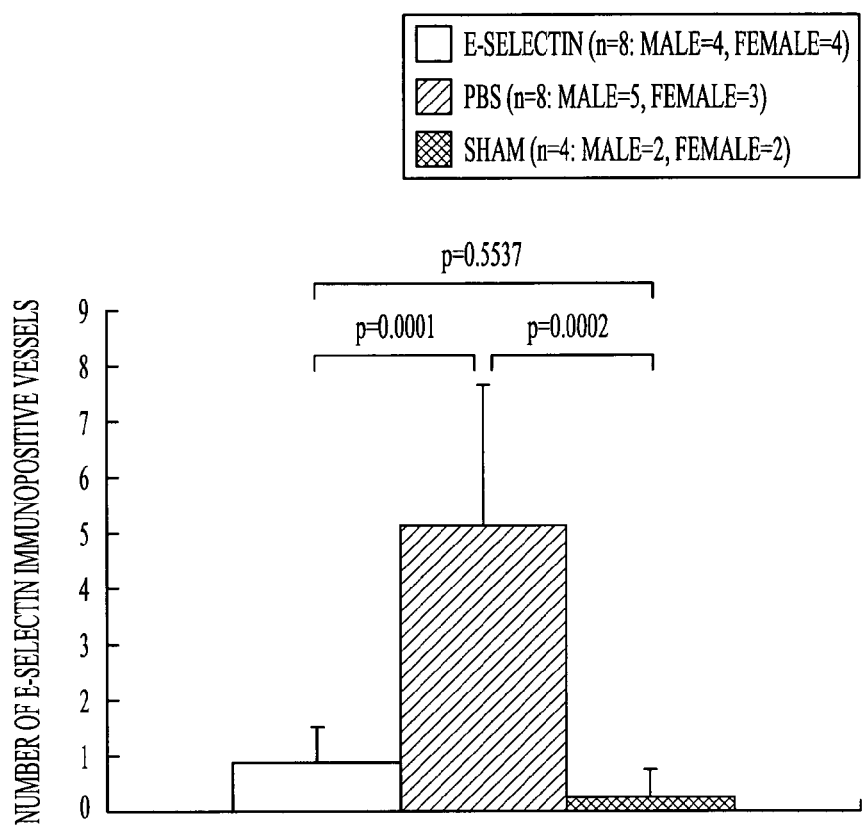
FIG. 15 shows histograms of the numerical density of E-selectin-immunopositive vessels in the corpus callosum of rats subjected to a sham operation, or to bilateral ligation of the carotid arteries and either intranasal PBS or intranasal E-selectin on a booster tolerization schedule. In the E-selectin-treated and sham-operated animals, the number of E-selectin-immunopositive vessels was significantly reduced as compared with the PBS-treated animals.

E-selectin was expressed in endothelial cells of vessels in the brains of the PBS-treated animals. The E-selectin immunoreactive vessels were decreased in number in the E-selectin-treated group as compared to the PBS-treated group (FIG. 14). The E-selectin-treated animals exhibited a significant reduction ($p=0.0001$) in the number of E-selectin immunopositive vessels as compared to the PBS-treated group. In contrast, there were no significant differences in the number of E-selectin immunoreactive vessels between sham and the E-selectin groups ($p=0.5537$) (FIG. 15). Thus, the mucosal tolerance to E-selectin had a suppressive effect against the activation of vessels in the brain induced by protracted hypoperfusion.

Immunoassay: The sham group had a statistically significantly lower level of plasma TNF than the E-selectin and PBS groups by one-factor ANOVA ($p<0.05$). However, there were no significant differences on the level of plasma TNF between the E-selectin and PBS groups.

The results provided above illustrate the protective effect of mucosal tolerance to E-selectin against histological damage and functional impairments that develops during protracted cerebral hypoperfusion induced by the permanent occlusion of both common carotid arteries.

Because the severity of the damage in the optic nerve was attenuated in the E-selectin-treated group as compared to the PBS-treated group, the potential effect of differential visual acuity on behavioral tests such as the object recognition test should be considered. In this study, the discrimination ability preserved by E-selectin treatment was not correlated with the degree of protection from fiber loss in the optic nerve. One explanation for this discrepancy is that humans primarily base their choices on a memory of visual the properties of the sample object. In contrast, when rats explore an object, they sniff it, palpate it with vibrissae, and look at it. In the rodents, differential exploration of familiar objects and novel objects reflects to some extent their memory for olfactory and tactile properties of the sample object, although visual properties may also be remembered and contribute to discrimination.

There were apparent differences in the protective effects conferred by E-selectin tolerization on T maze left/right discrimination memory when tested at the 2, 6 and 10 week time points. In contrast to 10 weeks after surgery, at 2 and 6 weeks after surgery the E-selectin group did not retain their left/right discrimination memory. The impairment in the left/right discrimination memory at 2 and 6 weeks after surgery might have been caused by a decrease of cerebral blood flow that impaired function without permanent cortical white matter damage. Cerebral blood flow in this model remains reduced over a prolonged period and gradually recovers to control levels by 8 weeks (Otori T, Cerebrovasc. Dis. 6 (suppl): 71 (1996)).

In the present study, plasma TNF level was increased in the ischemic groups (PBS and E-selectin), as compared with the sham-operated group even 90 days after surgery. Since the expression of E-selectin is induced in response to TNF, these findings suggest that the endothelial activation and E-selectin induction could persist for a prolonged period under conditions of protracted hypoperfusion. Mucosal tolerance can be achieved through different mechanisms, including clonal anergy/deletion of antigen-reactive T cells, and active tolerance with induction of regulatory T cells (Faria A M, Adv Immunol. 73:153-264 (1999)). Clonal anergy/deletion can be induced by a single feeding of very high-dose antigen (Chen Y., Nature. 376 (6536):177-180 (1995)) and the production of regulatory T cells occurs after repetitive administration of low-dose antigen (Groux H., Nature 389:737-742 (1997); Chen Y., Science 265:1237-1240 (1994)). Lymphocytes that are tolerized to an antigen and have become antigen-specific regulatory T-cells tend to migrate to the locale of the protein molecule to which they have been primed. In that location, they release immunomodulatory cytokines, such as TGF-β and IL-10 that counteract the effect of pro-inflammatory cytokines including TNF and suppress inflammation and immune responses after ischemia (Pang L., Stroke. 2001; 32:544-552 (2001), Hallenbeck J. M., Trends in Immunology 26:550-556 (2005)). Since local release of immunological and inflammatory mediators contributes to local vessel activation, local immunosuppression targeted to activating blood vessel segments could protect against local impairment of microcirculatory perfusion. In this study, the number of TNF immunopositive vessels and E-selectin immunopositive vessels were significantly decreased in the E-selectin tolerized group, compared to the PBS control group. But the plasma TNF level was not significantly decreased in the E-selectin group as compared with PBS group. These results indicate that local vessel activation and local TNF production was suppressed by the mucosal tolerance to E-selectin in a setting of undiminished systemic TNF production. TNF expressed by endothelium has proinflammatory and procoagulant effects on endothelium (Pober J S, Physiol Rev. 70:427-451 (1990), Hallenbeck J M. Nat. Med. 8:1363-1368 (2002)). E-selectin appears to function by suppressing local vessel activation and the surrounding immunological and inflammatory processes rather than by systemic immunosuppression.

Other mechanisms may also contribute to the protective effect in the present study. White matter injury involves glial cells, which are abundant in white matter (Goldberg M, Stroke 34:330-332 (2003)). In this model, microglial activation with expression of MHC class II antigens was detected preferentially in the white matter (Wakita H, Acta Neuropathol. (Berl) 87: 484-492 (1994); Farkas E., Acta Neuropathol (Berl). 108:57-64 (2004), Schmidt-Kastner R., Brain Res. 1052:28-39 (2005)), and pharmacological suppression of these activated microglia has resulted in an attenuation of the white matter lesions (Wakita H, Stroke 26:1415-1422 (1995); Wakita H, Brain Res. 792:105-113 (1998); Wakita H, Neuroreport 14:1461-1465 (1999), Wakita H., Brain Res. 992:53-59 (2003)).

Since TGF-β and IL-10 inhibit the activation of microglia (Suzumura A, J. Immunol. 151:2150-2158 (1993), Frei K, J. Immunol. 152:2720-2728 (1994)), mucosal tolerization to E-selectin suppresses the activated microglia through local production of these cytokines by the regulatory T cells. The number of MHC class II positive activated microglia/macrophages in the white matter showed a trend toward suppression in the E-selectin group as compared to the PBS group. Activated microglia may enhance a variety of inflammatory responses (Morioka T, J. Cereb. Blood Flow Metab. 1991; 11:966-973 (1991); Wakita H, Acta Neuropathol. (Berl) 87: 484-492 (1994); Gehrmann J, Brain Res. Rev. 20:269-287 (1995)). Microglia are the major source of pro-inflammatory cytokines including IL-1 and TNF, which may induce the expression of E-selectin in the ischemic cerebral vasculature. The suppression of the microglia may inhibit both local vessel activation and the expression of E-selectin. Activated microglia also release an array of cytotoxic substances that include other pro-inflammatory cytokines, prostanoids, proteases, reactive oxygen radicals and nitrogen intermediates. The protective effect may be mediated by suppressing the release of these cytotoxic substances as well. The net effect decreases inflammation and preserves vessel integrity.

In conclusion, the present study demonstrates the protective effect of mucosal tolerance to E-selectin against ischemic cerebrovascular white matter damage and memory impairment during protracted cerebral hypoperfusion. These results support a new therapeutic strategy that involves mucosal tolerization to E-selectin to protect against subcortical ischemic vascular cognitive impairment on a long-term basis.

EXAMPLE 5

E-Selectin Sequences Employed

For early experiments, a human E-selectin polypeptide with SEQ ID NO:30 was made by recombinant procedures using a pNVAX1002 expression vector. This SEQ ID NO:30 sequence is shown below.

```
  1 MGWSWIFLFL LSGTASVHSW SYNTSTEAMT YDEASAYCQQ
 41 RYTHLVAIQN KEEIEYLNSI LSYSPSYYWI GIRKVNNVWV
 81 WVGTQKPLTE EAKNWAPGEP NNRQKDEDCV EIYIKREKDV
121 GMWNDERCSK KKLALCYTAA CTNTSCSGHG ECVETINNYT
161 CKCDPGFSGL KCEQIVNCTA LESPEHGSLV CSHPLGNFSY
201 NSSCSISCDR GYLPSSMETM QCMSSGEWSA PIPACNVVEC
241 DAVTNPANGF VECFQNPGSF PWNTTCTFDC EEGFELMGAQ
281 SLQCTSSGNW DNEKPTCKAV TGGASTRAAE QKLISEEDLN
321 GTRSGHHRHH H
```

This SEQ ID NO:30 sequence has a signal sequence (MG-WSWIFLFL LSGTASVHS (SEQ ID NO:27)), which is cleaved during recombinant production and is not present in the purified product. The SEQ ID NO:30 E-selectin sequence also has a histidine tag sequence (GGASTRAAEQKLI SEEDLNGTRSGHHHHHH (SEQ ID NO:29)), which can facilitate isolation and detection of the E-selectin. Upon removal of the MGWSWIFLFL LSGTASVHS (SEQ ID NO:27) signal sequence a polypeptide with the following E-selectin polypeptide with SEQ ID NO:31 is generated.

```
  1                      W SYNTSTEAMT YDEASAYCQQ
 41 RYTHLVAIQN KEEIEYLNSI LSYSPSYYWI GIRKVNNVWV
 81 WVGTQKPLTE EAKNWAPGEP NNRQKDEDCV EIYIKREKDV
121 GMWNDERCSK KKLALCYTAA CTNTSCSGHG ECVETINNYT
161 CKCDPGFSGL KCEQIVNCTA LESPEHGSLV CSHPLGNFSY
201 NSSCSISCDR GYLPSSMETM QCMSSGEWSA PIPACNVVEC
241 DAVTNPANGF VECFQNPGSF PWNTTCTFDC EEGFELMGAQ
281 SLQCTSSGNW DNEKPTCKAV TGGASTRAAE QKLISEEDLN
321 GTRSGHHHHH H
```

For somewhat later experiments, a human E-selectin polypeptide with SEQ ID NO:32 was made by recombinant procedures using a pNVAX1037 expression vector. This SEQ ID NO:32 sequence is shown below.

```
  1 MGWSWIFLFL LSGTASVHSW SYNTSTEAMT YDEASAYCQQ
 41 RYTHLVAIQN KEEIEYLNSI LSYSPSYYWI GIRKVNNVWV
 81 WVGTQKPLTE EAKNWAPGEP NNRQKDEDCV EIYIKREKDV
121 GMWNDERCSK KKLALCYTAA CTNTSCSGHG ECVETINNYT
161 CKCDPGFSGL KCEQIVNCTA LESPEHGSLV CSHPLGNFSY
201 NSSCSISCDR GYLPSSMETM QCMSSGEWSA PIPACNVVEC
241 DAVTNPANGF VECFQNPGSF PWNTTCTFDC EEGFELMGAQ
281 SLQCTSSGNW DNEKPTCKAV T
```

This SEQ ID NO:32 sequence has a signal sequence (MGWSWIFLFL LSGTASVHS (SEQ ID NO:27)) but no histidine tag sequence. As indicated above, the SEQ ID NO:27 signal sequence is cleaved during recombinant production and is not present in the purified product. Upon removal of the SEQ ID NO:27 signal sequence, this E-selectin polypeptide has SEQ ID NO:8.

For more recent experiments, a mouse E-selectin polypeptide with SEQ ID NO:33 was made by recombinant procedures using a pNVAX1076 expression vector. This SEQ ID NO:33 sequence is shown below.

```
  1 MPLYKLLNVL WLVAVSNAIW YYNASSELMT YDEASAYCQR
 41 DYTHLVAIQN KEEINYLNSN LKHSPSYYWI GIRKVNNVWI
 81 WVGTGKPLTE EAQNWAPGEP NNKQRNEDCV ETYIQRTKDS
121 GMWNDERCNK KKLALCYTAS CTNASCSGHG ECIETINSYT
161 CKCHPGFLGP NCEQAVTCKP QEHPDYGSLN CSHPFGPFSY
201 NSSCSFGCKR GYLPSSMETT VRCTSSGEWS APAPACHVVE
241 CEALTHPAHG IRKCSSNPGS YPWNTTCTFD CVEGYRRVGA
281 QNLQCTSSGI WDNETPSCKA VT
```

This SEQ ID NO:33 sequence has an N-terminal signal sequence (MPLYKLLNVLWLVAVSNAI (SEQ ID NO:28)), which is cleaved and lost during recombinant production of the E-selectin product. Upon removal of the SEQ ID NO:28 signal sequence, this E-selectin polypeptide has SEQ ID NO:19.

Recent experiments have also employed a mouse E-selectin polypeptide with SEQ ID NO:18 was made by recombinant procedures using a pNVAX1189 expression vector. This SEQ ID NO:18 sequence is shown below.

```
  1 MGWSWIFLFL LSGTASVHSW YYNASSELMT YDEASAYCQR
 41 DYTHLVAIQN KEEINYLNSN LKHSPSYYWI GIRKVNNVWI
 81 WVGTGKPLTE EAQNWAPGEP NNKQRNEDCV EIYIQRTKDS
121 GMWNDERCNK KKLALCYTAS CTNASCSGHG ECIETINSYT
161 CKCHPGFLGP NCEQAVTCKP QEHPDYGSLN CSHPFGPFSY
201 NSSCSFGCKR GYLPSSMETT VRCTSSGEWS APAPACHVVE
241 CEALTHPAHG IRKCSSNPGS YPWNTTCTFD CVEGYRRVGA
281 QNLQCTSSGI WDNETPSCKA VT
```

This SEQ ID NO:18 sequence has a signal sequence (MGWSWIFLFL LSGTASVHS (SEQ ID NO:27)), which is cleaved during recombinant production and is not present in the purified product. Upon removal of the SEQ ID NO:27 signal sequence, this E-selectin polypeptide has SEQ ID NO:19.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A method for treating vascular dementia in a mammal comprising intranasal administration to the mammal of an amount of an E-selectin polypeptide sufficient to induce immunological tolerance to E-selectin in the mammal, wherein the E-selectin is human, bovine, murine or rat E-selectin.

2. The method of claim 1, wherein blood flow to the mammal's brain is reduced.

3. The method of claim 1, which further comprises a first series of administrations of E-selectin over a period of about two weeks.

4. The method of claim 3, wherein the first series of administrations comprises about three to about seven administrations of E-selectin over the period of about two weeks.

5. The method of claim 3, which further comprises at least one booster series of administrations of E-selectin after at least two weeks from the first series of administrations.

6. The method of claim 5, wherein each booster series of administrations comprise about three to about seven administrations of E-selectin over the period of two weeks.

7. The method of claim 1, wherein the intranasal administration is aerosol administration.

8. The method of claim 7, wherein the aerosol is a dry aerosol.

9. The method of claim 7, wherein the aerosol is an atomized aqueous solution.

10. The method of claim 1, wherein the E-selectin is human E-selectin.

11. The method of claim 1, wherein the E-selectin is bovine E-selectin, murine E-selectin or rat E-selectin.

12. The method of claim 1, wherein the E-selectin comprises one of SEQ ID NO:5-8, 18, 19, 30-33, or any combination thereof.

13. The method of claim 1, wherein an effective amount of E-selectin is sufficient to promote bystander-effect tolerance to E-selectin in a mammal.

14. The method of claim 1, wherein an effective amount of E-selectin is about 0.005 mg to about 500 mg.

15. The method of claim 1, wherein an effective amount of E-selectin is about 5 μg to about 50 mg.

16. A method for treating stroke in a mammal comprising intranasal administration to the mammal of an amount of an E-selectin polypeptide sufficient to induce immunological tolerance to E-selectin in the mammal; wherein the E-selectin polypeptide comprises one of SEQ ID NO:5-8, 18, 19, 30-33, or any combination thereof.

17. The method of claim 16, wherein the E-selectin polypeptide comprises SEQ ID NO: 8.

18. The method of claim 1, wherein the E-selectin polypeptide comprises SEQ ID NO: 8.

* * * * *